US011026627B2

(12) United States Patent
Scott et al.

(10) Patent No.: US 11,026,627 B2
(45) Date of Patent: Jun. 8, 2021

(54) SURGICAL INSTRUMENTS FOR DETERMINING A LOCATION OF A NERVE DURING A PROCEDURE

(71) Applicant: Cadwell Laboratories, Inc., Kennewick, WA (US)

(72) Inventors: Justin Scott, Pasco, WA (US); John Cadwell, Kennewick, WA (US)

(73) Assignee: Cadwell Laboratories, Inc., Kennewick, WA (US)

( * ) Notice: Subject to any disclaimer, the term of this patent is extended or adjusted under 35 U.S.C. 154(b) by 350 days.

(21) Appl. No.: 16/129,236

(22) Filed: Sep. 12, 2018

(65) Prior Publication Data

US 2019/0133522 A1 May 9, 2019

Related U.S. Application Data

(63) Continuation of application No. 14/206,945, filed on Mar. 12, 2014, now Pat. No. 10,098,585.
(Continued)

(51) Int. Cl.
*A61B 5/00* (2006.01)
*A61B 5/04* (2006.01)
(Continued)

(52) U.S. Cl.
CPC .............. *A61B 5/4893* (2013.01); *A61B 5/24* (2021.01); *A61B 5/4041* (2013.01); *A61N 1/36017* (2013.01)

(58) Field of Classification Search
CPC . A61B 5/04001; A61B 5/4893; A61B 5/4041; A61N 1/36017
See application file for complete search history.

(56) References Cited

U.S. PATENT DOCUMENTS 751,475 A 2/1904 De Vilbiss
972,983 A 10/1910 Arthur
(Continued)

FOREIGN PATENT DOCUMENTS

AT 466451 T 5/2010
AT 539680 T 1/2012
(Continued)

OTHER PUBLICATIONS

Aage R. Møller, "Intraoperative Neurophysiologic Monitoring", University of Pittsburgh, School of Medicine Pennsylvania, © 1995 by Harwood Academic Publishers GmbH.
(Continued)

*Primary Examiner* — Christine H Matthews
*Assistant Examiner* — Joshua Daryl D Lannu
(74) *Attorney, Agent, or Firm* — Novel IP

(57) ABSTRACT

Systems, devices and methods are provided for neuromonitoring, particularly neuromonitoring to reduce the risks of contacting or damaging nerves or causing patient discomfort during and after surgical procedures, including spinal surgeries. The neuromonitoring procedures include monitoring for the presence of or damage to sensory nerves, and optionally includes additional monitoring for motor nerves. In some systems, including systems that monitor for both sensory and motor nerves, components of the monitoring systems (e.g., stimulating electrodes and response sensors), may be combined with one or more surgical instruments. The systems, devices, and methods provide for pre-surgical assessment of neural anatomy and surgical planning, intra-operative monitoring of nerve condition, and post-operative assessment of nerve position and health.

20 Claims, 12 Drawing Sheets

Related U.S. Application Data

(60) Provisional application No. 61/792,339, filed on Mar. 15, 2013.

(51) Int. Cl.
*A61B 5/24* (2021.01)
*A61N 1/36* (2006.01)

(56) References Cited

U.S. PATENT DOCUMENTS

| | | |
|---|---|---|
| 1,328,624 A | 1/1920 | Graham |
| 1,477,527 A | 12/1923 | Raettig |
| 1,548,184 A | 8/1925 | Cameron |
| 1,717,480 A | 6/1929 | Wappler |
| 1,842,323 A | 1/1932 | Gluzek |
| 2,110,735 A | 3/1938 | Marton |
| 2,320,709 A | 6/1943 | Arnesen |
| 2,516,882 A | 8/1950 | Kalom |
| 2,704,064 A | 3/1955 | Fizzell |
| 2,736,002 A | 2/1956 | Oriel |
| 2,807,259 A | 9/1957 | Federico |
| 2,808,826 A | 10/1957 | Reiner |
| 2,994,324 A | 8/1961 | Albano Lemos |
| 3,035,580 A | 5/1962 | Methodi |
| 3,057,356 A | 10/1962 | Greatbatch |
| 3,060,923 A | 10/1962 | Reiner |
| 3,087,486 A | 4/1963 | Kilpatrick |
| 3,147,750 A | 9/1964 | Fry |
| 3,188,605 A | 6/1965 | Slenker |
| 3,212,496 A | 10/1965 | Preston |
| 3,219,029 A | 11/1965 | Richards |
| 3,313,293 A | 4/1967 | Chesebrough |
| 3,364,929 A | 1/1968 | Ide |
| 3,580,242 A | 5/1971 | La Croix |
| 3,611,262 A | 10/1971 | Marley |
| 3,617,616 A | 11/1971 | O'Loughlin |
| 3,641,993 A | 2/1972 | Gaarder |
| 3,646,500 A | 2/1972 | Wessely |
| 3,651,812 A | 3/1972 | Samuels |
| 3,662,744 A | 5/1972 | Richardson |
| 3,664,329 A | 5/1972 | Naylor |
| 3,682,162 A | 8/1972 | Colyer |
| 3,703,900 A | 11/1972 | Holznagel |
| 3,718,132 A | 2/1973 | Holt |
| 3,733,574 A | 5/1973 | Scoville |
| 3,785,368 A | 1/1974 | Mc Carthy |
| 3,830,226 A | 8/1974 | Staub |
| 3,857,398 A | 12/1974 | Rubin |
| 3,880,144 A | 4/1975 | Coursin |
| 3,933,157 A | 1/1976 | Bjurwill |
| 3,957,036 A | 5/1976 | Normann |
| 3,960,141 A | 6/1976 | Bolduc |
| 3,985,125 A | 10/1976 | Rose |
| 4,062,365 A | 12/1977 | Kameny |
| 4,088,141 A | 5/1978 | Niemi |
| 4,099,519 A | 7/1978 | Warren |
| 4,127,312 A | 11/1978 | Fleischhacker |
| 4,141,365 A | 2/1979 | Fischell |
| 4,155,353 A | 5/1979 | Rea |
| 4,164,214 A | 8/1979 | Pelzner |
| 4,175,551 A | 11/1979 | D'Haenens |
| 4,177,799 A | 12/1979 | Masreliez |
| 4,184,492 A | 1/1980 | Fastenmeier |
| 4,200,104 A | 4/1980 | Harris |
| 4,204,545 A | 5/1980 | Yamakoshi |
| 4,207,897 A | 6/1980 | Evatt |
| 4,224,949 A | 9/1980 | Scott |
| 4,226,228 A | 10/1980 | Shin |
| 4,232,680 A | 11/1980 | Hudleson |
| 4,233,987 A | 11/1980 | Feingold |
| 4,235,242 A | 11/1980 | Heule |
| 4,263,899 A | 4/1981 | Burgin |
| 4,265,237 A | 5/1981 | Schwanbom |
| 4,285,347 A | 8/1981 | Hess |
| 4,291,705 A | 9/1981 | Severinghaus |
| 4,294,245 A | 10/1981 | Bussey |
| 4,295,703 A | 10/1981 | Osborne |
| 4,299,230 A | 11/1981 | Kubota |
| 4,308,012 A | 12/1981 | Tamler |
| 4,331,157 A | 5/1982 | Keller, Jr. |
| 4,372,319 A | 2/1983 | Ichinomiya |
| 4,373,531 A | 2/1983 | Wittkampf |
| 4,374,517 A | 2/1983 | Hagiwara |
| 4,402,323 A | 9/1983 | White |
| 4,444,187 A | 4/1984 | Perlin |
| 4,461,300 A | 7/1984 | Christensen |
| 4,469,098 A | 9/1984 | Davi |
| 4,483,338 A | 11/1984 | Bloom |
| 4,485,823 A | 12/1984 | Yamaguchi |
| 4,487,489 A | 12/1984 | Takamatsu |
| 4,503,842 A | 3/1985 | Takayama |
| 4,503,863 A | 3/1985 | Katims |
| 4,510,939 A | 4/1985 | Brenman |
| 4,515,168 A | 5/1985 | Chester |
| 4,517,976 A | 5/1985 | Murakoshi |
| 4,517,983 A | 5/1985 | Toyosu |
| 4,519,403 A | 5/1985 | Dickhudt |
| 4,537,198 A | 8/1985 | Corbett |
| 4,545,374 A | 10/1985 | Jacobson |
| 4,557,273 A | 12/1985 | Stoller |
| 4,558,703 A | 12/1985 | Hermann |
| 4,561,445 A | 12/1985 | Berke |
| 4,562,832 A | 1/1986 | Wilder |
| 4,565,200 A | 1/1986 | Cosman |
| 4,570,640 A | 2/1986 | Barsa |
| 4,573,448 A | 3/1986 | Kambin |
| 4,573,449 A | 3/1986 | Warnke |
| 4,576,178 A | 3/1986 | Johnson |
| 4,582,063 A | 4/1986 | Mickiewicz |
| 4,592,369 A | 6/1986 | Davis |
| 4,595,018 A | 6/1986 | Rantala |
| 4,616,635 A | 10/1986 | Caspar |
| 4,616,660 A | 10/1986 | Johns |
| 4,622,973 A | 11/1986 | Agarwala |
| 4,633,889 A | 1/1987 | Talalla |
| 4,641,661 A | 2/1987 | Kalarickal |
| 4,643,507 A | 2/1987 | Coldren |
| 4,658,835 A | 4/1987 | Pohndorf |
| 4,667,676 A | 5/1987 | Guinta |
| 4,697,598 A | 10/1987 | Bernard |
| 4,697,599 A | 10/1987 | Woodley |
| 4,705,049 A | 11/1987 | John |
| 4,716,901 A | 1/1988 | Jackson |
| 4,739,772 A | 4/1988 | Hokanson |
| 4,744,371 A | 5/1988 | Harris |
| 4,759,377 A | 7/1988 | Dykstra |
| 4,763,666 A | 8/1988 | Strian |
| 4,765,311 A | 8/1988 | Kulik |
| 4,784,150 A | 11/1988 | Voorhies |
| 4,785,812 A | 11/1988 | Pihl |
| 4,795,998 A | 1/1989 | Dunbar |
| 4,807,642 A | 2/1989 | Brown |
| 4,807,643 A | 2/1989 | Rosier |
| 4,817,587 A | 4/1989 | Janese |
| 4,817,628 A | 4/1989 | Zealear |
| 4,827,935 A | 5/1989 | Geddes |
| 4,841,973 A | 6/1989 | Stecker |
| 4,844,091 A | 7/1989 | Bellak |
| 4,862,891 A | 9/1989 | Smith |
| 4,892,105 A | 1/1990 | Prass |
| 4,895,152 A | 1/1990 | Callaghan |
| 4,920,968 A | 5/1990 | Takase |
| 4,926,865 A | 5/1990 | Oman |
| 4,926,880 A | 5/1990 | Claude |
| 4,934,377 A | 6/1990 | Bova |
| 4,934,378 A | 6/1990 | Perry, Jr. |
| 4,934,957 A | 6/1990 | Bellusci |
| 4,962,766 A | 10/1990 | Herzon |
| 4,964,411 A | 10/1990 | Johnson |
| 4,964,811 A | 10/1990 | Hayes, Sr. |
| 4,984,578 A | 1/1991 | Keppel |
| 4,998,796 A | 3/1991 | Bonanni |
| 5,007,902 A | 4/1991 | Witt |
| 5,015,247 A | 5/1991 | Michelson |

(56) References Cited

U.S. PATENT DOCUMENTS

| | | | |
|---|---|---|---|
| 5,018,526 | A | 5/1991 | Gaston-Johansson |
| 5,020,542 | A | 6/1991 | Rossmann |
| 5,024,228 | A | 6/1991 | Goldstone |
| 5,058,602 | A | 10/1991 | Brody |
| 5,080,606 | A | 1/1992 | Burkard |
| 5,081,990 | A | 1/1992 | Deletis |
| 5,085,226 | A | 2/1992 | DeLuca |
| 5,092,344 | A | 3/1992 | Lee |
| 5,095,905 | A | 3/1992 | Klepinski |
| 5,125,406 | A | 6/1992 | Goldstone |
| 5,127,403 | A | 7/1992 | Brownlee |
| 5,131,389 | A | 7/1992 | Giordani |
| 5,143,081 | A | 9/1992 | Young |
| 5,146,920 | A | 9/1992 | Yuuchi |
| 5,161,533 | A | 11/1992 | Prass |
| 5,163,328 | A | 11/1992 | Holland |
| 5,171,279 | A | 12/1992 | Mathews |
| 5,190,048 | A | 3/1993 | Wilkinson |
| 5,191,896 | A | 3/1993 | Gafni |
| 5,195,530 | A | 3/1993 | Shindel |
| 5,195,532 | A | 3/1993 | Schumacher |
| 5,196,015 | A | 3/1993 | Neubardt |
| 5,199,899 | A | 4/1993 | Ittah |
| 5,201,325 | A | 4/1993 | McEwen |
| 5,215,100 | A | 6/1993 | Spitz |
| RE34,390 | E | 9/1993 | Culver |
| 5,253,656 | A | 10/1993 | Rincoe |
| 5,255,691 | A | 10/1993 | Otten |
| 5,277,197 | A | 1/1994 | Church |
| 5,282,468 | A | 2/1994 | Klepinski |
| 5,284,153 | A | 2/1994 | Raymond |
| 5,284,154 | A | 2/1994 | Raymond |
| 5,292,309 | A | 3/1994 | Van Tassel |
| 5,299,563 | A | 4/1994 | Seton |
| 5,306,236 | A | 4/1994 | Blumenfeld |
| 5,312,417 | A | 5/1994 | Wilk |
| 5,313,956 | A | 5/1994 | Knutsson |
| 5,313,962 | A | 5/1994 | Obenchain |
| 5,327,902 | A | 7/1994 | Lemmen |
| 5,333,618 | A | 8/1994 | Lekhtman |
| 5,343,871 | A | 9/1994 | Bittman |
| 5,347,989 | A | 9/1994 | Monroe |
| 5,358,423 | A | 10/1994 | Burkhard |
| 5,358,514 | A | 10/1994 | Schulman |
| 5,368,043 | A | 11/1994 | Sunouchi |
| 5,373,317 | A | 12/1994 | Salvati |
| 5,375,067 | A | 12/1994 | Berchin |
| 5,377,667 | A | 1/1995 | Patton |
| 5,381,805 | A | 1/1995 | Tuckett |
| 5,383,876 | A | 1/1995 | Nardella |
| 5,389,069 | A | 2/1995 | Weaver |
| 5,405,365 | A | 4/1995 | Hoegnelid |
| 5,413,111 | A | 5/1995 | Wilkinson |
| 5,454,365 | A | 10/1995 | Bonutti |
| 5,470,349 | A | 11/1995 | Kleditsch |
| 5,472,426 | A | 12/1995 | Bonati |
| 5,474,558 | A | 12/1995 | Neubardt |
| 5,480,440 | A | 1/1996 | Kambin |
| 5,482,038 | A | 1/1996 | Ruff |
| 5,484,437 | A | 1/1996 | Michelson |
| 5,485,852 | A | 1/1996 | Johnson |
| 5,491,299 | A | 2/1996 | Naylor |
| 5,514,005 | A | 5/1996 | Jaycox |
| 5,514,165 | A | 5/1996 | Malaugh |
| 5,522,386 | A | 6/1996 | Lerner |
| 5,540,235 | A | 7/1996 | Wilson |
| 5,549,656 | A | 8/1996 | Reiss |
| 5,560,372 | A | 10/1996 | Cory |
| 5,565,779 | A | 10/1996 | Arakawa |
| 5,566,678 | A | 10/1996 | Cadwell |
| 5,569,248 | A | 10/1996 | Mathews |
| 5,575,284 | A | 11/1996 | Athan |
| 5,579,781 | A | 12/1996 | Cooke |
| 5,591,216 | A | 1/1997 | Testerman |
| 5,593,429 | A | 1/1997 | Ruff |
| 5,599,279 | A | 2/1997 | Slotman |
| 5,601,608 | A | 2/1997 | Mouchawar |
| 5,618,208 | A | 4/1997 | Crouse |
| 5,620,483 | A | 4/1997 | Minogue |
| 5,622,515 | A | 4/1997 | Hotea |
| 5,630,813 | A | 5/1997 | Kieturakis |
| 5,634,472 | A | 6/1997 | Raghuprasad |
| 5,671,752 | A | 9/1997 | Sinderby |
| 5,681,265 | A | 10/1997 | Maeda |
| 5,687,080 | A | 11/1997 | Hoyt |
| 5,707,359 | A | 1/1998 | Bufalini |
| 5,711,307 | A | 1/1998 | Smits |
| 5,725,514 | A | 3/1998 | Grinblat |
| 5,728,046 | A | 3/1998 | Mayer |
| 5,741,253 | A | 4/1998 | Michelson |
| 5,741,261 | A | 4/1998 | Moskovitz |
| 5,759,159 | A | 6/1998 | Masreliez |
| 5,769,781 | A | 6/1998 | Chappuis |
| 5,772,597 | A | 6/1998 | Goldberger |
| 5,772,661 | A | 6/1998 | Michelson |
| 5,775,331 | A | 7/1998 | Raymond |
| 5,776,144 | A | 7/1998 | Leysieffer |
| 5,779,642 | A | 7/1998 | Nightengale |
| 5,785,648 | A | 7/1998 | Min |
| 5,785,658 | A | 7/1998 | Benaron |
| 5,792,044 | A | 8/1998 | Foley |
| 5,795,291 | A | 8/1998 | Koros |
| 5,797,854 | A | 8/1998 | Hedgecock |
| 5,806,522 | A | 9/1998 | Katims |
| 5,814,073 | A | 9/1998 | Bonutti |
| 5,830,150 | A | 11/1998 | Palmer |
| 5,830,151 | A | 11/1998 | Hadzic |
| 5,833,714 | A | 11/1998 | Loeb |
| 5,836,880 | A | 11/1998 | Pratt |
| 5,851,191 | A | 12/1998 | Gozani |
| 5,853,373 | A | 12/1998 | Griffith |
| 5,857,986 | A | 1/1999 | Moriyasu |
| 5,860,829 | A | 1/1999 | Hower |
| 5,860,973 | A | 1/1999 | Michelson |
| 5,862,314 | A | 1/1999 | Jeddeloh |
| 5,868,668 | A | 2/1999 | Weiss |
| 5,872,314 | A | 2/1999 | Clinton |
| 5,885,210 | A | 3/1999 | Cox |
| 5,885,219 | A | 3/1999 | Nightengale |
| 5,888,196 | A | 3/1999 | Bonutti |
| 5,891,147 | A | 4/1999 | Moskovitz |
| 5,895,298 | A | 4/1999 | Faupel |
| 5,902,231 | A | 5/1999 | Foley |
| 5,924,984 | A | 7/1999 | Rao |
| 5,928,030 | A | 7/1999 | Daoud |
| 5,928,139 | A | 7/1999 | Koros |
| 5,928,158 | A | 7/1999 | Aristides |
| 5,931,777 | A | 8/1999 | Sava |
| 5,944,658 | A | 8/1999 | Koros |
| 5,954,635 | A | 9/1999 | Foley |
| 5,954,716 | A | 9/1999 | Sharkey |
| 5,993,385 | A | 11/1999 | Johnston |
| 5,993,434 | A | 11/1999 | Dev |
| 6,004,262 | A | 12/1999 | Putz |
| 6,004,312 | A | 12/1999 | Finneran |
| 6,004,341 | A | 12/1999 | Zhu |
| 6,009,347 | A | 12/1999 | Hofmann |
| 6,011,985 | A | 1/2000 | Athan |
| 6,027,456 | A | 2/2000 | Feler |
| 6,029,090 | A | 2/2000 | Herbst |
| 6,038,469 | A | 3/2000 | Karlsson |
| 6,038,477 | A | 3/2000 | Kayyali |
| 6,042,540 | A | 3/2000 | Johnston |
| 6,050,992 | A | 4/2000 | Nichols |
| 6,074,343 | A | 6/2000 | Nathanson |
| 6,077,237 | A | 6/2000 | Campbell |
| 6,095,987 | A | 8/2000 | Shmulewitz |
| 6,104,957 | A | 8/2000 | Alo |
| 6,104,960 | A | 8/2000 | Duysens |
| 6,119,068 | A | 9/2000 | Kannonji |
| 6,120,503 | A | 9/2000 | Michelson |
| 6,126,660 | A | 10/2000 | Dietz |
| 6,128,576 | A | 10/2000 | Nishimoto |
| 6,132,386 | A | 10/2000 | Gozani |

(56) References Cited

U.S. PATENT DOCUMENTS

| | | |
|---|---|---|
| 6,132,387 A | 10/2000 | Gozani |
| 6,135,965 A | 10/2000 | Tumer |
| 6,139,493 A | 10/2000 | Koros |
| 6,139,545 A | 10/2000 | Utley |
| 6,146,334 A | 11/2000 | Laserow |
| 6,146,335 A | 11/2000 | Gozani |
| 6,152,871 A | 11/2000 | Foley |
| 6,161,047 A | 12/2000 | King |
| 6,181,961 B1 | 1/2001 | Prass |
| 6,196,969 B1 | 3/2001 | Bester |
| 6,206,826 B1 | 3/2001 | Mathews |
| 6,210,324 B1 | 4/2001 | Reno |
| 6,214,035 B1 | 4/2001 | Streeter |
| 6,224,545 B1 | 5/2001 | Cocchia |
| 6,224,549 B1 | 5/2001 | Drongelen |
| 6,234,953 B1 | 5/2001 | Thomas |
| 6,249,706 B1 | 6/2001 | Sobota |
| 6,259,945 B1 | 7/2001 | Epstein |
| 6,266,558 B1 | 7/2001 | Gozani |
| 6,273,905 B1 | 8/2001 | Streeter |
| 6,287,322 B1 | 9/2001 | Zhu |
| 6,292,701 B1 | 9/2001 | Prass |
| 6,298,256 B1 | 10/2001 | Meyer |
| 6,302,842 B1 | 10/2001 | Auerbach |
| 6,306,100 B1 | 10/2001 | Prass |
| 6,309,349 B1 | 10/2001 | Bertolero |
| 6,312,392 B1 | 11/2001 | Herzon |
| 6,314,324 B1 | 11/2001 | Lattner |
| 6,325,764 B1 | 12/2001 | Griffith |
| 6,334,068 B1 | 12/2001 | Hacker |
| 6,346,078 B1 | 2/2002 | Ellman |
| 6,348,058 B1 | 2/2002 | Melkent |
| 6,366,813 B1 | 4/2002 | DiLorenzo |
| 6,391,005 B1 | 5/2002 | Lum |
| 6,393,325 B1 | 5/2002 | Mann |
| 6,425,859 B1 | 7/2002 | Foley |
| 6,425,901 B1 | 7/2002 | Zhu |
| 6,441,747 B1 | 8/2002 | Khair |
| 6,450,952 B1 | 9/2002 | Rioux |
| 6,451,015 B1 | 9/2002 | Rittman, III |
| 6,461,352 B2 | 10/2002 | Morgan |
| 6,466,817 B1 | 10/2002 | Kaula |
| 6,487,446 B1 | 11/2002 | Hill |
| 6,500,128 B2 | 12/2002 | Marino |
| 6,500,173 B2 | 12/2002 | Underwood |
| 6,500,180 B1 | 12/2002 | Foley |
| 6,500,210 B1 | 12/2002 | Sabolich |
| 6,507,755 B1 | 1/2003 | Gozani |
| 6,511,427 B1 | 1/2003 | Sliwa, Jr. |
| 6,535,759 B1 | 3/2003 | Epstein |
| 6,543,299 B2 | 4/2003 | Taylor |
| 6,546,271 B1 | 4/2003 | Reisfeld |
| 6,564,078 B1 | 5/2003 | Marino |
| 6,568,961 B1 | 5/2003 | Liburdi |
| 6,577,236 B2 | 6/2003 | Harman |
| 6,579,244 B2 | 6/2003 | Goodwin |
| 6,582,441 B1 | 6/2003 | He |
| 6,585,638 B1 | 7/2003 | Yamamoto |
| 6,609,018 B2 | 8/2003 | Cory |
| 6,618,626 B2 | 9/2003 | West, Jr. |
| 6,623,500 B1 | 9/2003 | Cook |
| 6,638,101 B1 | 10/2003 | Botelho |
| 6,712,795 B1 | 3/2004 | Cohen |
| 6,719,692 B2 | 4/2004 | Kleffner |
| 6,730,021 B2 | 5/2004 | Vassiliades, Jr. |
| 6,770,074 B2 | 8/2004 | Michelson |
| 6,805,668 B1 | 10/2004 | Cadwell |
| 6,819,956 B2 | 11/2004 | DiLorenzo |
| 6,839,594 B2 | 1/2005 | Cohen |
| 6,847,849 B2 | 1/2005 | Mamo |
| 6,851,430 B2 | 2/2005 | Tsou |
| 6,855,105 B2 | 2/2005 | Jackson, III |
| 6,870,109 B1 | 3/2005 | Villarreal |
| 6,901,928 B2 | 6/2005 | Loubser |
| 6,902,569 B2 | 6/2005 | Parmer |
| 6,916,294 B2 | 7/2005 | Ayad |
| 6,916,330 B2 | 7/2005 | Simonson |
| 6,926,728 B2 | 8/2005 | Zucherman |
| 6,929,606 B2 | 8/2005 | Ritland |
| 6,932,816 B2 | 8/2005 | Phan |
| 6,945,933 B2 | 9/2005 | Branch |
| 7,024,247 B2 | 4/2006 | Gliner |
| 7,072,521 B1 | 7/2006 | Cadwell |
| 7,079,883 B2 | 7/2006 | Marino |
| 7,089,059 B1 | 8/2006 | Pless |
| 7,104,965 B1 | 9/2006 | Jiang |
| 7,129,836 B2 | 10/2006 | Lawson |
| 7,153,279 B2 | 12/2006 | Ayad |
| 7,156,686 B1 | 1/2007 | Sekela |
| 7,177,677 B2 | 2/2007 | Kaula |
| 7,214,197 B2 | 5/2007 | Prass |
| 7,216,001 B2 | 5/2007 | Hacker |
| 7,230,688 B1 | 6/2007 | Villarreal |
| 7,236,822 B2 | 6/2007 | Dobak, III |
| 7,258,688 B1 | 8/2007 | Shah |
| 7,261,688 B2 | 8/2007 | Smith |
| 7,294,127 B2 | 11/2007 | Leung |
| 7,306,563 B2 | 12/2007 | Huang |
| 7,310,546 B2 | 12/2007 | Prass |
| 7,363,079 B1 | 4/2008 | Thacker |
| 7,374,448 B1 | 5/2008 | Jepsen |
| D574,955 S | 8/2008 | Lash |
| 7,470,236 B1 | 12/2008 | Kelleher |
| 7,496,407 B2 | 2/2009 | Odderson |
| 7,522,953 B2 | 4/2009 | Kaula |
| 7,546,993 B1 | 6/2009 | Walker |
| 7,605,738 B2 | 10/2009 | Kuramochi |
| 7,664,544 B2 | 2/2010 | Miles |
| 7,689,292 B2 | 3/2010 | Hadzic |
| 7,713,210 B2 | 5/2010 | Byrd |
| D621,041 S | 8/2010 | Mao |
| 7,775,974 B2 | 8/2010 | Buckner |
| 7,789,695 B2 | 9/2010 | Radle |
| 7,789,833 B2 | 9/2010 | Urbano |
| 7,801,601 B2 | 9/2010 | Maschino |
| 7,824,410 B2 | 11/2010 | Simonson |
| 7,869,881 B2 | 1/2011 | Libbus |
| 7,878,981 B2 | 2/2011 | Strother |
| 7,914,350 B1 | 3/2011 | Bozich |
| 7,963,927 B2 | 6/2011 | Kelleher |
| 7,974,702 B1 | 7/2011 | Fain |
| 7,983,761 B2 | 7/2011 | Giuntoli |
| 7,987,001 B2 | 7/2011 | Teichman |
| 7,988,688 B2 | 8/2011 | Webb |
| 7,993,269 B2 | 8/2011 | Donofrio |
| 8,002,770 B2 | 8/2011 | Swanson |
| 8,061,014 B2 | 11/2011 | Smith |
| 8,068,910 B2 | 11/2011 | Gerber |
| 8,126,736 B2 | 2/2012 | Anderson |
| 8,137,284 B2 | 3/2012 | Miles |
| 8,147,421 B2 | 4/2012 | Farquhar |
| 8,160,694 B2 | 4/2012 | Salmon |
| 8,192,437 B2 | 6/2012 | Simonson |
| 8,255,045 B2 | 8/2012 | Gharib |
| 8,295,933 B2 | 10/2012 | Gerber |
| D670,656 S | 11/2012 | Jepsen |
| 8,323,208 B2 | 12/2012 | Davis |
| 8,343,079 B2 | 1/2013 | Bartol |
| 8,374,673 B2 | 2/2013 | Adcox |
| RE44,049 E | 3/2013 | Herzon |
| 8,419,758 B2 | 4/2013 | Smith |
| 8,428,733 B2 | 4/2013 | Carlson |
| 8,457,734 B2 | 6/2013 | Libbus |
| 8,498,717 B2 | 7/2013 | Lee |
| 8,515,520 B2 | 8/2013 | Brunnett |
| 8,568,312 B2 | 10/2013 | Cusimano Reaston |
| 8,568,317 B1 | 10/2013 | Gharib |
| 8,594,779 B2 | 11/2013 | Denison |
| 8,670,830 B2 | 3/2014 | Carlson |
| 8,680,986 B2 | 3/2014 | Costantino |
| 8,688,237 B2 | 4/2014 | Stanislaus |
| 8,695,957 B2 | 4/2014 | Quintania |
| 8,740,783 B2 | 6/2014 | Gharib |
| 8,753,333 B2 | 6/2014 | Johnson |

(56) References Cited

U.S. PATENT DOCUMENTS

| | | |
|---|---|---|
| 8,764,654 B2 | 7/2014 | Chmiel |
| 8,805,527 B2 | 8/2014 | Mumford |
| 8,876,813 B2 | 11/2014 | Min |
| 8,886,280 B2 | 11/2014 | Kartush |
| 8,892,259 B2 | 11/2014 | Bartol |
| 8,926,509 B2 | 1/2015 | Magar |
| 8,942,797 B2 | 1/2015 | Bartol |
| 8,956,418 B2 | 2/2015 | Wasielewski |
| 8,958,869 B2 | 2/2015 | Kelleher |
| 8,971,983 B2 | 3/2015 | Gilmore |
| 8,986,301 B2 | 3/2015 | Wolf |
| 8,989,855 B2 | 3/2015 | Murphy |
| 9,031,658 B2 | 5/2015 | Chiao |
| 9,037,226 B2 | 5/2015 | Hacker |
| 9,078,671 B2 | 7/2015 | Beale |
| 9,084,550 B1 | 7/2015 | Bartol |
| 9,084,551 B2 | 7/2015 | Brunnett |
| 9,119,533 B2 | 9/2015 | Ghaffari |
| 9,121,423 B2 | 9/2015 | Sharpe |
| 9,149,188 B2 | 10/2015 | Eng |
| 9,155,503 B2 | 10/2015 | Cadwell |
| 9,204,830 B2 | 12/2015 | Zand |
| 9,247,952 B2 | 2/2016 | Bleich |
| 9,295,401 B2 | 3/2016 | Cadwell |
| 9,295,461 B2 | 3/2016 | Bojarski |
| 9,339,332 B2 | 5/2016 | Srivastava |
| 9,352,153 B2 | 5/2016 | Van Dijk |
| 9,370,654 B2 | 6/2016 | Scheiner |
| 9,579,503 B2 | 2/2017 | McKinney |
| 9,616,233 B2 | 4/2017 | Shi |
| 9,622,684 B2 | 4/2017 | Wybo |
| 9,714,350 B2 | 7/2017 | Hwang |
| 9,730,634 B2 | 8/2017 | Cadwell |
| 9,820,768 B2 | 11/2017 | Gee |
| 9,855,431 B2 | 1/2018 | Ternes |
| 9,913,594 B2 | 3/2018 | Li |
| 9,935,395 B1 | 4/2018 | Jepsen |
| 9,999,719 B2 | 6/2018 | Kitchen |
| 1,002,209 A1 | 7/2018 | Whitman |
| 1,003,946 A1 | 8/2018 | Cadwell |
| 1,003,991 A1 | 8/2018 | McFarlin |
| 1,009,234 A1 | 10/2018 | Engeberg |
| 1,015,479 A1 | 12/2018 | Sakai |
| 1,029,288 A1 | 5/2019 | Jepsen |
| 1,034,245 A1 | 7/2019 | Sterrantino |
| 1,034,986 A1 | 7/2019 | Sterrantino |
| 1,039,836 A1 | 9/2019 | Brown |
| 1,041,875 A1 | 9/2019 | Jepsen |
| 1,063,191 A1 | 4/2020 | McFarlin |
| 2001/0031916 A1 | 10/2001 | Bennett |
| 2001/0039949 A1 | 11/2001 | Loubser |
| 2001/0049524 A1 | 12/2001 | Morgan |
| 2001/0056280 A1 | 12/2001 | Underwood |
| 2002/0001995 A1 | 1/2002 | Lin |
| 2002/0001996 A1 | 1/2002 | Seki |
| 2002/0007129 A1 | 1/2002 | Marino |
| 2002/0007188 A1 | 1/2002 | Arambula |
| 2002/0055295 A1 | 5/2002 | Itai |
| 2002/0065481 A1 | 5/2002 | Cory |
| 2002/0072686 A1 | 6/2002 | Hoey |
| 2002/0095080 A1 | 7/2002 | Cory |
| 2002/0149384 A1 | 10/2002 | Reasoner |
| 2002/0161415 A1 | 10/2002 | Cohen |
| 2002/0183647 A1 | 12/2002 | Gozani |
| 2002/0193779 A1 | 12/2002 | Yamazaki |
| 2002/0193843 A1 | 12/2002 | Hill |
| 2002/0194934 A1 | 12/2002 | Taylor |
| 2003/0032966 A1 | 2/2003 | Foley |
| 2003/0045808 A1 | 3/2003 | Kaula |
| 2003/0078618 A1 | 4/2003 | Fey |
| 2003/0088185 A1 | 5/2003 | Prass |
| 2003/0105503 A1 | 6/2003 | Marino |
| 2003/0171747 A1 | 9/2003 | Kanehira |
| 2003/0199191 A1 | 10/2003 | Ward |
| 2003/0212335 A1 | 11/2003 | Huang |
| 2004/0019370 A1 | 1/2004 | Gliner |
| 2004/0034340 A1 | 2/2004 | Biscup |
| 2004/0068203 A1 | 4/2004 | Gellman |
| 2004/0135528 A1 | 7/2004 | Yasohara |
| 2004/0172114 A1 | 9/2004 | Hadzic |
| 2004/0199084 A1 | 10/2004 | Kelleher |
| 2004/0204628 A1 | 10/2004 | Rovegno |
| 2004/0225228 A1 | 11/2004 | Ferree |
| 2004/0229495 A1 | 11/2004 | Negishi |
| 2004/0230131 A1 | 11/2004 | Kassab |
| 2004/0260358 A1 | 12/2004 | Vaughan |
| 2005/0004593 A1 | 1/2005 | Simonson |
| 2005/0004623 A1 | 1/2005 | Miles |
| 2005/0075067 A1 | 4/2005 | Lawson |
| 2005/0075578 A1 | 4/2005 | Gharib |
| 2005/0080418 A1 | 4/2005 | Simonson |
| 2005/0085743 A1 | 4/2005 | Hacker |
| 2005/0119660 A1 | 6/2005 | Bourlion |
| 2005/0149143 A1 | 7/2005 | Libbus |
| 2005/0159659 A1 | 7/2005 | Sawan |
| 2005/0182454 A1 | 8/2005 | Gharib |
| 2005/0215993 A1 | 9/2005 | Phan |
| 2005/0256582 A1 | 11/2005 | Ferree |
| 2005/0261559 A1 | 11/2005 | Mumford |
| 2006/0004424 A1 | 1/2006 | Loeb |
| 2006/0009754 A1 | 1/2006 | Boese |
| 2006/0025702 A1 | 2/2006 | Sterrantino |
| 2006/0025703 A1 | 2/2006 | Miles |
| 2006/0052828 A1 | 3/2006 | Kim |
| 2006/0069315 A1 | 3/2006 | Miles |
| 2006/0085048 A1 | 4/2006 | Cory |
| 2006/0085049 A1 | 4/2006 | Cory |
| 2006/0122514 A1 | 6/2006 | Byrd |
| 2006/0173383 A1 | 8/2006 | Esteve |
| 2006/0200023 A1 | 9/2006 | Melkent |
| 2006/0241725 A1 | 10/2006 | Libbus |
| 2006/0258951 A1 | 11/2006 | Bleich |
| 2006/0264777 A1 | 11/2006 | Drew |
| 2006/0276702 A1 | 12/2006 | McGinnis |
| 2006/0292919 A1 | 12/2006 | Kruss |
| 2007/0016097 A1 | 1/2007 | Farquhar |
| 2007/0021682 A1 | 1/2007 | Gharib |
| 2007/0032841 A1 | 2/2007 | Urmey |
| 2007/0049962 A1 | 3/2007 | Marino |
| 2007/0097719 A1 | 5/2007 | Parramon |
| 2007/0184422 A1 | 8/2007 | Takahashi |
| 2007/0270918 A1 | 11/2007 | De Bel |
| 2007/0282217 A1 | 12/2007 | McGinnis |
| 2008/0015612 A1 | 1/2008 | Urmey |
| 2008/0027507 A1 | 1/2008 | Bijelic |
| 2008/0039914 A1 | 2/2008 | Cory |
| 2008/0058606 A1 | 3/2008 | Miles |
| 2008/0064976 A1 | 3/2008 | Kelleher |
| 2008/0065144 A1 | 3/2008 | Marino |
| 2008/0065178 A1 | 3/2008 | Kelleher |
| 2008/0071191 A1 | 3/2008 | Kelleher |
| 2008/0077198 A1 | 3/2008 | Webb |
| 2008/0082136 A1 | 4/2008 | Gaudiani |
| 2008/0097164 A1 | 4/2008 | Miles |
| 2008/0167574 A1 | 7/2008 | Farquhar |
| 2008/0183190 A1 | 7/2008 | Adcox |
| 2008/0183915 A1 | 7/2008 | Iima |
| 2008/0194970 A1 | 8/2008 | Steers |
| 2008/0214903 A1 | 9/2008 | Orbach |
| 2008/0218393 A1 | 9/2008 | Kuramochi |
| 2008/0254672 A1 | 10/2008 | Dennes |
| 2008/0269777 A1 | 10/2008 | Appenrodt |
| 2008/0281313 A1 | 11/2008 | Fagin |
| 2008/0300650 A1 | 12/2008 | Gerber |
| 2008/0306348 A1 | 12/2008 | Kuo |
| 2009/0018399 A1 | 1/2009 | Martinelli |
| 2009/0088660 A1 | 4/2009 | McMorrow |
| 2009/0105604 A1 | 4/2009 | Bertagnoli |
| 2009/0143797 A1 | 6/2009 | Smith |
| 2009/0177112 A1 | 7/2009 | Gharib |
| 2009/0182322 A1 | 7/2009 | D'Amelio |
| 2009/0197476 A1 | 8/2009 | Wallace |
| 2009/0204016 A1 | 8/2009 | Gharib |
| 2009/0209879 A1 | 8/2009 | Kaula |

(56) References Cited

U.S. PATENT DOCUMENTS

| | | |
|---|---|---|
| 2009/0221153 A1 | 9/2009 | Santangelo |
| 2009/0240117 A1 | 9/2009 | Chmiel |
| 2009/0259108 A1 | 10/2009 | Miles |
| 2009/0279767 A1 | 11/2009 | Kukuk |
| 2009/0299439 A1 | 12/2009 | Mire |
| 2010/0004949 A1 | 1/2010 | O'Brien |
| 2010/0036280 A1 | 2/2010 | Ballegaard |
| 2010/0036384 A1 | 2/2010 | Gorek |
| 2010/0049188 A1 | 2/2010 | Nelson |
| 2010/0106011 A1 | 4/2010 | Byrd |
| 2010/0152604 A1 | 6/2010 | Kaula |
| 2010/0152811 A1 | 6/2010 | Flaherty |
| 2010/0152812 A1 | 6/2010 | Flaherty |
| 2010/0160731 A1 | 6/2010 | Giovannini |
| 2010/0168561 A1 | 7/2010 | Anderson |
| 2010/0191311 A1 | 7/2010 | Scheiner |
| 2010/0286554 A1 | 11/2010 | Davis |
| 2010/0317989 A1 | 12/2010 | Gharib |
| 2011/0004207 A1* | 1/2011 | Wallace ............. A61B 17/1671 606/35 |
| 2011/0028860 A1 | 2/2011 | Chenaux |
| 2011/0071418 A1 | 3/2011 | Stellar |
| 2011/0082383 A1 | 4/2011 | Cory |
| 2011/0160731 A1 | 6/2011 | Bleich |
| 2011/0184308 A1 | 7/2011 | Kaula |
| 2011/0230734 A1 | 9/2011 | Fain |
| 2011/0230782 A1 | 9/2011 | Bartol |
| 2011/0245647 A1 | 10/2011 | Stanislaus |
| 2011/0270120 A1 | 11/2011 | McFarlin |
| 2011/0270121 A1 | 11/2011 | Johnson |
| 2011/0295579 A1 | 12/2011 | Tang |
| 2011/0313530 A1 | 12/2011 | Gharib |
| 2012/0004516 A1 | 1/2012 | Eng |
| 2012/0071784 A1 | 3/2012 | Melkent |
| 2012/0109000 A1 | 5/2012 | Kaula |
| 2012/0109004 A1* | 5/2012 | Cadwell ................ A61B 34/10 600/554 |
| 2012/0220891 A1 | 8/2012 | Kaula |
| 2012/0238893 A1 | 9/2012 | Farquhar |
| 2012/0245439 A1 | 9/2012 | Andre |
| 2012/0277780 A1 | 11/2012 | Smith |
| 2012/0296230 A1 | 11/2012 | Davis |
| 2013/0027186 A1 | 1/2013 | Cinbis |
| 2013/0030257 A1 | 1/2013 | Nakata |
| 2013/0090641 A1 | 4/2013 | McKinney |
| 2013/0245722 A1 | 9/2013 | Ternes |
| 2013/0261422 A1 | 10/2013 | Gilmore |
| 2013/0267874 A1 | 10/2013 | Marcotte |
| 2014/0058284 A1 | 2/2014 | Bartol |
| 2014/0073985 A1 | 3/2014 | Sakai |
| 2014/0074084 A1 | 3/2014 | Engeberg |
| 2014/0088463 A1 | 3/2014 | Wolf |
| 2014/0121555 A1 | 5/2014 | Scott |
| 2014/0275914 A1 | 9/2014 | Li |
| 2014/0275926 A1 | 9/2014 | Scott |
| 2014/0288389 A1 | 9/2014 | Gharib |
| 2014/0303452 A1 | 10/2014 | Ghaffari |
| 2015/0012066 A1 | 1/2015 | Underwood |
| 2015/0088029 A1 | 3/2015 | Wybo |
| 2015/0088030 A1 | 3/2015 | Taylor |
| 2015/0112325 A1 | 4/2015 | Whitman |
| 2015/0202395 A1 | 7/2015 | Fromentin |
| 2015/0238260 A1 | 8/2015 | Nau, Jr. |
| 2015/0250423 A1 | 9/2015 | Hacker |
| 2015/0311607 A1 | 10/2015 | Ding |
| 2015/0380511 A1 | 12/2015 | Irsigler |
| 2016/0000382 A1 | 1/2016 | Jain |
| 2016/0015299 A1 | 1/2016 | Chan |
| 2016/0038072 A1 | 2/2016 | Brown |
| 2016/0038073 A1 | 2/2016 | Brown |
| 2016/0038074 A1 | 2/2016 | Brown |
| 2016/0135834 A1 | 5/2016 | Bleich |
| 2016/0174861 A1 | 6/2016 | Cadwell |
| 2016/0199659 A1 | 7/2016 | Jiang |
| 2016/0235999 A1 | 8/2016 | Nuta |
| 2016/0262699 A1 | 9/2016 | Goldstone |
| 2016/0270679 A1 | 9/2016 | Mahon |
| 2016/0287112 A1 | 10/2016 | McFarlin |
| 2016/0287861 A1 | 10/2016 | McFarlin |
| 2016/0317053 A1 | 11/2016 | Srivastava |
| 2016/0339241 A1 | 11/2016 | Hargrove |
| 2017/0231508 A1 | 8/2017 | Edwards |
| 2017/0273592 A1 | 9/2017 | Sterrantino |
| 2018/0345004 A1 | 12/2018 | McFarlin |
| 2019/0350485 A1 | 11/2019 | Sterrantino |

FOREIGN PATENT DOCUMENTS

| | | |
|---|---|---|
| AU | 607977 B2 | 3/1991 |
| AU | 2005269287 A1 | 2/2006 |
| AU | 2006217448 A1 | 8/2006 |
| AU | 2003232111 B2 | 10/2008 |
| AU | 2004263152 B2 | 8/2009 |
| AU | 2005269287 B2 | 5/2011 |
| AU | 2008236665 B2 | 8/2013 |
| AU | 2012318436 A1 | 4/2014 |
| AU | 2016244152 A1 | 11/2017 |
| AU | 2016244152 B2 | 12/2018 |
| AU | 2019201702 A1 | 4/2019 |
| BR | 9604655 C1 | 12/1999 |
| BR | 0609144 A2 | 2/2010 |
| CA | 2144211 C | 5/2005 |
| CA | 2229391 C | 9/2005 |
| CA | 2574845 A1 | 2/2006 |
| CA | 2551185 C | 10/2007 |
| CA | 2662474 A1 | 3/2008 |
| CA | 285078 A1 | 4/2013 |
| CA | 2769658 C | 1/2016 |
| CA | 298163 A1 | 10/2016 |
| CN | 101018585 A | 8/2007 |
| CN | 100571811 C | 12/2009 |
| CN | 104066396 A | 9/2014 |
| CN | 103052424 B | 12/2015 |
| CN | 104080509 B | 9/2017 |
| CN | 104717996 B | 1/2018 |
| CN | 107666939 A | 2/2018 |
| CN | 111419179 A | 7/2020 |
| DE | 2753109 A1 | 6/1979 |
| DE | 2831313 A1 | 2/1980 |
| DE | 8803153 U1 | 6/1988 |
| DE | 3821219 C1 | 8/1989 |
| DE | 29510204 U1 | 8/1995 |
| DE | 19530869 A1 | 2/1997 |
| DE | 29908259 U1 | 7/1999 |
| DE | 19921279 C1 | 11/2000 |
| DE | 19618945 C2 | 2/2003 |
| EP | 0161895 A2 | 11/1985 |
| EP | 298268 | 1/1989 |
| EP | 0719113 A1 | 7/1996 |
| EP | 0759307 A2 | 2/1997 |
| EP | 0836514 A2 | 4/1998 |
| EP | 890341 | 1/1999 |
| EP | 972538 | 1/2000 |
| EP | 1656883 A1 | 5/2006 |
| EP | 1115338 B1 | 8/2006 |
| EP | 1804911 A1 | 7/2007 |
| EP | 1534130 A4 | 9/2008 |
| EP | 1804911 B1 | 1/2012 |
| EP | 2481338 A3 | 9/2012 |
| EP | 276361 A1 | 8/2014 |
| EP | 13854171 B1 | 4/2016 |
| EP | 1680177 B1 | 4/2017 |
| EP | 3277366 A1 | 2/2018 |
| ES | 2725489 T3 | 9/2019 |
| FI | 73878 C | 12/1987 |
| FR | 2624373 A1 | 6/1989 |
| FR | 2624748 B1 | 10/1995 |
| FR | 2796846 A1 | 2/2001 |
| FR | 2795624 B1 | 9/2001 |
| FR | 2835732 B1 | 11/2004 |
| GB | 1534162 A | 11/1978 |
| GB | 2049431 A | 12/1980 |
| GB | 2052994 A | 2/1981 |
| GB | 2452158 A | 2/2009 |

(56) References Cited

FOREIGN PATENT DOCUMENTS

| | | | |
|---|---|---|---|
| GB | 2519302 B | 4/2016 | |
| IT | 1221615 B | 7/1990 | |
| JP | H0723964 A | 1/1995 | |
| JP | 2000028717 A | 1/2000 | |
| JP | 3188437 B2 | 7/2001 | |
| JP | 2000590531 A | 8/2003 | |
| JP | 2003524452 A | 8/2003 | |
| JP | 2004522497 A | 7/2004 | |
| JP | 2008508049 A | 3/2008 | |
| JP | 4295086 B2 | 7/2009 | |
| JP | 4773377 B2 | 9/2011 | |
| JP | 4854900 B2 | 1/2012 | |
| JP | 4987709 B2 | 7/2012 | |
| JP | 5132310 B2 | 1/2013 | |
| JP | 2014117328 A | 6/2014 | |
| JP | 2014533135 A | 12/2014 | |
| JP | 6145916 B2 | 6/2017 | |
| JP | 2018514258 A | 6/2018 | |
| JP | 2018514258 A5 | 5/2019 | |
| JP | 6749338 B2 | 9/2020 | |
| KR | 100632980 B1 | 10/2006 | |
| KR | 102007010667 A | 11/2007 | |
| KR | 100877229 B1 | 1/2009 | |
| KR | 20140074973 A | 6/2014 | |
| KR | 1020170133499 A | 12/2017 | |
| KR | 102092583 B1 | 3/2020 | |
| KR | 1020200033979 A | 3/2020 | |
| NZ | 541889 A | 4/2010 | |
| SE | 467561 B | 8/1992 | |
| SE | 508357 C2 | 9/1998 | |
| WO | 1999037359 A1 | 7/1999 | |
| WO | 2000038574 A1 | 7/2000 | |
| WO | 2000066217 A1 | 11/2000 | |
| WO | 2001037728 A1 | 5/2001 | |
| WO | 2001078831 A2 | 10/2001 | |
| WO | 2001087154 A1 | 11/2001 | |
| WO | 2001093748 A2 | 12/2001 | |
| WO | 2002082982 A1 | 10/2002 | |
| WO | 2003005887 A2 | 1/2003 | |
| WO | 2003034922 A1 | 5/2003 | |
| WO | 2003094744 A1 | 11/2003 | |
| WO | 2004064632 A1 | 8/2004 | |
| WO | 2005030318 A1 | 4/2005 | |
| WO | 2006015069 A1 | 2/2006 | |
| WO | 2006026482 A2 | 3/2006 | |
| WO | 2006042241 A2 | 4/2006 | |
| WO | 2006113394 A2 | 10/2006 | |
| WO | 2008002917 A2 | 1/2008 | |
| WO | 2008005843 A2 | 1/2008 | |
| WO | 2008097407 A2 | 8/2008 | |
| WO | 2009051965 A1 | 4/2009 | |
| WO | 2010090835 A1 | 8/2010 | |
| WO | 2011014598 A1 | 2/2011 | |
| WO | 2011150502 A2 | 12/2011 | |
| WO | 2013019757 A2 | 2/2013 | |
| WO | 2013052815 A1 | 4/2013 | |
| WO | 2013151770 A1 | 10/2013 | |
| WO | 2015069962 A1 | 5/2015 | |
| WO | 2016160477 A1 | 10/2016 | |

OTHER PUBLICATIONS

Clements, et. al., "Evoked and Spontaneous Electromyography to Evaluate Lumbosacral Pedicle Screw Placement", 21 (5):600-604 (1996).

Danesh-Clough, et. al., "The Use of Evoked EMG in Detecting Misplaced Thoracolumbar Pedicle Screws", 26(12)1 313-1316 (2001).

Dezawa et al., "Retroperitoneal Laparoscopic Lateral Approach to the Lumbar Spine: A New Approach, Technique, and Clinical Trial", Journal of Spinal Disorders 13(2):138-143 (2000).

Dickman, et al., "Techniques in Neurosurgery", National Library of Medicine, 3 (4) 301-307 (1997).

Epstein, et al., "Evaluation of Intraoperative Somatosensory-Evoked Potential Monitoring During 100 Cervical Operations", 18(6):737-747 (1993), J.B. Lippincott Company.

Glassman, et. al., "A Prospective Analysis of Intraoperative Electromyographic Monitoring of Pedicle Screw Placement with Computed Tomographic Scan Confirmation", 20(12)1 375-1379.

Goldstein, et. al., "Minimally Invasive Endoscopic Surgery of the Lumbar Spine", Operative Techniques in Orthopaedics, 7 (1):27-35 (1997).

Greenblatt, et. al., "Needle Nerve Stimulator-Locator", 41 (5):599-602 (1962).

H.M. Mayer, "Minimally Invasive Spine Surgery, A Surgical Manual", Chapter 12, pp. 117-131 (2000).

Hinrichs, et al., "A trend-detection algorithm for intraoperative Eeg monitoring", Med. Eng. Phys. 18 (8):626-631 (1996).

Bergey et al., "Endoscopic Lateral Transpsoas Approach to the Lumbar Spine", SPINE 29 (15):1681-1688 (2004).

Holland, "Spine Update, Intraoperative Electromyography During Thoracolumbar Spinal Surgery", 23 (17):1915-1922 (1998).

Holland, et al., "Continuous Electromyographic Monitoring to Detect Nerve Root Injury During Thoracolumbar Scoliosis Surgery", 22 (21):2547-2550 (1997), Lippincott-Raven Publishers.

Hovey, A Guide to Motor Nerve Monitoring, pp. 1-31 Mar. 20, 1998, The Magstim Company Limited.

Kevin T. Foley, et. al., "Microendoscipic Discectomy" Techniques in Neurosurgery, 3:(4):301-307, © 1997 Lippincott-Raven Publishers, Philadelphia.

Kossmann et al., "The use of a retractor system (SynFrame) for open, minimal invasive reconstruction of the anterior col. Of the thoracic and lumbar spine", 10:396-402 (2001).

Kossmann, et. al., "Minimally Invasive Vertebral Replacement with Cages in Thoracic and Lumbar Spine", European Journal of Trauma, 2001, No. 6, pp. 292-300.

Lenke, et. al., "Triggered Electromyographic Threshold for Accuracy of Pedicle Screw Placement, An Animal Model and Clinical Correlation", 20 (14):1585-1591 (1995).

Lomanto et al., "7th World Congress of Endoscopic Surgery" Singapore, Jun. 1-4, 2000 Monduzzi Editore S.p. A.; email: monduzzi@monduzzi.com, pp. 97-103 and 105-111.

MaGuire, et. al., "Evaluation of Intrapedicular Screw Position Using Intraoperative Evoked Electromyography", 20 (9):1068-1074 (1995).

Mathews et al., "Laparoscopic Discectomy With Anterior Lumbar Interbody Fusion, A Preliminary Review", 20 (16):1797-1802, (1995), Lippincott-Raven Publishers.

Bertagnoli, et. al., "The AnteroLateral transPsoatic Approach (ALPA), A New Technique for Implanting Prosthetic Disc-Nucleus Devices", 16 (4):398-404 (2003).

Michael R. Isley, et. al., "Recent Advances in Intraoperative Neuromonitoring of Spinal Cord Function: Pedicle Screw Stimulation Techniques", Am. J. End Technol. 37:93-126 (1997).

Minahan, et. al., "The Effect of Neuromuscular Blockade on Pedicle Screw Stimulation Thresholds" 25(19):2526-2530 (2000).

Pimenta et. al., "Implante de prótese de núcleo pulposo: análise inicial", J Bras Neurocirurg 12 (2):93-96, (2001).

Raymond J. Gardocki, MD, "Tubular diskectomy minimizes collateral damage", AAOS Now, Sep. 2009 Issue, http://www.aaos.org/news/aaosnow/sep09/clinical12.asp.

Raymond, et. al., "The NerveSeeker: A System for Automated Nerve Localization", Regional Anesthesia 17:151-162 (1992).

Reidy, et. al., "Evaluation of electromyographic monitoring during insertion of thoracic pedicle screws", British Editorial Society of Bone and Joint Surgery 83 (7):1009-1014, (2001).

Rose et al., "Persistently Electrified Pedicle Stimulation Instruments in Spinal Instrumentation: Technique and Protocol Development", Spine: 22(3): 334-343 (1997).

Teresa Riordan "Patents; A businessman invents a device to give laparoscopic surgeons a better view of their worK", New York Times www.nytimes.com/2004/29/business/patents-businessman-invents-device-give-la (Mar. 2004).

Toleikis, et. al., "The usefulness of Electrical Stimulation for Assessing Pedicle Screw Placements", Journal of Spinal Disorders, 13 (4):283-289 (2000).

(56) References Cited

OTHER PUBLICATIONS

U.Schick, et. al., "Microendoscopic lumbar discectomy versus open surgery: an intraoperative EMG study", pp. 20-26, Published online: Jul. 31, 2001 © Springer-Verlag 2001.
Bose, et. al., "Neurophysiologic Monitoring of Spinal Nerve Root Function During Instrumented Posterior Lumbar Spine Surgery", 27 (13):1440-1450 (2002).
Vaccaro, et. al., "Principles and Practice of Spine Surgery", Mosby, Inc. © 2003, Chapter 21, pp. 275-281.
Vincent C. Traynelis, "Spinal arthroplasty", Neurosurg Focus 13 (2):1-7. Article 10, (2002).
Welch, et. al., "Evaluation with evoked and spontaneous electromyography during lumbar instrumentation: a prospective study", J Neurosurg 87:397-402, (1997).
Zouridakis, et. al., "A Concise Guide to Intraoperative Monitoring", Library of Congress card No. 00-046750, Chapter 3, p. 21, chapter 4, p. 58 and chapter 7 pp. 119-120.
Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.
Chapter 9, "Root Finding and Nonlinear Sets of Equations", Chapter 9:350-354, http://www.nr.com.
Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, For Percutaneous Stimulation of Nerve and Muscle Tissue".
Ford et al, Electrical characteristics of peripheral nerve stimulators, implications for nerve localization, Dept. of Anesthesia, University of Cincinnati College of Medicine, Cincinnati, OH 45267, pp. 73-77.
Deletis et al, "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.
Butterworth et. al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.
Calancie, et. al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).
Calancie, et. al., "Threshold-level repetitive transcranial electrical stimulation for intraoperative monitoring of central motor conduction", J. Neurosurg 95:161-168 (2001).
Calancie, et. al., Stimulus-Evoked EMG Monitoring During Transpedicular Lumbosacral Spine Instrumentation, Initial Clinical Results, 19 (24):2780-2786 (1994).
Carl T. Brighton, "Clinical Orthopaedics and Related Research", Clinical Orthopaedics and related research No. 384, pp. 82-100 (2001).
Cadwell et al. "Electrophysiologic Equipment and Electrical Safety" Chapter 2, Electrodiagnosis in Clinical Neurology, Fourth Edition; Churchill Livingstone, p. 15, 30-31; 1999.
Ott, "Noise Reduction Techniques in Electronic Systems" Second Edition; John Wiley & Sons, p. 62, 1988.
Stecker et al. "Strategies for minimizing 60 Hz pickup during evoked potential recording", Electroencephalography and clinical Neurophysiology 100 (1996) 370-373.
Wood et al. "Comparative analysis of power-line interference between two- or three-electrode biopotential amplifiers" Biomedical Engineering, Med. & Biol. Eng. & Comput., 1995, 33, 63-68.
Urmey "Using the nerve stimulator for peripheral or plexus nerve blocks" Minerva Anesthesiology 2006; 72:467-71.
Review of section 510(k) premarket notification for "K013215: NuVasive NeuroVision JJB System", Department of Health and Human Services, FDA, Oct 16, 2001.
International Search Report for PCT/US2016/023903, dated Sep. 6, 2016.
International Search Report for PCT/US2005/026692, dated Nov. 16, 2005.

* cited by examiner

SURGICAL INSTRUMENTS FOR DETERMINING A LOCATION OF A NERVE DURING A PROCEDURE

CROSS-REFERENCE TO RELATED APPLICATIONS

This application claims the benefit of U.S. Provisional Patent Application No. 61/792,339, filed Mar. 15, 2013, which is hereby incorporated by reference herein in its entirety.

BACKGROUND

The risk of injury to a nerve is a concern when performing surgical procedures, including minimally invasive procedures, within close proximity to the spine or spinal nerves. Surgeons increasingly rely on neuromonitoring techniques to monitor the nerves during such surgeries in order to avoid inadvertently injuring or contacting a nerve. Prior devices have been developed to help surgeons avoid contacting and damaging nerves during these procedures, but improvements are needed for enhancing the monitoring capabilities of those devices.

In some spinal surgeries, a patient's spine is accessed and viewed by anterior, posterior, or lateral approaches in which instruments for the surgery are advanced to the spine. When approaching the patient's spine, care must be taken to avoid nerves, in particular to avoid spinal nerves that exit the spinal cord at nerve roots extending through the spinal vertebrae. These spinal nerves include motor nerves, which control muscle activity throughout the body, and sensory nerves, which receive sensory input and relay the sensory input to the spinal cord and brain. During spinal surgeries, both motor and sensory nerves may be present in the muscle and tissue through which instruments are advanced to access the spine. Some techniques monitor muscle EMG responses during surgery to identify when a surgical tool is too close to a nerve. But those techniques do not address potential damage to sensory nerves, such as the genitofemoral nerve, that may also be near the surgical site. If damage to the nerves is not avoided, a patient may suffer post-surgery partial paralysis or pain resulting from the nerve damage.

SUMMARY

Disclosed herein are systems, devices and methods for neuromonitoring, particularly neuromonitoring to reduce the risks of contacting or damaging nerves or causing patient discomfort during and after surgical procedures, including spinal surgeries. The neuromonitoring procedures include monitoring for the presence of or damage to sensory nerves, and optionally includes additional monitoring for motor nerves. In some systems, including systems that monitor for both sensory and motor nerves, components of the monitoring systems (e.g., stimulating electrodes and response sensors), may be combined with one or more surgical instruments.

During a spinal surgical procedure, surgical instruments approaching the spine may encounter both sensory and motor nerves that exit the lateral sides of the spine. The motor nerve roots exiting the spine run to peripheral muscles and innervate those muscles to control both voluntary and involuntary contraction of the muscles. Nerve signals running through these motor nerves originate in the brain, pass through the spinal cord, and run through a particular peripheral nerve to the innervated muscle being controlled. Sensory nerves, on the other hand, relay sensory information from peripheral sensors, such as skin mechanoreceptors, to the spinal cord and the brain. Mixed nerves have both motor and sensory functions, with some fibers of the nerve innervating muscles and other fibers of the nerve relaying sensory information to the brain. The combination of the motor, sensory, and mixed nerves creates a two-way pathway of communication between the central nervous system (brain and spinal cord) and peripheral tissues. Signals in motor nerves or fibers travel in one direction from the brain to the periphery, while signals in sensory nerves or fibers travel in the opposite direction from the periphery to the brain. In monitoring for these nerves during any surgical procedure, the systems, devices, and methods disclosed herein may make use of this two-way pathway to stimulate and sense responses from both motor and sensory nerves or fibers, so as to detect sensitive nerve tissues and help guide surgical tools.

Motor nerves can be monitored by stimulating the nerves near or at the nerve root and monitoring peripheral muscles innervated by the nerves for muscle responses caused by the delivered stimulation. The stimulation may be delivered by applying any suitable stimulus signals, including voltage and/or current pulses of varying amplitude, pulse width, and/or frequency. With surgical instruments approaching the spine, stimulation may be delivered during the approach from a distal end of a surgical instrument, and peripheral muscles, for example muscles in the legs, can be monitored using EMG sensors to detect triggered responses from stimulated nerves. Stimulation may also be provided after establishing the operative corridor (e.g., after a surgical tool has advanced to the operative site). For vertebral pedicle integrity assessments, stimulation may be delivered before, during, and/or after the formation of a hole drilled to receive a pedicle screw, as well as before, during, and/or after the pedicle screw is introduced into the hole. When monitoring for changes in nerve pathology, stimulation may be performed before, during, and/or after contact with the nerve (e.g., before, during, and/or after retraction of the nerve root). The response of the nerve to the stimulation can be measured in any suitable fashion, such as by monitoring the evoked muscle action potential. For example, a sensed EMG signal of muscles associated with the nerve may be measured to indicate that a surgical instrument is approaching or impinging on the nerve and is used to warn a surgeon during the approach or at any time during or after the surgical procedure. Such neuromonitoring systems and methods may be, for example, similar to the systems and methods described in U.S. Provisional Application Nos. 61/721,482, 61/796,207, and 61/730,202, which are hereby fully incorporated by reference herein.

In contrast to motor nerves, sensory nerves do not innervate muscles and do not cause muscle reactions when roots of the nerves exiting the spine are stimulated, yet they are important to normal nervous system functions and should be avoided during surgery. Electrical stimulation delivered from a surgical instrument near the spine may not produce any detectable signal from the sensory nerves because the signals in those nerves are not amplified by muscle activity like signals in motor nerves. Thus, in order to detect the sensory nerves, in preferred embodiments stimulation causing a response from the nerves is delivered at the innervated peripheral tissue and detected near the nerve root exiting from the spine, as the nerve signal travels toward the spine and the brain. As with motor nerves, the stimulation may be provided using suitable stimulation signals, including by applying voltage and/or current pulses of varying amplitude, pulse width, and/or frequency. Just as a motor nerve, or motor fibers in a mixed nerve, innervates a known muscle or muscle group, sensory nerves innervate known sensory tissues in the periphery. Thus, by delivering a stimulus to a given sensory tissue, for example a skin dermatome, the system may monitor for a detectable electrical response near the spine, and the detected response can be processed by a processor or other computer component and attributed to the particular sensory nerve that is known to innervate the stimulated tissue. The detected response is caused by an action potential that propagates through the nerve towards the brain after the sensory stimulation is delivered. To detect the signal, a response sensor is positioned near the nerve between the nerve ending in the sensory tissue and the nerve ending in the brain. For example, sensors may be positioned near a branch of the peripheral nerve, near the nerve root exiting the spine, near the spinal cord, or on a patient's head near the brain. When the response signals are monitored for a plurality of stimulations (e.g., sequential stimulations), changes in the responses, such as changes in the amplitude, frequency, or latency of the responses, can signal a problem with the monitored nerve. By utilizing this sensory nerve detecting approach, sensory nerves that are not readily detectable by motor nerve EMG monitoring techniques may be detected.

In some implementations, neuromonitoring techniques described herein are employed before a surgical procedure is performed to assess and map a patient's nerve anatomy. Delivered stimulation and responses detected from sensory nerves, and also motor nerves in some approaches, are used to determine the distances from the nerves to probes located at different positions. The distances and positions are used to locate the nearby nerves and create a map of the nerve anatomy near the spine, or near a desired surgical site. A probe can be moved to multiple positions for different sequential assessments, or a tool including multiple probes can be used to perform the assessments simultaneously. For example, in certain embodiments, an instrument having multiple sensor probes is positioned near the spine and near the spinal nerves to detect responses in multiple locations. Each of the sensor probes is located at a different position in the general vicinity of the nerves, at different distances from the nerves. Each probe therefore elicits or receives different responses from the nerves, with respective signal strengths that differ according to the distance from the particular probe to the nerve. For example, a nerve response signal that is greater than a baseline signal by a pre-defined amount corresponds to a stimulation source positioned at a particular distance from the nerve. The known configuration of the probes relative to each other and the different responses elicited by the probes are then used to triangulate the location of the nerve relative to the probes. In systems that monitor both sensory and motor nerves, this neuromonitoring approach provides a map of the nervous anatomy, including both sensory and motor nerves, to provide a surgeon with a more complete map of the anatomy than is obtained by monitoring just one or the other of these two types of nerves.

Locating a nerve using multiple different locations of probes provides data to create a map of the nerve and the path it follows. After moving a probe with multiple sensors to a series of different positions and assessing nerve locations at each position, computer-implemented software processes the information obtained to map the nerve over the distance measured by the multiple locations in which the sensors are positioned. The map traces the nerve in three dimensions and provides a representation of the nerve anatomy that can be used either before, during, or after surgery to reduce the risk of damaging the nerve or assess nerve condition. If each of the probes positioned near the nerves incorporates components for both motor and sensory nerve monitoring, the resulting map can provide a full representation of both the motor and sensory nerves located around the surgical field.

A map of the nerve anatomy near a surgical field provides a helpful pre-surgical planning tool for a surgeon to plan the positioning of instruments for the surgery. As discussed below, the map allows positioning and approach planning to be performed before the actual surgical procedure begins and surgical instruments are advanced to the surgical site. Using the map, a surgeon can plan an approach path for advancing surgical instruments to the desired surgical field while reducing the risk of injuring surrounding nerves. The tools used in the surgery may still include stimulation and detection components for intraoperative monitoring, but the pre-surgical planning is used to further reduce the chance of those tools contacting nerves. In addition, the map may be used to position a probe, retractor, or other instrument in a stationary location known from the map to be near a sensory or motor nerve. The stationary instrument is then used to monitor the particular nerve throughout the surgery as other tools are moved around and used at the surgical site. Changes in the response of the monitored nerve are detected by the stationary instrument and flagged as potentially indicating, for example, impingement, compression, contact, or other injury to the nerve. The map can also be used during a surgical procedure to provide real-time information indicating the location of several nerves relative to a surgical instrument or to the surgical site. Similarly, the map can be used after surgery to provide an assessment of the impact of the surgical procedure on various characteristics of the nerve, such as change in neural physiology or position.

In some implementations, the neuromonitoring techniques described herein are employed during a surgical procedure to detect and guard nerves intraoperatively. For example, neuromonitoring is performed during a spinal surgery in which instruments are advanced to the patient's spine, including surgical approaches for establishing an operative corridor to an intervertebral target site. Such an approach may be used to establish a path to an operative site that is anterior, posterior, or on either side of the spine. For some surgeries, lateral approach may be preferred to gain access to the spine, for example, to access vertebral pedicles or intervertebral discs and to provide advantageous angles for insertion of pedicle screws. Instruments approaching the spine laterally must be advanced with caution, as sensitive nerve roots from the spinal cord exit the spine in lateral directions, and harm or unintentional stimulation of these nerves can cause pain or damage. In order to reduce unwanted contact with these nerves, neuromonitoring described herein may be used to determine the proximity of nerves and warn a surgeon if a surgical instrument is approaching too near to one or more of the nerve roots. By applying stimulus currents to or measuring responses from the nerves in the proximity of the instruments, such neuromonitoring techniques guide a surgeon through the tissue and to the spine without unintentionally contacting or damaging the nerves.

According to one aspect, a method of neuromonitoring includes the steps of delivering a first stimulus signal to a first stimulating electrode disposed at or near a dermatome innervated by a first nerve, receiving a nerve response signal detected by a response sensor disposed in tissue near the first nerve, determining a characteristic of the first nerve based on the nerve response signal, and communicating an indication of the characteristic to a user.

In some implementations, the stimulus is configured by delivering test stimulus signals to a plurality of stimulating electrodes disposed at or near the dermatome. The test stimulus signals may be delivered individually from each of the plurality of stimulating electrodes, and/or may be delivered from combinations of the plurality of stimulating electrodes. Test response signals are detected by the response sensor, and each response signal is associated with one or more of the plurality of stimulating electrodes. The test stimulus signals and test response signals are processed to automatically select stimulating electrodes for neuromonitoring. Processing the test stimulus signals and test response signals may include determining a response latency associated with each of the plurality of stimulating electrodes and/or determining a response amplitude associated with each of the plurality of stimulating electrodes. The method may include selecting stimulating electrodes having the largest response amplitudes.

In some implementations, the method includes synchronizing stimulus signals for the selected stimulating electrodes based on the determined response latencies. For synchronization, a stimulus signal is delivered from a first selected stimulating electrode having the longest response latency, stimulus signals delivered from subsequent selected stimulation electrodes having shorter response latencies are delayed. The stimulus signal delivered from each subsequent stimulation electrode is delayed by the difference between the longest response latency and a response latency associated with the subsequent stimulation electrode.

In some implementations, stimulus delivered from selected stimulation electrodes elicits a nerve response having a higher signal-to-noise ratio than nerve responses elicited by individual stimulation electrodes. The stimulus delivered from the selected stimulation electrodes may also elicit a compound action potential in the first nerve, and the stimulus may be delivered to more than one branch of the first nerve or to more than one dermatome innervated by the first nerve.

In some implementations, the method includes delivering a second stimulus signal to a second stimulating electrode disposed in tissue near a second nerve. A muscle response signal is received from a muscle sensor disposed in or near muscle tissue innervated by the second nerve. The muscle sensor may be placed on a skin surface near the muscle tissue innervated by the second nerve, or may be disposed within the muscle tissue. The second nerve is identified from data associating the muscle tissue with the second nerve. In some implementations, the method includes determining a characteristic of the second nerve based on the muscle response signal.

In some implementations, a surgical instrument is provided with the response sensor and the second stimulating electrode disposed on a distal end of the instrument. The surgical instrument is advanced towards a patient's spine prior to delivering the first stimulus signal. The surgical instrument may be one of a monopolar probe, a tissue dilator, a tissue retractor, a scalpel, a tool for implant placement, a pedicle screw, or a guide wire. The method may include toggling a neuromonitor coupled to the surgical instrument between a motor nerve stimulating state and a sensory nerve detecting state, and may include synchronizing stimulus signals delivered to the first and second stimulating electrodes. The synchronization is done based on latencies associated with the first and second nerves.

According to one aspect, a system for neuromonitoring includes a first stimulating electrode configured to deliver stimulation at or near a dermatome innervated by a first nerve, a nerve sensor configured to detect a nerve response in tissue near the first nerve, and a neuromonitor coupled to the first stimulating electrode and the nerve response sensor, the neuromonitor having processing circuitry. The processing circuitry is configured to deliver a first stimulus signal to the first stimulating electrode, receive a nerve response signal from the nerve sensor, determine a characteristic of the first nerve based on the nerve response signal, and communicate an indication of the characteristic to a user.

In some implementations, the first stimulating electrode and the nerve sensor communicate with the neuromonitor via a wired connection. In other implementations, the first stimulating electrode and the nerve sensor communicate with the neuromonitor via a wireless connection. There may be a plurality of stimulating electrodes coupled to the neuromonitor, and the plurality of stimulating electrodes may be in an electrode array. The processing circuitry is configured to deliver test stimulus signals to the plurality of stimulating electrodes. The processing circuitry may be configured to deliver the test stimulus signals individually to each of the plurality of stimulating electrodes, and/or may be configured to deliver the test stimulus signals to combinations of the plurality of stimulating electrodes. The nerve sensor is configured to detect test response signals associated with one or more of the plurality of stimulating electrodes. The processing circuitry is configured to automatically select stimulating electrodes for neuromonitoring from the test stimulus signals and test response signals.

In some implementations, the processing circuitry is configured to determine a response latency associated with each of the plurality of stimulating electrodes and is configured to determine a response amplitude associated with each of the plurality of stimulating electrodes. The processing circuitry is configured to select stimulating electrodes having the largest response amplitudes.

In some implementations, the processing circuitry is configured to synchronize stimulus signals for the selected stimulating electrodes based on the determined response latencies. The processing circuitry is configured to deliver a stimulus signal to a first selected stimulating electrode having the longest response latency and delay stimulus signals delivered to subsequent selected stimulation electrodes having shorter response latencies. The processing circuitry is configured to calculate the difference between the longest response latency and the response latency associated with each subsequent stimulation electrode, and is configured to delay stimulus signals delivered to each subsequent stimulation electrode by the calculated difference associated with the respective subsequent stimulation electrode.

In some implementations, the processing circuitry is configured to select a combination of stimulation electrodes that elicits a nerve response having a higher signal-to-noise ratio than nerve responses elicited by individual stimulation electrodes and/or is configured to select a combination of stimulation electrodes that elicits a compound action potential in the first nerve. In some implementations, the system includes a second stimulating electrode configured to deliver stimulation in tissue near a second nerve The processing circuitry is configured to deliver a second stimulus signal to the second stimulating electrode, and a muscle sensor configured to detect a muscle response signal in or near muscle tissue innervated by the second nerve. The muscle sensor comprises may be a needle electrode or a skin electrode. The processing circuitry is configured to identify the second nerve from data associating the muscle tissue with the second nerve, and the processing circuitry is configured to determine a characteristic of the second nerve based on the muscle response signal.

In some implementations, the system includes a surgical instrument, wherein the response sensor and the second stimulating electrode are disposed on a distal end of the instrument. The surgical instrument may be one of a monopolar probe, a tissue dilator, a tissue retractor, a scalpel, a tool for implant placement, a pedicle screw, or a guide wire. The neuromonitor is configured to toggle between a motor nerve stimulating state and a sensory nerve detecting state, and is configured to synchronize stimulus signals delivered to the first and second stimulating electrodes.

According to one aspect, a system for neuromonitoring includes means for delivering a first stimulus signal at or near a dermatome innervated by a first nerve, means for receiving a nerve response signal in tissue near the first nerve means for determining a characteristic of the first nerve based on the nerve response signal and means for communicating an indication of the characteristic to a user.

In some implementations, the system includes means for delivering test stimulus signals at or near the dermatome. The test stimulus signals may be delivered individually from each of a plurality of stimulating means, or may be delivered from combinations of stimulating means. The system includes means for receiving test response signals, wherein each response signal is associated with one or more stimulating means.

In some implementations, the system includes means for processing the test stimulus signals and test response signals to automatically select stimulating means for neuromonitoring. The system may also include means for determining a response latency associated with each of the plurality of stimulating means, and means for determining a response amplitude associated with each of the plurality of stimulating system. Means for selecting stimulating means having the largest response amplitudes are also provided. The system may include means for synchronizing stimulus signals for the selected stimulating means based on the determined response latencies, means for delivering a stimulus signal from a first selected stimulating means having the longest response latency, and means for delaying stimulus signals delivered from subsequent selected stimulation means having shorter response latencies. The stimulus signal delivered from each subsequent stimulation means is delayed by the difference between the longest response latency and a response latency associated with the subsequent stimulation means.

In some implementations, stimulus delivered from the selected stimulation electrodes elicits a nerve response having a higher signal-to-noise ratio than nerve responses elicited by individual stimulation electrodes, and stimulus delivered from the selected stimulation means may elicit a compound action potential in the first nerve, or may be delivered to more than one branch of the first nerve or to more than one dermatome innervated by the first nerve.

In some implementations, the system includes means for delivering a second stimulus signal to a second stimulating means disposed in tissue near a second nerve and means for receiving a muscle response signal detected by a muscle sensor means disposed in or near muscle tissue innervated by the second nerve. The muscle sensor means may be a skin surface placed near the muscle tissue innervated by the second nerve. The system includes means for identifying the second nerve from data associating the muscle tissue with the second nerve and means for determining a characteristic of the second nerve based on the muscle response signal.

In some implementations, the system includes an instrument means having the means for receiving a nerve response signal in tissue near the first nerve and the second stimulating means disposed on a distal end of the instrument means. A means for advancing the instrument means is provided to advance the instrument means towards a patient's spine prior to delivering the first stimulus signal. The instrument means may be one of a monopolar probe, a tissue dilator, a tissue retractor, a scalpel, a tool for implant placement, a pedicle screw, or a guide wire. In some implementations, the system includes means for toggling a neuromonitor coupled to the instrument means between a motor nerve stimulating state and a sensory nerve detecting state. and means for synchronizing stimulus signals delivered to the first and second stimulating means.

According to one aspect, a method of mapping nerve anatomy includes delivering stimulus to a first stimulating electrode disposed at or near a dermatome innervated by a first nerve, receiving a plurality of nerve response signals detected at response sensor positions in tissue near the first nerve, calculating a distance from each response sensor position to the first nerve determining, based on the calculated distances, a location of the first nerve, and plotting the determined location of the first nerve.

In some implementations, the method includes providing a probe having a response sensor disposed on a distal end of the probe, positioning the distal end of the probe at each of the response sensor positions in the tissue near the first nerve, and detecting a nerve response signal at the response sensor at each of the response sensor positions. A second stimulating electrode may also be disposed on the distal end of the probe.

In some implementations, the method includes providing a probe having a plurality of probe ends, each probe end having a response sensor, positioning the probe at a first probe position, wherein the plurality of probe ends are positioned at different response sensor positions when the probe is in a first probe position, and detecting a nerve response at each of the response sensors after stimulus is delivered to the first stimulating electrode. A distance is calculated from each probe end to the first nerve when the probe is positioned at the first probe position, and the distances calculated when the probe is positioned at the first probe position are processed to determine a first location of the first nerve. The probe is positioned at a second probe position, wherein each of the probe ends are positioned at different response sensor positions relative to the response sensor positions when the probe is in the first probe position. A nerve response is detected at each of the response sensors after stimulus is delivered to the first stimulating electrode, and a distance is calculated from each probe end to the first nerve when the probe is positioned at the second probe position. The distances calculated when the probe is positioned at the second probe position are processed to determine a second location of the first nerve. In some implementations, additional stimulating electrodes are provided, each additional stimulating electrode disposed on a respective one of the probe ends.

In some implementations, the method includes calculating distances from each response sensor position to the first nerve based on at least one of stimulation current, stimulation frequency, stimulation voltage, response amplitude, response latency, response frequency, and response direction. The method may also include calculating a direction from each response sensor position to the first nerve.

In some implementations, each determined location is associated with the first nerve. A location may be associated with the first nerve based on the stimulated dermatome, or may be associated with the first nerve based on user input or based on data stored in memory at a neuromonitor. The stored data may identify a relation between the first nerve and the first stimulating electrode, and/or the stored data may identify a relation between the stimulated dermatome and the first nerve.

In some implementations, the method includes storing a plurality of determined locations of the first nerve in memory at a neuromonitor and updating the stored locations with each subsequent location determined for the first nerve. The stored locations are plotted in a three-dimensional space, and the plot is displayed to a user.

According to one aspect, a system for mapping nerve anatomy includes a first stimulating electrode configured to deliver stimulation at or near a dermatome innervated by a first nerve, at least one response sensor configured to detect a nerve response at response sensor positions in the tissue near the first nerve, and a neuromonitor coupled to the first stimulating electrode and the at least one response sensor, the neuromonitor having processing circuitry. The processing circuitry is configured to calculate a distance from each response sensor position to the first nerve, determine, based on the calculated distances, a location of the first nerve, and plot the determined location of the first nerve.

In some implementations, the system includes a probe having a response sensor disposed on a distal end of the probe, and may include a second stimulating electrode disposed on the distal end of the probe.

In some implementations, the system includes a probe having a plurality of probe ends, each probe end having a response sensor. Each of the plurality of probe ends is positioned at a different response sensor positions when the probe is in a first probe position, and the response sensors are configured to detect a nerve response after stimulus is delivered to the first stimulating electrode. The processing circuitry is configured to calculate a distance from each probe end to the first nerve when the probe is positioned at the first probe position, and the processing circuitry is configured to determine a first location of the nerve based on the calculated distances. Each of the plurality of probe ends is positioned at a different response sensor position when the probe is positioned at a second probe position relative to the response sensor positions when the probe is in the first probe position, and the response sensors are configured to detect a nerve response after stimulus is delivered to the first stimulating electrode. The processing circuitry is configured to calculate a distance from each probe end to the first nerve when the probe is positioned at the second probe position. The processing circuitry is configured to determine a second location of the first nerve based on the distances calculated when the probe is positioned at the second probe position. In some implementations, the system includes additional stimulating electrodes, each additional stimulating electrode disposed on a respective one of the probe ends.

In some implementations, the processing circuitry is configured to calculate distances from each response sensor position to the first nerve based on at least one of stimulation current, stimulation frequency, stimulation voltage, response amplitude, response latency, response frequency, and response direction. The processing circuitry may also be configured to calculate a direction from each response sensor position to the first nerve. The processing circuitry is configured to associate each determined location with the first nerve. The processing circuitry may be configured to associate a location with the first nerve based on the stimulated dermatome, based on user input, and/or based on data stored in memory at the neuromonitor. The stored data identifies a relation between the first nerve and the first stimulating electrode or between the stimulated dermatome and the first nerve.

In some implementations, the neuromonitor is configured to store a plurality of determined locations of the first nerve in memory. The processing circuitry is configured to update the stored locations with each subsequent location determined for the first nerve and is configured to plot the stored locations in a three-dimensional space. The system may include a display configured to display a plot of the stored locations to the user.

According to one aspect, a system of mapping nerve anatomy includes means for delivering stimulus at or near a dermatome innervated by a first nerve, means for receiving a plurality of nerve response signals at response positions in tissue near the first nerve, means for calculating a distance from each response position to the first nerve, means for determining, based on the calculated distances, a location of the first nerve, and means for plotting the determined location of the first nerve.

In some implementations, the system includes probe means having a means for detecting a nerve response disposed on a distal end of the probe means. The system includes means for positioning the distal end of the probe means at each of the response positions in the tissue near the first nerve and means for detecting a nerve response signal at the means for detecting a nerve response at each of the response sensor positions. In some implementations, a second stimulating means is disposed on the distal end of the probe means.

In some implementations, the system includes a probe means having a plurality of probe ends, each probe end having a means for detecting a nerve response and means for positioning the probe means at a first probe position, wherein the plurality of probe ends are positioned at different response positions when the probe means is in a first probe position. The system includes means for detecting a nerve response at each of the response positions after stimulus is delivered to the first stimulating means. Means are provided for calculating a distance from each probe end to the first nerve when the probe means is positioned at the first probe position, and for processing the distances calculated when the probe means is positioned at the first probe position to determine a first location of the first nerve.

In some implementations, the system includes means for positioning the probe means at a second probe position, wherein each of the probe ends are positioned at different response positions relative to the response positions when the probe means is in the first probe position. Means are provided for detecting a nerve response at each of the response positions after stimulus is delivered to the first stimulating means, and for calculating a distance from each probe end to the first nerve when the probe means is positioned at the second probe position. Means for processing the distances calculated when the probe means is positioned at the second probe position are used to determine a second location of the first nerve. In some implementations, the system includes additional stimulating means, each additional stimulating means disposed on a respective one of the probe ends.

In some implementations, the system includes means for calculating distances from each response position to the first nerve based on at least one of stimulation current, stimulation frequency, stimulation voltage, response amplitude, response latency, response frequency, and response direction. The system may also include means for calculating a direction from each response position to the first nerve. The system includes means for associating each determined location with the first nerve, and may include means for associating a location with the first nerve based on the stimulated dermatome, based on user input, and/or based on data stored in memory at a neuromonitor. The stored data identifies a relation between the first nerve and the first stimulating means, and may identify a relation between the stimulated dermatome and the first nerve.

In some implementations, the system includes means for storing a plurality of determined locations of the first nerve in memory at a neuromonitor and means for updating the stored locations with each subsequent location determined for the first nerve. Means are provided for plotting the stored locations in a three-dimensional space, and the system may include means for displaying a plot of the stored locations to a user.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout.

DETAILED DESCRIPTION

Figure 1:
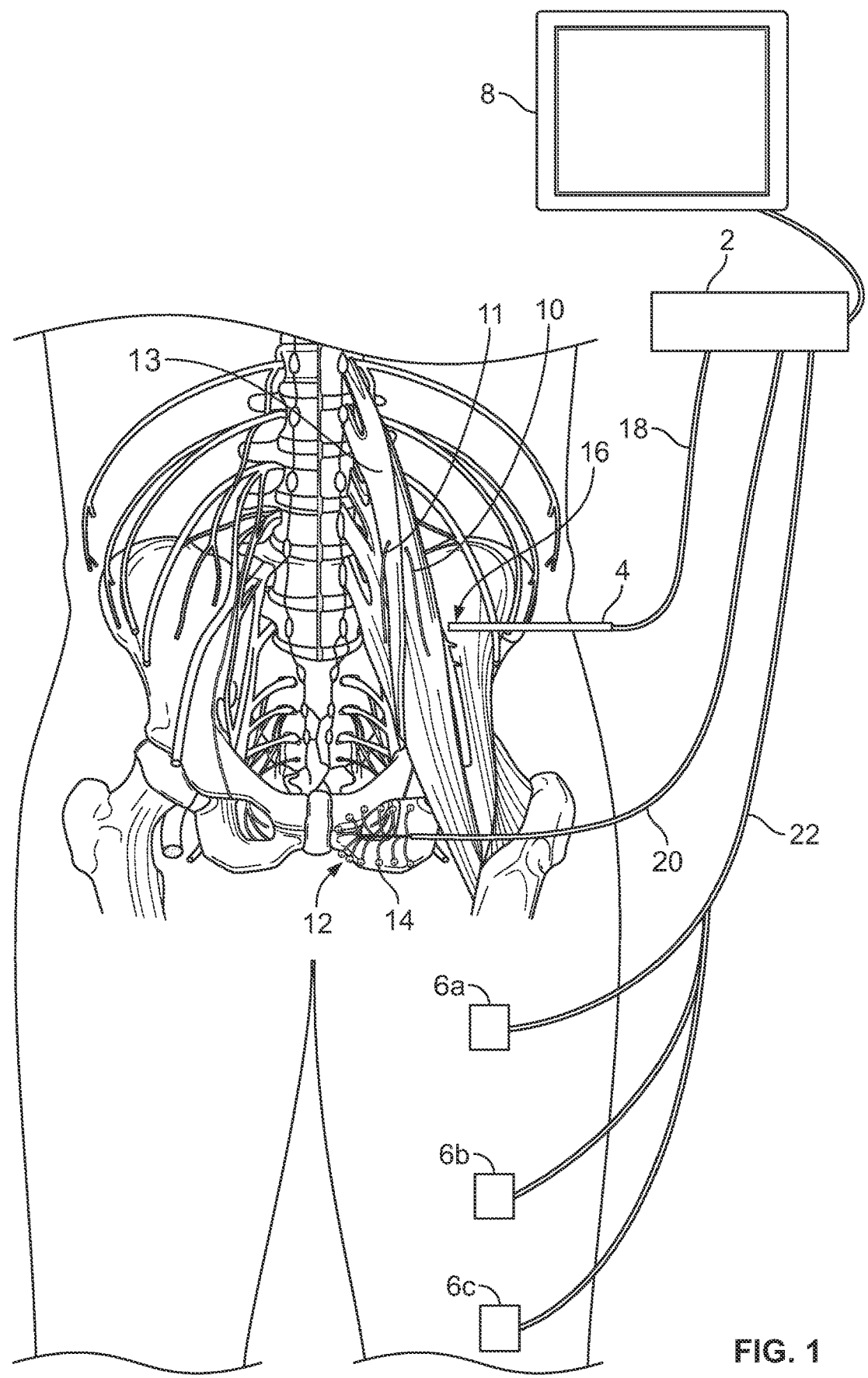
FIG. 1 shows a neuromonitoring system.

To provide an overall understanding of the systems, devices and methods disclosed herein, certain illustrative embodiments will be described. Although the embodiments and features described herein are specifically discussed for use in connection with spinal surgical procedures, it will be understood that the system components, connection mechanisms, surgical procedures, neuromonitoring, and other features outlined below may be combined with one another in any suitable manner and may be adapted and applied to systems to be used in other surgical procedures performed in the proximity of neural structures where nerve avoidance, detection, or mapping is desired, including but not limited to spine surgeries, brain surgeries, carotid endarterectomy, otolaryngology procedures such as acoustic neuroma resection, parotidectomy, nerve surgery, or any other surgical procedures in which nerve injury is possible and nerve preservation is desirable.

The systems, devices and methods disclosed herein relate to intraoperative neuromonitoring of evoked potential, transcranial electrical motor evoked potential, electromyography, and electroencephalogram signals. Intraoperative neuromonitoring reduces the risk of injury to neural structures during surgical procedures. Changes or abnormalities in the recording signals may indicate that the surgical procedure is affecting the neural structure being monitored. A monitoring system displays the electrical signals generated by one or more muscles, the central nervous system, and peripheral nerves and acquires the data necessary to perform intraoperative monitoring of neural pathways to prevent damage to neural structures during surgical procedures. It will be appreciated that the systems, devices and methods of the present disclosure can be adapted for use in pre- and post-operative procedures in addition to or in place of intraoperative procedures. In particular, the systems, methods, and devices described herein may be employed in any surgical procedure where pre-surgical planning, intraoperative monitoring, or post-operative evaluation of sensory or motor nerves would be beneficial, including, for example procedures that employ a lateral, posterior, or anterior approach to any portion of the thoracic or lumbar spine.

The neuromonitoring systems described herein provide pre-surgical planning and intraoperative monitoring by integrating neuromonitoring electrodes and sensors into the tools used during surgery and connecting those tools to electrical sources. Such tools may include tools used for approaching and creating a path to a surgical target, for example the spine. Approach tools may include scalpels, tissue dissection tools, guide wires, needles (e.g., needles having an insulated shaft and an exposed tip), dilators (including sequential dilation systems), retractors, working cannula, monopolar or bipolar probes, or any other surgical tools used to begin, create, or maintain a path to the surgical site. In some surgeries, the path to the surgical site is created and maintained using these surgical tools in sequence. For example, in some surgeries, an initial path is started using a scalpel or other tool for removing and cutting tissue near the skin surface. A guidewire is then advanced through the incision and, under the guidance of intraoperative imaging, advanced toward the surgical site to provide the path over which subsequent tools are advanced. Because it is the first tool advanced into deep tissue in some surgeries, providing neuromonitoring implements on the distal end of the guidewire may be preferable. Once the guidewire is placed, one or more dilators are advanced over the guidewire to widen the path through the tissue, and each sequential dilator may include neuromonitoring electrodes and sensors to protect neural tissue as the path is widened. Once the path is created, tissue retractors or working cannula are then used to maintain the path created by the dilators and provide access to the surgical site for the operation.

The electrodes and sensors used for neuromonitoring are provided on these tools to give early assessment and warnings as the tools are advanced into a patient's tissue. The tools are also used to provide intraoperative neuromonitoring during a surgery after the path to the surgical site is created. For example, working cannula, retractors, or stationary probes that hold tissue during surgery may monitor nearby nerve structures throughout the surgical procedure as other instruments are advanced to the surgical site and used. This provides ongoing monitoring after the initial path to the surgical site has been created, and can be used to monitor the neural structures while other instruments that may or may not include electrodes or sensors are used in the surgery.

In addition to guarding surrounding nerves from damage as tools are advanced to the spine and used in an operation, the surgical tools described herein include tools that provide intraoperative monitoring of the efficacy of a surgical procedure. Such tools include electrified probes, pedicle screws, pedicle screw placement tools, interbody implants, interbody implant placement tools, and any other tools that are used to carry out the procedure at the surgical site. These tools are used to evaluate the accuracy and efficacy of instrument placement, pedicle tapping, screw placement, pedicle integrity, interbody preparation, and interbody implant placement. The tools guard against complications that can arise when the surgical tools compromise the anatomical structures being operated on, for example when a drilling tool or screw compromises the wall of a tapped pedicle hole.

FIG. 1 shows an illustrative system for surgical neuromonitoring. During a surgical procedure, an instrument 4 is advanced towards a patient's spine from the lateral aspect of the patient's body while neuromonitoring is performed to detect and signal the presence of nerves in the patient's tissue as the instrument 4 is advanced deeper into the body. The instrument 4 may be any suitable electrified surgical instrument, for example a monopolar probe, a tissue dilator (which may be tubular or non-tubular), a tissue retractor, working cannula, a scalpel, a needle, a tool for implant placement, a pedicle screw, a guide wire, a sequential access surgical system including multiple instruments, or any other surgical instrument that may be used in spinal surgery. The instrument 4 can also provide nerve monitoring and detection after it is advanced to the surgical site, as may be the case with, for example, a pedicle probe used to drill or implant a pedicle screw at the site. When the instrument 4 is used to create an operative corridor, the instrument 4 may be directed through the psoas muscle during the procedure, although the instrument can also be used in approaches involving retraction of the psoas muscle using an electrified retractor, cannula, or other instruments.

One or more neuromonitoring components are disposed on the distal end 16 of the instrument 4. The components include response sensors (e.g., sensory electrodes) that sense nerve responses from nerves in the proximity of distal end 16 when those nerves are stimulated by stimulus signals delivered elsewhere, for example to sensory tissue. The response sensors detect electrical signals in the vicinity of the instrument 4. The sensors detect changes in the body's electrical potential in tissue surrounding the instrument 4, for example when a nerve in the vicinity of the instrument is stimulated and depolarizes. The depolarization of the nerve caused by a propagating nerve signal, or action potential, and subsequent repolarization of the nerve is detected by the response sensor and can be seen in a graph of the electrical potential detected by the instrument over time. As discussed below, the components on the distal end 16 may also include stimulating electrodes that deliver electrical signals to stimulate nerves in the proximity of the instrument 4, for example when the system is used to monitor both sensory and motor nerves.

During neuromonitoring, stimulations delivered to nerve responses are controlled and processed by the neuromonitor 2. The neuromonitor 2 preferably includes one or more suitable programmable processor-based devices (each having one or more processors) that include processing circuitry for controlling the neuromonitor and/or the surgical system.

The neuromonitor 2 may include stimulation circuitry (not shown), which may be embodied as a separate stimulation device connected to the neuromonitor 2 by a cable or wireless connection, or which may be embedded within the housing of neuromonitor 2. The stimulation circuitry works together with neuromonitor 2 to send stimulation signals to the one or more stimulation electrodes. The neuromonitor 2 also includes stimulation processing circuitry that controls the stimulation sources (e.g., by controlling the amplitude, duration, or frequency of stimulation signals). The stimulation circuitry (and/or neuromonitor 2) may include external controls that allow a user to start, stop, or adjust the stimulation signals. The neuromonitor 2 also includes response circuitry (not shown), which may be embodied as a separate response device connected to the neuromonitor 2 by a cable or wireless connection, or which may be embedded within the housing of neuromonitor 2. In preferred implementations, the response circuitry and the stimulation circuitry are located in the same device (e.g., in neuromonitor 2). The response circuitry receives digitized signals and other information from the stimulation circuitry indicative of the stimulations delivered to a patient, and (alone or in cooperation with neuromonitor 2) processes the received signals (which may be EMG, EEG, or other suitable signal) to extract characteristic information for each muscle group or nerve.

The neuromonitor 2 includes hardware and software platforms that control, send, receive, and process the stimulation signals, detected responses, and other communications during the neuromonitoring process. Included in the neuromonitor 2 is at least one processor or other circuitry that is configured with one or more algorithms for calibrating the neuromonitoring system, generating stimulus pulses, filtering signals, applying mathematical processes to analyze received signals, or performing other functions during the neuromonitoring process. These processes configure delivered stimulations, for example by selecting stimulating electrodes or timing stimulation pulses, control stimulating electrodes to deliver the stimulation pulses, filter signals from the electrodes and from response sensors, process one or more features of the stimulations and responses to analyze nerve anatomy, and communicate indications relating to the nerve anatomy. The neuromonitor 2 may receive user input, for example from a surgeon configuring the system, to control or change one or more of the functions carried out by the neuromonitor processing circuitry. To provide this processing power, the neuromonitor 2 may include one or more pieces of neuromonitoring equipment that act together to perform the neuromonitoring functions. For example, the neuromonitor 2 may include a Cadwell Cascade® neuromonitoring unit, or any other suitable neuromonitoring equipment made by Cadwell Laboratories, Inc.

Figure 15:
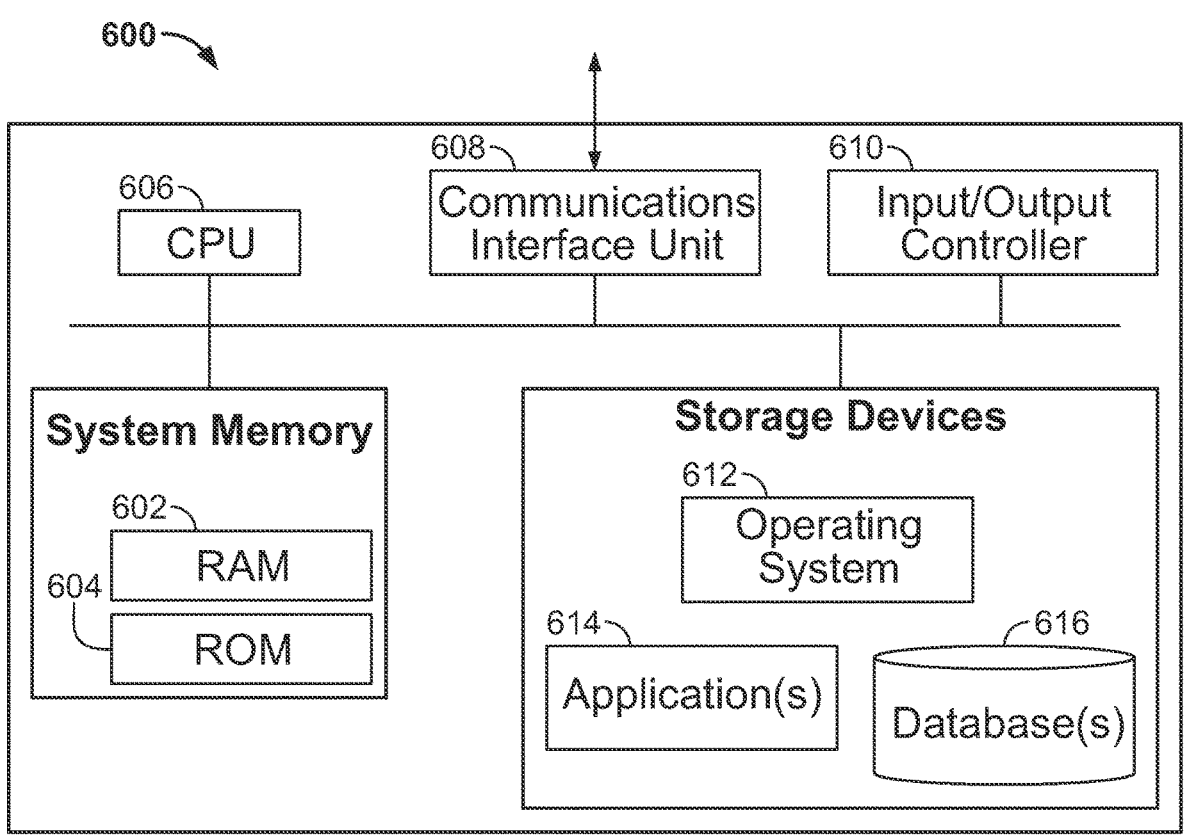
FIG. 15 shows a computing device.

FIG. 15 is a block diagram of a computing device 600, which may be a component of the neuromonitor 2 or any of the neuromonitors discussed herein, for performing any of the processes described herein. In certain implementations, a plurality of the components of these neuromonitoring systems may be included within one computing device 600. In certain implementations, components may be implemented across several computing devices 600.

The computing device 600 includes at least one communications interface unit, an input/output controller 610, system memory, and one or more data storage devices. The system memory includes at least one random access memory (RAM 602) and at least one read-only memory (ROM 604). All of these elements are in communication with a central processing unit (CPU 606) to facilitate the operation of the computing device 600. The computing device 600 may be configured in many different ways. For example, the computing device 600 may be a conventional standalone device or alternatively, the functions of computing device 600 may be distributed across multiple devices. In FIG. 15, the computing device 600 is linked, via network or local network, to other servers or devices.

The computing device 600 may be configured in a distributed architecture, wherein databases and processors are housed in separate units or locations. Some units perform primary processing functions and contain at a minimum a general controller or a processor and a system memory. In distributed architecture implementations, each of these units may be attached via the communications interface unit 608 to a communications hub or port (not shown) that serves as a primary communication link with other servers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 606 comprises a processor, such as one or more conventional microprocessors and one or more supplementary co-processors such as math co-processors for offloading workload from the CPU 606. The CPU 606 is in communication with the communications interface unit 608 and the input/output controller 610, through which the CPU 606 communicates with other devices such as other servers or neuromonitors. The communications interface unit 608 and the input/output controller 610 may include multiple communication channels for simultaneous communication with, for example, other processors, servers, neuromonitors, or other computing devices.

The CPU 606 is also in communication with the data storage device. The data storage device may comprise an appropriate combination of magnetic, optical or semiconductor memory, and may include, for example, RAM 602, ROM 604, flash drive, an optical disc such as a compact disc or a hard disk or drive. The CPU 606 and the data storage device each may be, for example, located entirely within a single neuromonitor or other computing device; or connected to each other by a communication medium, such as a USB port, serial port cable, a coaxial cable, an Ethernet cable, a telephone line, a radio frequency transceiver or other similar wireless or wired medium or combination of the foregoing. For example, the CPU 606 may be connected to the data storage device via the communications interface unit 608. The CPU 606 may be configured to perform one or more particular processing functions.

The data storage device may store, for example, (i) an operating system 612 for the computing device 600; (ii) one or more applications 614 (e.g., computer program code or a computer program product) adapted to direct the CPU 606 in accordance with the systems and methods described here; or (iii) database(s) 616 adapted to store information that may be utilized to store information required by the program.

The operating system 612 and applications 614 may be stored, for example, in a compressed, an uncompiled and an encrypted format, and may include computer program code. The instructions of the program may be read into a main memory of the processor from a computer-readable medium other than the data storage device, such as from the ROM 604 or from the RAM 602. While execution of sequences of instructions in the program causes the CPU 606 to perform the process steps described herein, hard-wired circuitry may be used in place of, or in combination with, software instructions for implementation of the processes of the present invention. Thus, the systems and methods described are not limited to any specific combination of hardware and software.

A neuromonitor may incorporate a "computer-readable medium," which refers to any non-transitory medium that provides or participates in providing instructions to the processor of the computing device 600 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 606 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 600 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

The neuromonitor 2 may incorporate any one or more of the hardware and software components described above with respect to computing device 600. These components provide processing logic in the neuromonitor that controls stimulations, processes responses, and carries out nerve detection using the surgical instrument 4. The instrument 4 is coupled to the neuromonitor 2 by a wired connection 18. In alternative embodiments, a wireless neuromonitor and wireless surgical instrument are used instead of the wired connection 18. The neuromonitor 2 controls stimulation and monitors nerve response detection and processing for the system shown in FIG. 1. In particular, the neuromonitor 2 controls the delivery of stimulus signals to stimulating electrodes in contact with the patient's body and receives detected signals from response sensors on the instrument 4 or from other sensors. The neuromonitor 2 controls the stimulation and processes the received response signals in order to determine characteristics of nerves in the vicinity of the distal end 16 of the instrument 4. The nerve characteristics monitored by the neuromonitor 2 may include one or more of the distance between the instrument and the nerve, the direction from the instrument to the nerve, the amplitude of the nerve response, the latency of the nerve response, nerve integrity, nerve location, or any other suitable characteristic. For some determinations, for example calculating distance to a nerve, the processor of the neuromonitor 2 is programmed to calculate the particular characteristic from the stimulus delivered, the nerve response detected, or both.

The neuromonitor 2 outputs determined information to a surgical display 8. The surgical display 8 provides a surgeon with indications of the characteristics derived from the detected signals received by the neuromonitor 2 to guide surgery. This information may be a display of raw signal, such as an EMG signal, an indication of nerve proximity, an indication of nerve integrity, an indication of nerve direction, an indication of the position of the surgical instrument 4, or any other suitable characteristics determined from the delivered stimulation and the detected nerve responses, including indicating within which of several ranges the detected value for each of these parameters may fall. Although one neuromonitor 2 is shown in FIG. 1 for ease of discussion, the neuromonitor 2 may include multiple neuromonitor apparatus working together in a centralized or decentralized fashion, including units that may be located remotely from the surgical site. For example, a first neuromonitor located within physical proximity of the surgical site may be used to provide stimulation signals to the neuromonitoring components and to receive responses from the response sensors. The responses may be transmitted over a wireless and/or wired link to a second neuromonitor that processes the responses and provides feedback to one or more clinicians or monitorists associated with the surgical procedure via one or more communication outputs, such as surgical display 8.

The display 8 communicates neuromonitoring information to the surgeon to operator (e.g., a surgeon or a monitorist). The display unit is equipped with a graphical user interface for providing information regarding any of the monitored characteristics visually to the operator. In addition or in the alternative, the display 8 controls audio components to communicate information audibly to the user, such as by changing the pitch or volume of an audio output based on whether the characteristic is within safe zones or warning zones. In some embodiments, the display 8 provides an alarm to warn the operator of potential injury to the nerve. The information may be provided in any suitable manner to the surgeon, including displaying indicators or warnings on the screen, displaying sensor signals, displaying electrode stimulus profiles, identifying the sensory or motor nerves monitored based on the sensory tissue stimulated or the muscle response detected, providing alphanumeric indicators of one or more nerve characteristics, displaying graphical indications of instrument or nerve location, and displaying a neural map, which may include an anatomical representation of the human form. The information and indicators may be color-coded, for example to differentiate a safe reading or circumstance from one that is potentially harmful to the patient. For example, when a threshold stimulation current is determined for a nerve in the vicinity of the surgical tool, the display 8 may provide an indication to the surgeon of the determined threshold that is color-coded based on a range that the threshold falls within. Such ranges may include preset or surgeon-manipulated safe and unsafe ranges of currents. The display 8 may be a touch-based communication interface capable of receiving input from the operator and providing the input to the neuromonitor 2. Only one display 8 is shown in FIG. 1. However, in some implementations, the system includes multiple displays (up to 2, up to 3, up to 5, up to 10, or up to 100) for simultaneously providing information to various users. One or more of the multi-display systems and methods discussed therein may be used in combination with any of the systems and methods described herein, including for displaying characteristics associated with sensory nerves. The display may include multiple displays, and may portray indications and information of sensory and motor nerve status similar to those discussed with respect to motor nerve monitoring in U.S. Provisional Application Nos. 61/721,482, 61/796,207, and 61/730,202, which are hereby fully incorporated by reference herein.

In some implementations, the instrument 4 is a multiple-probe instrument used to analyze and map the nerve anatomy before surgery. In such implementations, the display 8 provides the mapped anatomy to the surgeon. The data used to create the map is obtained by positioning the instrument 4 in multiple positions to determine multiple locations of the mapped nerves. The display 8 may display the developing map to the surgeon as a nerve location is added at each position of the instrument 4. The surgeon can use the developing map to position the probes for subsequent data acquisition in areas of the nerve that are not yet mapped. The finished map is then used to plan a surgical approach and/or is displayed to guide the surgeon when instruments are advanced to and used at the surgical site during the procedure. In addition to showing the developed map of the anatomy, the display 8 may overlay an approach path planned during the pre-surgical planning to guide the angles and depths at which the surgeon advances various instruments. The map on the display 8 may also be used to position probes near individual nerves for intraoperative monitoring. The display 8 may also track and display the position of the surgical tools relative to the mapped nerves intraoperatively, providing a single view of the mapped nerves and tool positioning to orient the surgeon.

During intraoperative neuromonitoring after the surgical procedure begins, the instrument 4 is used to monitor and detect locations and changes in conditions of sensory nerves, and the sensory nerves monitored may include the genitofemoral nerve shown in FIG. 1. The genitofemoral nerve has two main branches that pass through the psoas major muscle 13 on the lateral side of the spine. The main branches include a lateral femoral branch 10 and a medial genital branch 11. During a lateral surgical approach, the instrument 4 is advanced towards the patient's spine from a lateral insertion point and is at risk of compressing or damaging the two branches 10 and 11. In order to warn a surgeon and reduce the risk of causing such damage, the instrument 4 monitors for nerves as it is advanced by detecting nerve responses from sensory nerves in the vicinity of the instrument.

Because the genitofemoral nerve is a sensory nerve, and not a mixed nerve or motor nerve, the instrument 4 does not monitor for the branches 10 and 11 by delivering stimulus near the nerve and detecting elicited EMG responses, as is done in some motor nerve monitoring approaches. Instead, stimulation is delivered at peripheral locations (either on the patient's skin or by use of subdermal needles or probes) where one or both of the branches 10 and 11 innervate a dermatome near the surface of the skin, for example near the patient's thigh. The system then monitors a response by detecting fluctuations in body potential near an instrument at the spine that signal an action potential propagating in a nearby sensory nerve. In addition to positioning instruments at the spine, a sensory nerve monitoring system may detect the propagating action potential at any point between the stimulated tissue and the brain. For example, the action potential may be sensed by a probe positioned between the spine and the stimulated tissue, near the nerve root exiting the spine, near the spinal cord, at the brain, or on the patient's head.

The stimulation that elicits the detected sensory nerve response is delivered by the electrode array 12 shown connected to the neuromonitor 2 by the connection 20. While the array 12 is shown with a wired connection, as with the instrument 4, the electrode array 12 may operate wirelessly and communicate with the neuromonitor 2 over a wireless connection. When the array 12 is placed on a dermatome innervated by the branches 10 or 11, the delivery of electrical signals to the patient through one or more of the individual stimulating electrodes 14 in the array 12 triggers a sensory response from the corresponding branch 10 or 11 of the genitofemoral nerve. This stimulation causes an electrical signal to propagate from the dermatome through the corresponding branch 10 or 11 to the spinal cord and then to the patient's brain. In order to monitor for the genitofemoral nerve and detect the proximity of the instrument 4 to the nerve, one or more of the sensors on the distal end 16 of instrument 4 senses an electrical response from the genitofemoral nerve when the instrument is at or near one of the branches 10 or 11. The electrical response of the nerve is measured as an action potential by the sensors on the instrument 4. The measured potential is the result of the nerve depolarizing and repolarizing as the triggered nerve signal propagates through the nerve from the sensory tissue towards the brain.

The precise location of the dermatome innervated by the genitofemoral nerve and the nerve endings that innervate the dermatome may vary from patient to patient and may not be known for a particular patient. To provide customizable delivery of stimulation to the innervated dermatome, a plurality of the stimulating electrodes 14 are included in the array 12 to allow multiple electrode configuration options for delivering stimulation. For example, any one of the electrodes 14 may be selected to deliver the stimulation to the dermatome, or a combination of the electrodes 14 may be selected by the neuromonitor 2, or by a surgeon, to deliver the stimulation. The exact combination and location of the electrodes 14 used to deliver the stimulation can be selected through calibration of the system, and the neuromonitor 2 can be programmed to select the combination in an initial stimulation test. In such a stimulation test, the neuromonitor 2 causes multiple combinations of the electrodes 14 in the array 12 deliver test stimulus signals. Sensors on the distal end 16 of the instrument 4 monitor for nerve responses, and once nerve responses are received for multiple combinations of the electrodes 14, the neuromonitor 2 processes the responses and selects the combination that creates the clearest nerve response for stimulation during further neuromonitoring.

The neuromonitor 2 selects the combination of stimulating electrodes 14 used to deliver stimulation in order to produce a large, detectable response from the sensory nerves that are monitored. Selecting a certain combination of electrodes, and configuring the timing of the stimulation delivered from each, can create a compound action potential within the monitored sensory nerve that produces a more easily detected response than stimulation delivered from any one individual electrode. Stimulation from each individual electrode may elicit a nerve response from a monitored nerve that has a different amplitude or reaches a sensory probe upstream near the nerve at a slightly different timing than stimulation delivered from the other electrodes. The electrodes that elicit the strongest responses are selected for monitoring, and the timing of stimulation delivered from those electrodes is adjusted to coordinate the arrival of the action potential responses at the stimulus probe. The resulting aggregate of the individual responses, or compound action potential, produces a greater electrical signal for detecting than any of the individual electrodes produces. Timing approaches are discussed in further detail below with respect to FIGS. 8-11.

In addition to timing signals and creating a compound action potential, stimulation from multiple electrodes 14 in the array 12 can improve the detectability of signals by stimulating different branches of a nerve, or stimulating different dermatomes innervated by the nerve. Nerve endings include many fibers that innervate tissue, for example a sensory dermatome. Stimulating different areas of that tissue can stimulate different branches of the nerve ending. The stimulation of multiple nerve branches creates multiple small nerve responses in the branches that aggregate to form a larger response signal that propagates through the nerve, producing a larger detectable signal at an upstream response sensor. Similarly, nerves that innervate more than one sensory tissue, like the genitofemoral nerve, produce a larger aggregate response signal when more than one of the innervated tissues is stimulated. In addition to selecting multiple electrodes for stimulation, as discussed below, the stimulation provided to multiple nerve branches or multiple dermatomes of a nerve can be timed to create an aggregate signal that reaches the probe at the same time.

The nerve signal produced by stimulation provided at more than one electrode may also be amplified by creating a current density between electrodes that stimulates the main branch of the sensory nerve within the tissue, rather than stimulating only endings of the nerve. The location of the electrodes, and the intensity of the stimulation delivered to stimulate the main branch, will likely vary from nerve to nerve and patient to patient. To stimulate the main branch, two or more electrodes are positioned spaced apart such that the main branch is positioned within the tissue between the electrodes. When stimulation is delivered at the electrodes, a current density is created between the locations of the electrodes. If the current density is great enough, the nerve branch between the electrodes is triggered by the density between them, and the resulting signal that propagates through the nerve is larger than a compound action potential created by stimulating nerve endings at each of the electrodes individually. The stimulation delivered from each electrode may need to be increased, for example to double, three times, four times, five times, or more, in order to create adequate current density to reach and stimulate the nerve branch. The resulting nerve signal, however, may exhibit a similar amplification to double, three times, four times, five times, or more, relative to the compound action potential created when each electrode is stimulated at a lower level. The resulting larger signal may exhibit a greater signal-to-noise ratio, or may reduce latency problems that can result when different nerve endings are stimulated. Because the current density stimulates the nerve branch itself, and not multiple endings of the branch, the larger signal is a single propagating signal rather than a compound action potential that is timed up by synchronizing electrode stimulation timing.

Using multiple electrodes and properly timing their stimulations can reduce interference from noise in detected nerve responses. When only one electrode is used to deliver stimulation or only one branch of a nerve is stimulated, the resulting nerve response may be susceptible to noise interference caused by the delivered stimulation or other external interference sources. Whereas a single signal triggered from one individual electrode may have a low signal-to-noise ratio, the ratio can be decreased by each electrode or stimulated nerve branch contributing to the propagating signal. Timed stimulation from the electrodes that produce the strongest nerve responses from multiple branches of the stimulated nerve provides signals having preferable signal-to-noise ratio.

The system shown in FIG. 1 may monitor for sensory nerves and responses only. Using such a system, a surgeon can avoid pure sensory nerves, such as the genitofemoral nerve, as well as mixed nerves that include some sensory nerve fibers. The sensory system may be employed in a surgery in tandem with a second neuromonitoring system that monitors for motor nerves, and the two systems together may provide guidance to a surgeon in avoiding sensory, motor, and mixed nerves. In some implementations, the neuromonitoring system shown in FIG. 1 may incorporate motor monitoring components into the neuromonitor 2 in order to monitor for all three types of nerves without the need for a second neuromonitoring unit. The combined neuromonitoring system, under the control of neuromonitor 2, delivers stimulation to and detects responses from both motor and sensory nerve tissues with one system, thus providing full monitoring of the nervous anatomy.

While the combination of stimulation delivered from the array 12 and detection of nerve responses at the instrument 4 monitors and detects sensory nerves near the spine, the stimulation from array 12 does not produce a measurable response from motor nerves exiting the spine in the proximity of the distal end 16 of the instrument 4. In order to monitor for both sensory and motor nerves, the instrument 4 may be configured with multiple electrodes that serve a dual purpose—acting as both a nerve sensor (for sensory nerves) and a nerve stimulator (for motor nerves). Similarly, the sensor array 12 may also serve a dual purpose, having both nerve stimulating electrodes (for sensory nerves) and EMG response sensors (for motor nerves). Examples of motor nerve stimulating and detecting components and approaches are discussed in U.S. Provisional Application Nos. 61/721,482, 61/796,207, and 61/730,202, which are hereby fully incorporated by reference herein.

In addition to the sensors that detect nerve responses from sensory nerves, such as the two branches 10 and 11 of the genitofemoral nerve, the distal end 16 of the instrument 4 may include one or more stimulating electrodes that are controlled by the neuromonitor 2 to emit stimulus signals. These stimulus signals cause motor nerves in the proximity of the distal end 16 to depolarize and trigger a muscle contraction response in peripheral muscles innervated by the motor nerves. The inclusion of stimulating electrodes allows the instrument 4 to stimulate nearby motor nerves while still detecting (in timing offset from the delivered stimulus) the responses of sensory nerves located in the same area. Muscle responses elicited by the stimulation delivered from instrument 4 are detected by electrodes placed on the patient's skin over the muscle groups innervated by the motor nerves or embedded in the muscle tissue. For example, the system may include electrodes 6a-c, which may be surface EMG electrodes that pick up electrical muscle activity when one or more of the muscles beneath the skin is stimulated. These muscle responses are passed to the neuromonitor 2 through the connection 22 and are processed by the neuromonitor 2 to determine when a muscle response has been evoked by stimulus delivered by the instrument 4. Though the electrodes 6a-c are shown with a wired connection in FIG. 1, these electrodes, like the other components in the system, may communicate with the neuromonitor 2 via a wireless communications link.

The neuromonitoring components located on the instrument 4 provide the dual functions of the instrument—to act as both a nerve stimulator and a nerve response sensor. For motor nerve monitoring, the stimulating electrodes on instrument 4 deliver electrical stimulus to the tissue near spinal nerves to trigger neuromuscular responses from motor nerves. Such electrodes include monopolar and bipolar electrodes that are electrified on the instrument 4 and emit electrical signals into surrounding tissue when neuromonitor 2 initiates stimulation. For sensory nerve monitoring, the response sensors on instrument 4 sense body potentials in the tissues surrounding the instrument 4. When a sensory nerve near the instrument is stimulated, a propagating action potential is detected by the response sensors as a deviation from resting body potential caused by depolarization and repolarization of the nerve. The neuromonitor 2 serves as the controlling logic instrument for both the motor and sensory nerve detection systems. For example, a processor or control circuitry in the neuromonitor 2 is programmed or otherwise configured to execute algorithms and perform one or more of the functions that deliver stimulation, receive signals, process information, or perform communications within the system. In particular, when both response sensors and stimulating electrodes are placed on the instrument 4, the neuromonitor 2 times delivery of stimulus from the stimulation electrodes and detection of sensory responses at the response sensors such that the two systems do not interfere with each other. Because both the motor nerve stimulators and sensory nerve response sensors are placed near each other at the end of the instrument 4, the timing and synchronization of neuromonitor 2 reduces cross-talk and interference between the two types of nerve monitoring approaches.

In implementations in which instrument 4 acts as both a nerve stimulator and a nerve response sensor, the system can detect both sensory and motor nerves in the vicinity of the spine. The stimulation and sensing for both motor and sensory nerves performed by the electrodes and sensors on the instrument 4, the electrode array 12, and the sensors 6a-c are all controlled and synchronized by the neuromonitor 2 to reduce mixing signals or creating false electrical responses from the two stimulation and sensing components. For example, the stimulation delivered from the array 12 and the corresponding nerve response detected by a response sensor on the instrument 4 can be timed to sync with the motor nerve stimulus delivered from the instrument 4 and the corresponding muscle responses at the sensors 6a-c. In this way, motor nerve stimulation delivered from the instrument 4 does not interfere with sensory nerve response detection at the instrument 4, and stimulation from the array 12 does not cause false positive responses to be detected at the sensors 6a-c. Synchronization of the stimulation and response detection for both motor and sensory nerves is described in more detail below with respect to FIG. 11.

Sensory probes, such as instrument 4 and/or one or more peripheral electrodes (e.g., one or more of electrodes 6a-c in FIG. 1, can also be used to create a detailed map representative of the nerve anatomy around a surgical site prior to beginning a surgical procedure. As described above, in implementations in which the instrument combines a motor nerve stimulator and a sensory nerve response sensor, the system obtains electrical signals that can be used to determine the location of nerves and create maps of both sensory and motor nerve locations. When multiple probes are provided, or instrument 4 includes multiple branches that analyze adjacent tissue locations, the neuromonitor 2 can execute a combined sensory and motor nerve detection algorithm to create the nerve map with both types of nerves. The surgeon can then plan a surgical approach and procedure that takes into account both types of nerves using a single map. Detecting nerve locations and mapping sensory and motor nerves is described in more detail below with respect to FIGS. 12-14.

Figure 2:
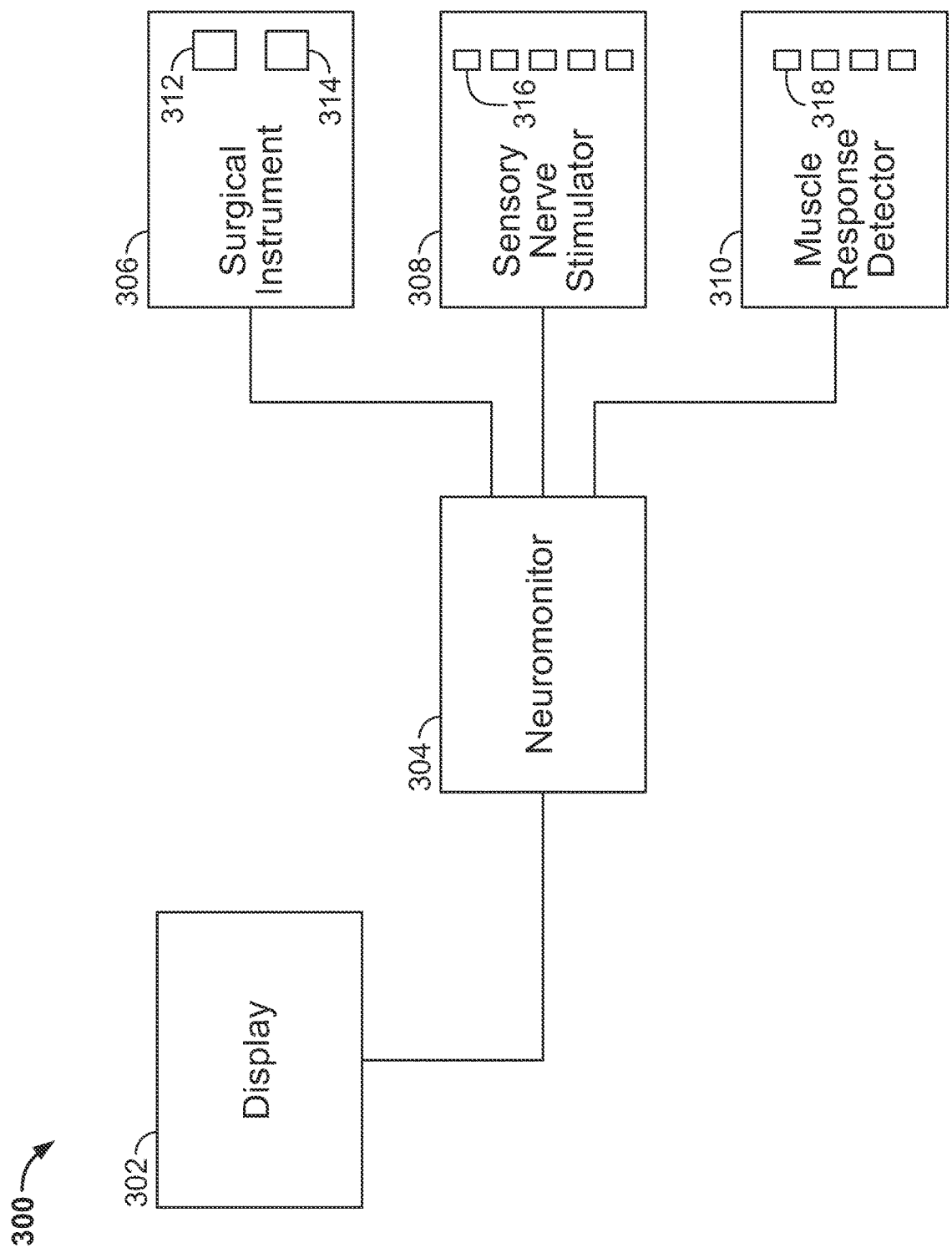
FIG. 2 shows a block diagram of a neuromonitoring system

A sensory nerve neuromonitoring system, optionally combined with the motor neuromonitoring functionality, provides for mapping and monitoring the nervous anatomy. To detect sensory, motor, and mixed nerves with a neuromonitoring system, sensory and motor stimulating and detecting components can be incorporated into the neuromonitoring system. Such a combined nerve monitoring system is illustrated by neuromonitoring system 300 in FIG. 2. The system 300 includes a display 302, a neuromonitor 304, a surgical instrument 306, a sensory nerve stimulator 308, and a muscle response detector 310. The neuromonitor 304 provides processing control and logic that creates an operational interface between the display 302 and the sensing and detection components of the system 300. The neuromonitor 304 includes a processor or other logic circuitry programmed to control delivery of stimulation to various patient tissues, receive detected responses to delivered stimulations, and process the stimulus and response data to provide information and intraoperative guidance to a surgeon on display 302. The neuromonitor 304 is equipped to be toggled quickly between a first state in which it initiates tissue stimulation at stimulating electrodes connected to the neuromonitor and a second state in which it receives detected electrical signals from sensors placed within or on tissue. The stimulations delivered can be adjusted by the neuromonitor 304, and may include stimulations at varied current amplitudes, frequencies, voltages, or other variable characteristics. For example, stimulations may be delivered at current amplitudes between about 1 mA and about 100 mA, voltages between about 1V and about 100V, and frequencies between about 1 msec and about 1 sec. The neuromonitor 304 may include, for example, a Cadwell Cascade® neuromonitoring unit, or any other suitable neuromonitoring equipment made by Cadwell Laboratories, Inc.

Components of the system 300 that are controlled by the neuromonitor 304 and provide for neuromonitoring of both motor and sensory nerves are provided on a surgical instrument 306. The surgical instrument 306 is an instrument configured to be positioned near a patient's nervous tissue for nerve monitoring, in some implementations near a patient's spinal anatomy. The surgical instrument 306 may be, for example, a monopolar probe, a tissue dilator (which may be tubular or non-tubular), a tissue retractor, working cannula, a scalpel, a tool for implant placement, a pedicle screw, a guide wire, a sequential access surgical system including multiple instruments, or any other surgical instrument that may be used in surgery. For motor nerve monitoring, surgical instrument 306 includes one or more stimulation electrodes 312 for delivering stimulus signals to tissue surrounding the surgical instrument 306. For sensory nerve monitoring, surgical instrument 306 includes one or more nerve response sensors 314 that detect changes in potential in tissue surrounding the surgical instrument 306, for example when a nearby sensory nerve is stimulated and depolarizes as an action potential propagates through the nerve.

The motor nerve monitoring components (e.g., stimulating electrode 312) of surgical instrument 306 elicit muscle responses detected by peripheral components (e.g., muscle response detector 310) of the system 300 at muscles stimulated by delivered stimulations. The muscle response detector 310 includes one or more muscle response sensors 318 for detecting muscle activity triggered by motor nerves stimulated by the electrodes 312. Muscle response sensors 318 may include, for example, skin electrodes, needle electrodes, electromyography sensors (which may include skin or needle electrodes), piezoelectric sensors, other mechanical sensors, or any other suitable sensors for detecting muscle activity.

The sensory nerve monitoring components (e.g., response sensors 314) of surgical instrument 306 detect the sensory nerve responses elicited by stimulations delivered by peripheral components (e.g., sensory nerve stimulator 308) at innervated sensory tissues. The sensory nerve stimulator 308 includes one or more stimulating electrodes 316 for delivering stimulus to sensory tissues, such as dermatomes innervated by sensory nerves, in the vicinity of surgical instrument 306. The stimulating electrodes may include, for example, skin electrodes, needle electrodes, monopolar or bipolar probes, or any other suitable electrodes for delivering stimulus to sensory tissues.

The coordination of the stimulation components and response detection components of system 300 for both motor and nerve monitoring is performed by the neuromonitor 304. The neuromonitor 304 is programmed to toggle between stimulation and sensing. Processors or other control circuitry of neuromonitor 304 execute algorithms that synchronize the stimulations delivered by electrodes 312, elicited muscle responses detected by muscle response sensors 318, stimulations delivered by electrodes 316, and elicited sensory nerve responses detected by response sensors 314. The processing components of neuromonitor 304 then process the sensory and motor nerve data received from surgical instrument 306, sensory nerve stimulator 308, and muscle response detector 310, and provides guidance or warnings to the surgeon regarding both sensory and motor nerves in the vicinity of surgical instrument 306 via display 302. Each of the components of system 300 may be implemented using any suitable combination of hardware circuitry, firmware, and software using computing devices that include processing circuitry, non-transitory computer memory (including volatile and non-volatile units) for storing software programs and/or data (including databases of neuromonitoring sessions data), communication circuitry, user interface (including user input/output controls, and graphical user interfaces, where suitable). The components of system 300 may be connected by cable which carries digitized signals from one component to another, or by wireless communications using serialized or parallel message packets. In some implementations, some of the components of system 300 may be located remotely from other components of the system.

Figure 3:
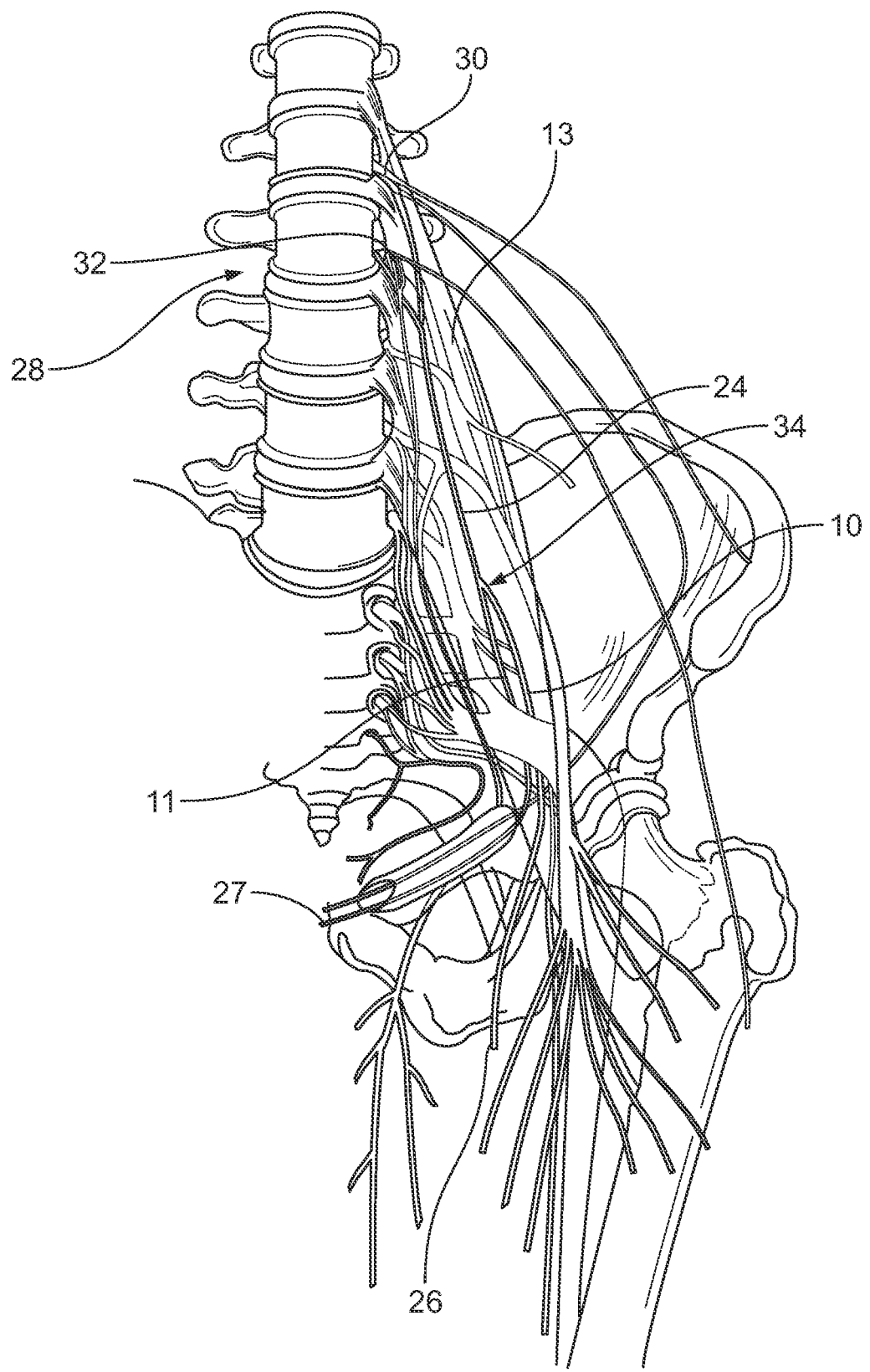
FIG. 3 shows anatomy of the spine and spinal nerves.

During surgical procedures, such as spinal surgeries, in tissues having motor, sensory, and mixed nerves, sensory and motor monitoring provides for mapping and monitoring full nerve anatomy, rather than just one or two of these three types of nerves. An illustrative combination of sensory and motor nerves that may be in the proximity of a surgical instrument, such as the instrument 4, during a spinal approach is shown in FIG. 3. It is understood that due to the complexity of the human anatomy, FIG. 3 illustrates only a few of the nerves that may be monitored, but other nerves would likely be present and can be monitored and detected by similar neuromonitoring principles and technologies. As illustrated, a series of nerves exit the patient's spine 28 through nerve roots on the lateral sides of the spine. These nerves include the genitofemoral nerve, which includes a main branch 24 that exits the spinal cord, with nerve roots 30 and 32 at the level of the L-1 and L-2 lumbar vertebrae. The main branch 24 then splits at a junction 34 into the femoral branch 10 and the genital branch 11 of the nerve. The femoral branch 10 runs down from the junction 34 to a nerve ending 26 that innervates a skin dermatome in the upper part of the femoral triangle on the patient's inner thigh. The genital branch 11 turns medially from the junction 34 and runs to a nerve ending 27 that innervates the cremaster muscle and scrotal skin in males and the mons pubis and labia majora in females. Using the generally known structure and anatomy of the main branch 24 and two forked branches 10 and 11 of the femoral nerve as well as the general position of the nerve endings 26 and 27, stimulating electrodes, such as the array 12 shown in FIG. 1, are placed on the skin in the general area of the nerve endings 26 and 27 to stimulate and monitor the proximity of an instrument approaching any of the branches 10, 11 or 24 during a surgical procedure.

The systems and methods described herein analyze the location and condition of the nerves shown in FIG. 3 before, during, and after surgical procedures. Probes are used before a surgery to investigate the patient anatomy and create a pre-surgical map of the nerves shown in the figure, for example the genitofemoral nerve or other nerves located in or near the psoas major muscle 13. The map may then be used to pre-plan a surgical approach or guide a surgeon during surgery to reduce the risk of injuring those nerves. During the surgery, stationary probes are positioned near the mapped location of the nerves to monitor the nerve for potential danger or intraoperative damage. All tools used during the surgery may also be electrified to guard against damaging the nerves during approach or intraoperative handling. Following the surgery, probes or other tools are used to assess the post-surgical health of the nerves and check for any complications from the surgery that may cause pain or partial paralysis following the surgery.

Figure 4:
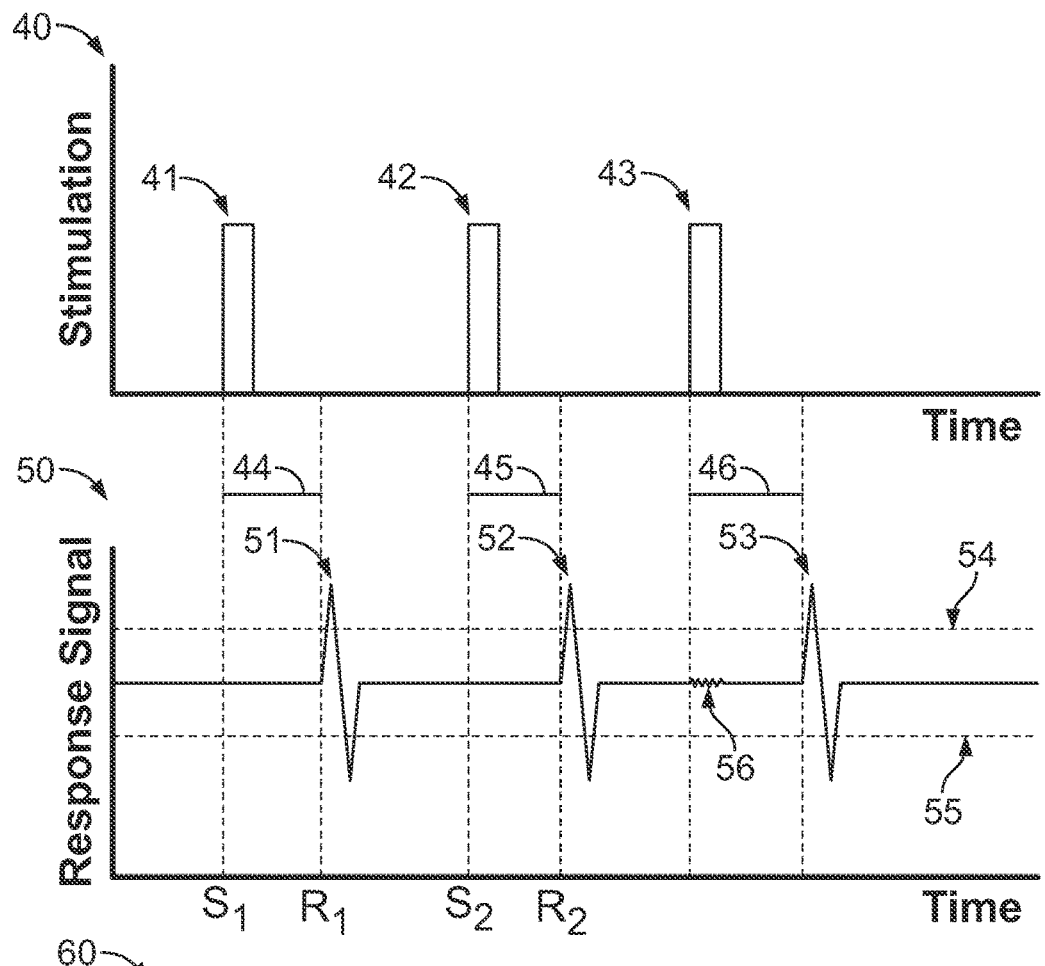
FIG. 4 shows a stimulus profile and response signal during neuromonitoring of a sensory spinal nerve.

FIG. 4 illustrates a process for detecting or monitoring the genitofemoral nerve, or another sensory nerve, during a lateral approach to the spine or a surgical procedure performed at the spine. The detection and monitoring is illustrated by a stimulus profile 40 and nerve response signal 50. The stimulus profile 40 shows three stimulation pulses 41, 42 and 43 delivered to a skin dermatome by one or more stimulating electrodes, for example by one or more of the electrodes 14 in the array 12 shown in FIG. 1. Each of the stimulation pulses 41, 42 and 43 triggers a sensory response from a sensory nerve that innervates the dermatome to which the stimulations are delivered. As a result, each stimulation pulse 41, 42 and 43 produces a corresponding nerve response 51, 52, and 53 in the nerve response signal 50 detected near the sensory nerve, for example by electrodes on the distal end 16 of the instrument 4 shown in FIG. 1. The sensed nerve responses 51, 52, and 53 are the result of the sensory nerve depolarizing as the sensory nerve action potential propagates from the point of stimulation towards the brain.

Because the stimulation is delivered at the skin dermatome, and the nerve response is measured upstream, for example near the nerve root, there is a latency associated with each of the nerve responses 51, 52 and 53 relative to their corresponding stimulation pulse 41, 42 and 43. For example, the first pulse 41 is delivered at time $s_1$, and the nerve response in the corresponding sensory nerve begins at time $r_1$, creating a latency 44 between the stimulation pulse 41 and the sensed response 51. Likewise, the second stimulation pulse 42 is delivered at time $s_2$, and the corresponding nerve response 52 is detected at time $r_2$, creating a latency 45 after the delivery pulse. Finally, the third pair of stimulation pulse 43 and nerve response 53 has a latency 46 that is substantially equal to both latency 44 and latency 45.

While the nerve responses 51-53 shown in response signal 50 are large, there may be smaller, insignificant responses or noise signals within the response signal 50 that are not true nerve responses caused by the stimulation pulses 41-43. In order to differentiate noise and insignificant responses from actual triggered nerve responses, an upper threshold 54 and lower threshold 55 may be applied to the response signal 50, in addition to one or more of any number of known filtering techniques. Only nerve response signals that exceed one or both of these thresholds 54 and 55 are considered true nerve responses. For example, response signal 50 includes a noise portion 56. The noise portion 56 may be caused by external stimulation, random nerve activity, electrical interference, or any other source of noise and should not be considered a true nerve response. By applying the thresholds 54 and 55, the noise signal 56 is filtered out, and only the true nerve responses 51, 52 and 53 are used to assess the nerve characteristics during the spinal surgery.

The stimulus profile 40 and the nerve response signal 50 show three similar stimulation pulses 41, 42 and 43 producing three similar nerve responses 51, 52 and 53 having generally similar amplitudes and latencies. The reproducibility of these nerve responses is useful in monitoring the sensory nerve during a surgical procedure. For example, the probe used to deliver the stimulation pulses 41, 42 and 43 may be left stationary in the vicinity of the monitored nerve while other surgical components are advanced toward or past the nerve to the spine. The neuromonitoring system can deliver subsequent stimulation pulses similar to the three stimulation pulses shown in the stimulus profile 40, and the amplitude and latency of subsequent nerve responses can be monitored to detect changes in the nerve response signal that may indicate problems or potential damage to the monitored sensory nerve. For example, if the probe is not moved and delivers a fourth stimulation signal, a resultant nerve response having an amplitude that is noticeably smaller than the three responses 51, 52 and 53 could signal an impingement or other problem. In particular, if that response does not exceed one of the thresholds 54 and 55, it could indicate that there has been damage to the monitored nerve. In addition, an increase or decrease in the latency of subsequent nerve response signals may indicate that the monitored nerve has been either damaged or is being compressed by the surgical procedure.

Figure 5:
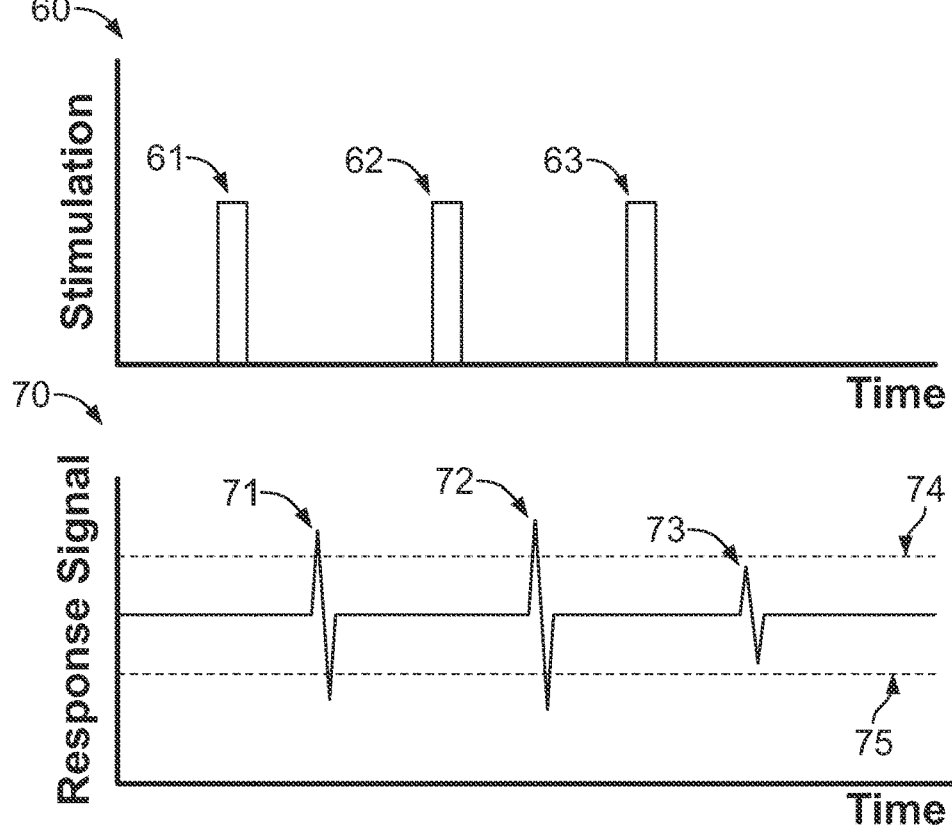
FIG. 5 shows a stimulus profile and response signal during neuromonitoring of an injured sensory spinal nerve.

FIG. 5 shows a stimulus profile 60 and a nerve response signal 70 for monitoring a sensory nerve with a stationary probe while a surgical procedure is carried out using other surgical instruments. The stimulus profile 60 includes three similar or identical stimulation pulses 61, 62 and 63 delivered to a dermatome, for example using the array 12 shown in FIG. 1. The response signal 70 shows three nerve responses 71, 72 and 73, corresponding to respective stimulation signals in the sequence 60. As shown in the response signal 70, the first two responses 71 and 72 are similar to the responses 51, 52 and 53 shown in FIG. 4. These responses indicate that the monitored sensory nerve is intact and not impinged upon during the surgical procedure. The third response signal 73 caused by the stimulation pulse 63, however, is noticeably smaller than each of the two nerve responses 71 and 72. The response 73 does not exceed either of the two thresholds 74 and 75, which are exceeded by both the first and second response signals 71 and 72. If the probe delivering the stimulus profile 60 is not moved between the stimulation pulse 62 and stimulation pulse 63, the changed amplitude of the nerve response 73 may be an indication that the monitored nerve has been contacted or damaged in some way. If this is the case during surgery, a warning or other indication is displayed to the surgeon, for example on the display 8 shown in FIG. 1, communicating that there may be a problem with the monitored nerve, and further evaluation should occur before instruments are advanced any further into the body or spine.

Figure 6:
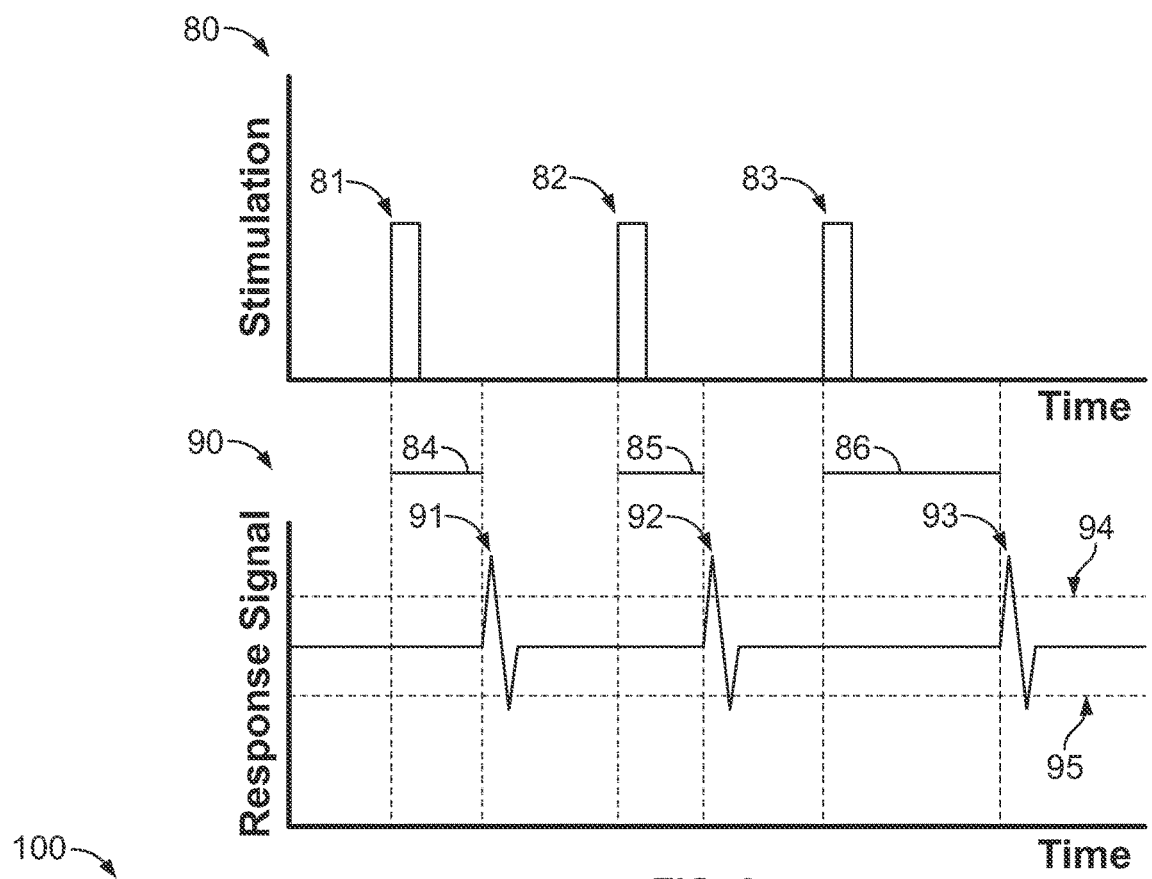
FIG. 6 shows a stimulus profile and response signal during neuromonitoring of a compressed spinal nerve.

In addition to the change in nerve response amplitude shown in FIG. 5, a change in response latency may indicate a potential problem with a nerve during surgery. The stimulus profile 80 and nerve response signal 90 shown in FIG. 6 depict such a latency change. Like the stimulation and nerve response sequence shown in FIG. 5, the first two stimulation pulses 81 and 82 in FIG. 6 elicit two nerve responses 91 and 92 having similar amplitude and latencies 84 and 85. The third stimulation pulse 83, however, elicits a nerve response 93 that has a longer latency 86 than the previous responses 91 and 92. Although the response 93 still exceeds both thresholds 94 and 95, as responses 91 and 92 do, the increased latency 86 may be an indication that there is an injury or potential problem with the monitored sensory nerve. For example, if a surgical tool is pressed against a monitored nerve and compresses a portion of the nerve, the time required for a nerve signal to travel from the stimulated dermatome to the monitored portion of the nerve may be increased by the compressed portion. As with the decreased response amplitude detected in FIG. 5, an indication or a warning may be displayed to the surgeon, for example on the display 8 shown in FIG. 1, that latency has increased and there may be a potential injury or danger to a monitored sensory nerve.

Figure 7:
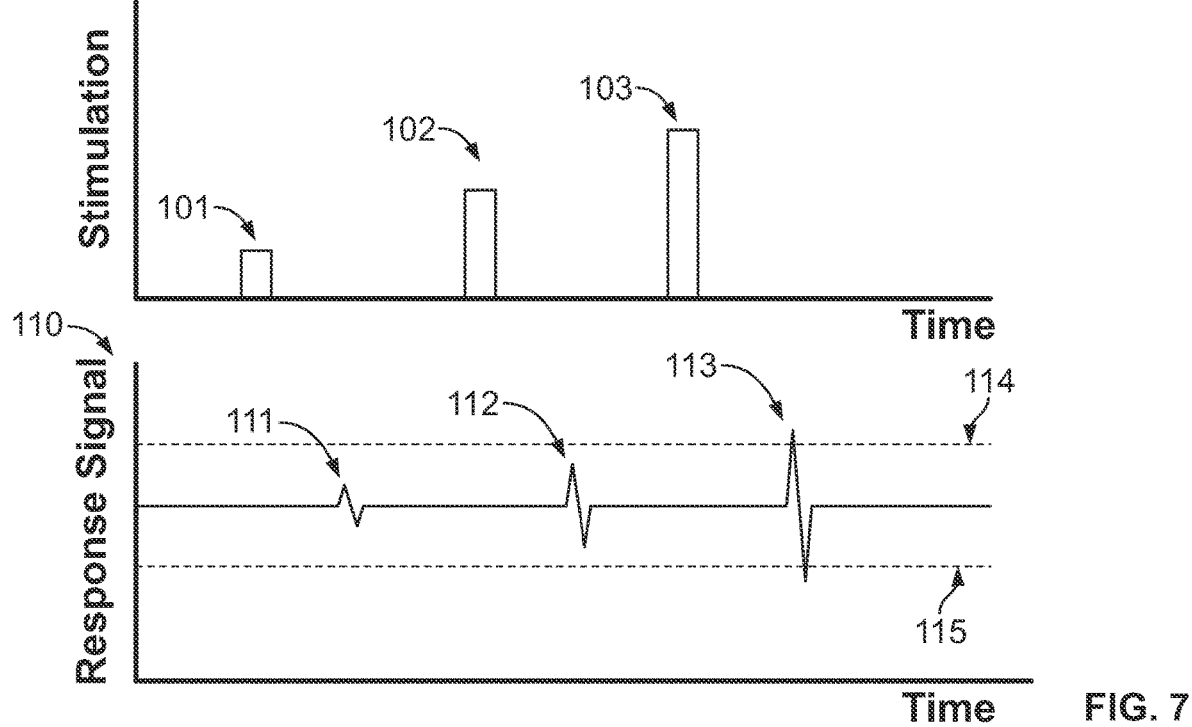
FIG. 7 shows a stimulus profile having pulses with increasing intensities and a corresponding response signal.

In addition to continuously or intermittently monitoring a sensory nerve from a stationary probe that is known to be near that nerve, the neuromonitors described herein also determine the proximity of a surgical tool to a sensory nerve at an unknown location during lateral approach and access to the spine. An example of stimulation and nerve responses used to determine the proximity of such a nerve are shown in the stimulus profile 100 and nerve response signal 110 in FIG. 7. The stimulus profile 100 includes three stimulation pulses 101, 102, and 103 shown increasing in intensity, and three corresponding nerve responses 111, 112, and 113 elicited by the three stimulations. The change in magnitude of the stimulation from pulse 101 to pulses 102 and 103 may be controlled by, for example, changing a current level, a pulse width, or any other suitable characteristic of the stimulation pulse that increases its intensity. The nerve response signal 110 illustrates the increased amplitude of each subsequent response elicited by the stimulus profile 100. In particular, the first response 111 is a small response that does not approach either of the thresholds 114 or 115. The second response 112 has a greater amplitude and approaches the thresholds, but still does not exceed either threshold level. For the highest intensity stimulation pulse 103, the corresponding nerve response 113 exceeds both thresholds 114 and 115 and indicates that the intensity of the stimulation pulse 103 delivered to the innervated dermatome is sufficient to elicit a nerve response in the monitored sensory nerve. This indication may be used to determine, for example, a threshold stimulus intensity required to stimulate the nerve. If the determined threshold intensity, for example the intensity of pulse 103, is below a safe level, an indication may be provided to a surgeon that the tool sensing the nerve responses 110 is approaching too near to the nerve.

Additional neuromonitoring may be implemented to determine a threshold stimulation required to elicit a sensory nerve response to a desired resolution. For example, once stimulation pulse 103 is determined to elicit a nerve response 113 that exceeds the thresholds 114 and 115, further stimulation and response testing may be used to determine a narrower threshold window between the intensities of pulses 102 and 103 that contains the minimum required intensity to elicit a substantial nerve response. The additional stimulation and sensing techniques may include providing additional stimulation at intensities between the pulses 102 and 103, for example using the stimulation techniques discussed with respect to motor nerve monitoring in U.S. Provisional Application Nos. 61/721,482, 61/796, 207, and 61/730,202, which are hereby fully incorporated by reference herein.

The approaches shown in FIGS. 4-7 illustrate monitoring techniques for a sensory nerve that can be detected by delivering stimulations to the dermatome near the precise location of a nerve ending, for example the end of the femoral or genital branch of the genitofemoral nerve. In cases where an electrode is used that is not directly on the dermatome innervated by the nerve, the responses sensed by a surgical tool may be minimal, even if the surgical tool is in the vicinity of the nerve. This could result in dangerous situations in which the tool is near or contacting the nerve, but no warning is generated because minor or no nerve responses are detected. Calibration and testing before neuromonitoring can be performed to determine one or more optimal electrodes, for example electrodes in an array such as array 12, to be used to stimulate the dermatome and elicit detectable nerve responses.

Figure 8:
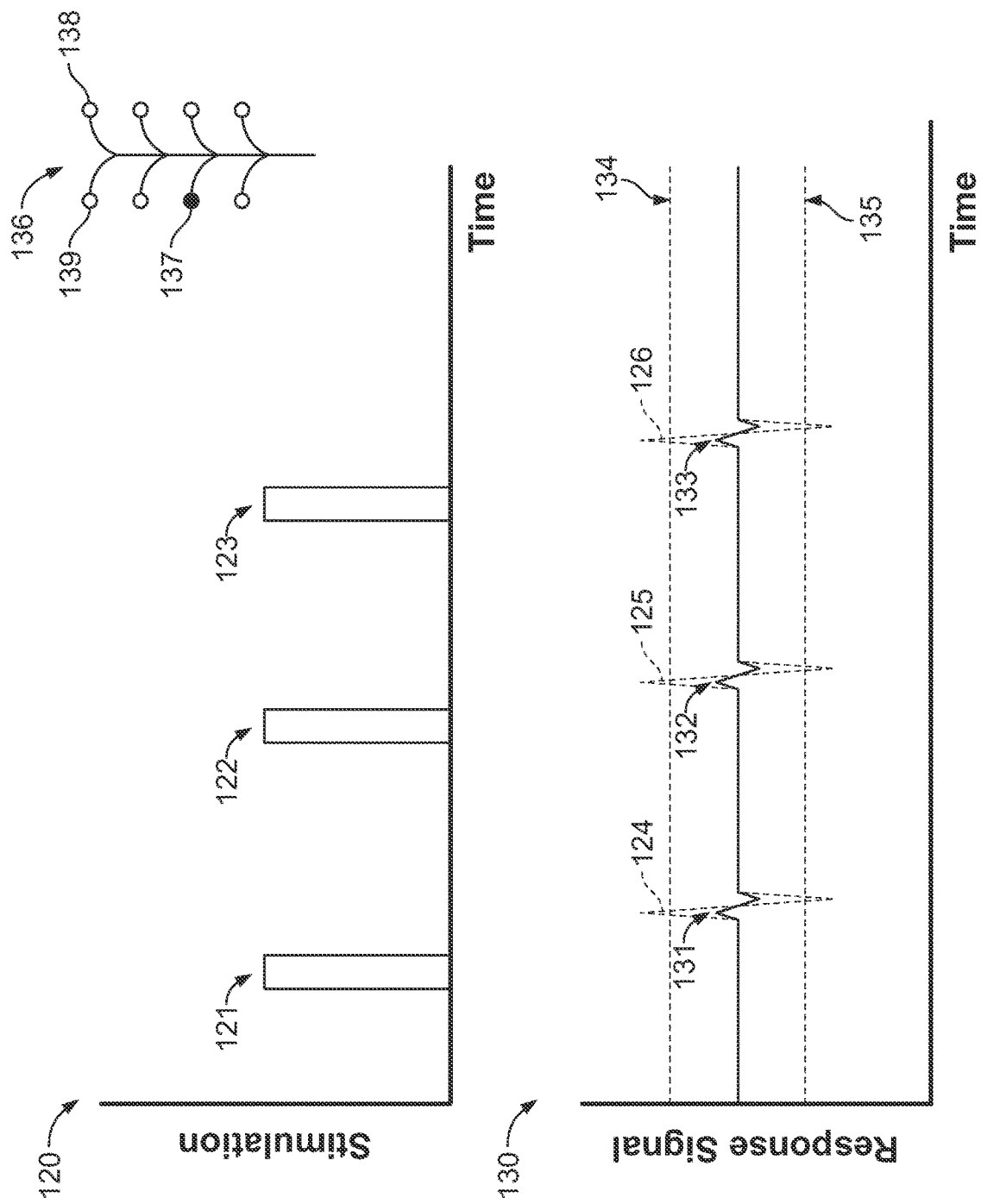
FIG. 8 shows a stimulus profile and response signal of a below-threshold sensory spinal nerve response.

FIG. 8 shows a stimulus profile 120 and a nerve response signal 130 that are delivered and elicited from sensor array 136 during calibration and stimulation configuration. The three stimulation pulses 121, 122, and 123 in stimulus profile 120 are delivered from a single stimulation electrode 137 in the array 136. In response to each of the pulses, nerve responses 131, 132, and 133 are detected at a sensor electrode on an instrument used in a lateral spinal approach surgery. For the calibration test, the instrument and response sensor electrode are positioned near the stimulated sensory nerve, but each of the three nerve responses 131, 132, and 133 does not exceed either of the thresholds 134 or 135. The small nerve responses, despite the proximity of the sensor to the nerve, may be a result of the electrode 137 not being positioned on the skin directly over the dermatome innervated by the monitored nerve, or may be a small response because the electrode 137 stimulates only one branch of the nerve ending. Other combinations of the electrodes in array 136, for example delivery of stimulus from electrodes 138 or 139, or a combination of those electrodes, may be more preferable for delivering stimulus and may elicit greater responses from the nerve, for example by stimulating additional dermatomes or additional nerve endings on a single dermatome. For example, delivery of a stimulus from either electrode 138 or 139 may elicit the nerve responses 124, 125, and 126 using the same stimulation pulses 121, 122, and 123. Because each of these nerve responses 124, 125, and 126 are greater in magnitude, and each exceeds thresholds 134 and 135, delivery of stimulus from these alternative electrodes improves the response detectability and would be preferable. In the calibration process, all of the electrodes in the array 136 may be tested, and those electrodes that elicit the greatest nerve responses, or a combination of those electrodes, may be used for delivery of the stimulus during active neuromonitoring.

In addition to the amplitude of nerve responses elicited by stimulation delivered from different electrodes in an array, each nerve response may have a different latency that can compromise the detectability of active responses from the sensory nerve. The differences in latency may result from the electrodes being positioned different distances from the triggered nerve ending, or positioned near different nerve endings with slightly different response latencies. An electrode that is directly on top of a nerve ending may elicit a nerve response that propagates quickly, while an electrode positioned farther away from the nerve ending may elicit a response that takes longer to propagate to the portion of the nerve monitored by a sensory probe. If the nerve responses are detected at separate times, there may not be one response large enough to trigger a threshold, though all three response are actual nerve responses to the stimulation. During the calibration period, this difference in time latencies can be accommodated both by selecting particular electrodes used to deliver the stimulation and by synchronizing the timing of the stimulations delivered from each electrode. In particular, the stimulation pulses may be synchronized such that the responses elicited by each reaches the response sensor at generally the same time, creating a compound action potential that produces a single large detected nerve response from the sensory nerve.

Figure 9:
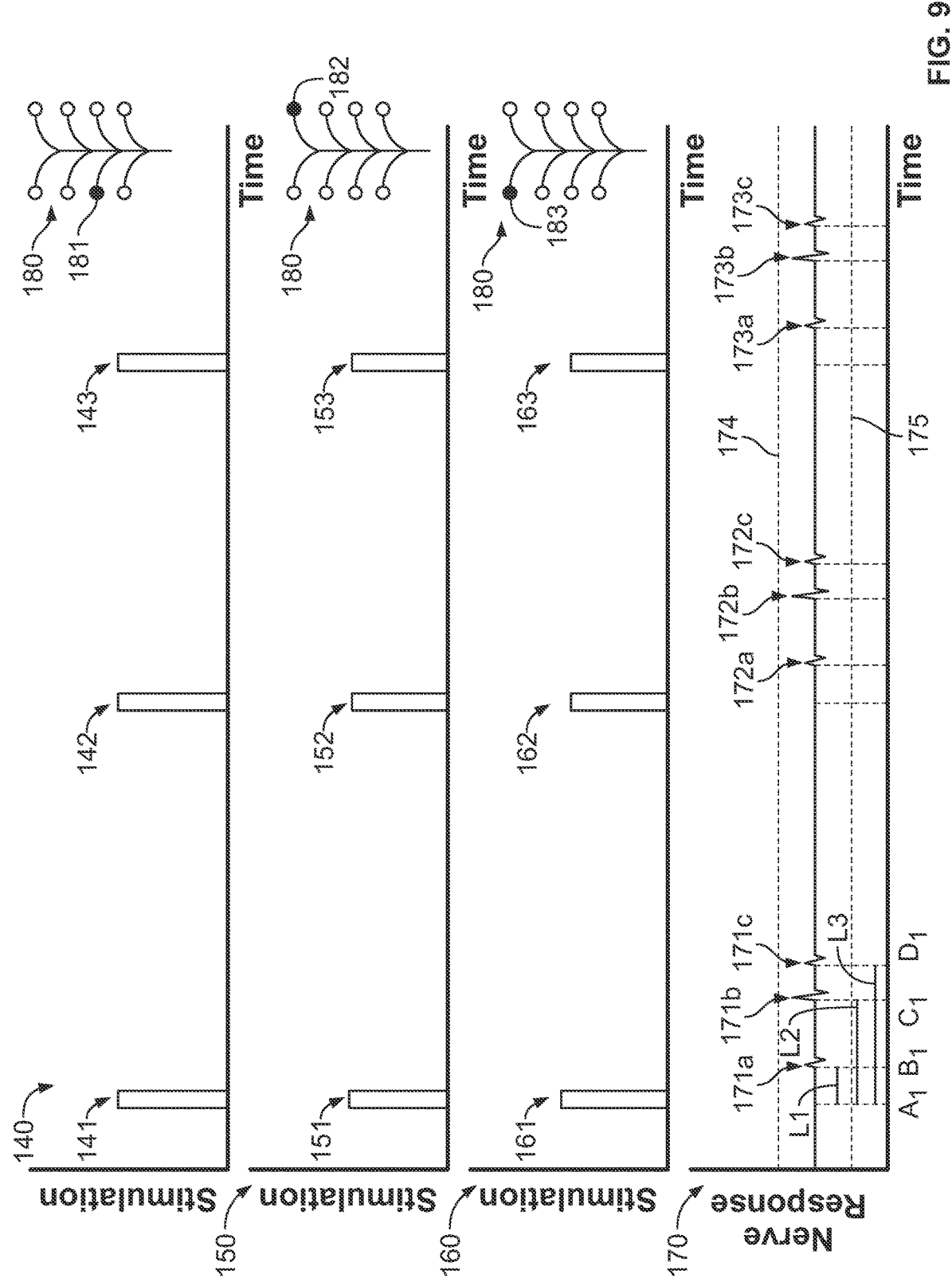
FIG. 9 shows stimulus profiles and a response signal of a sensory spinal nerve exhibiting different response latencies in the response signal.
Figure 10:
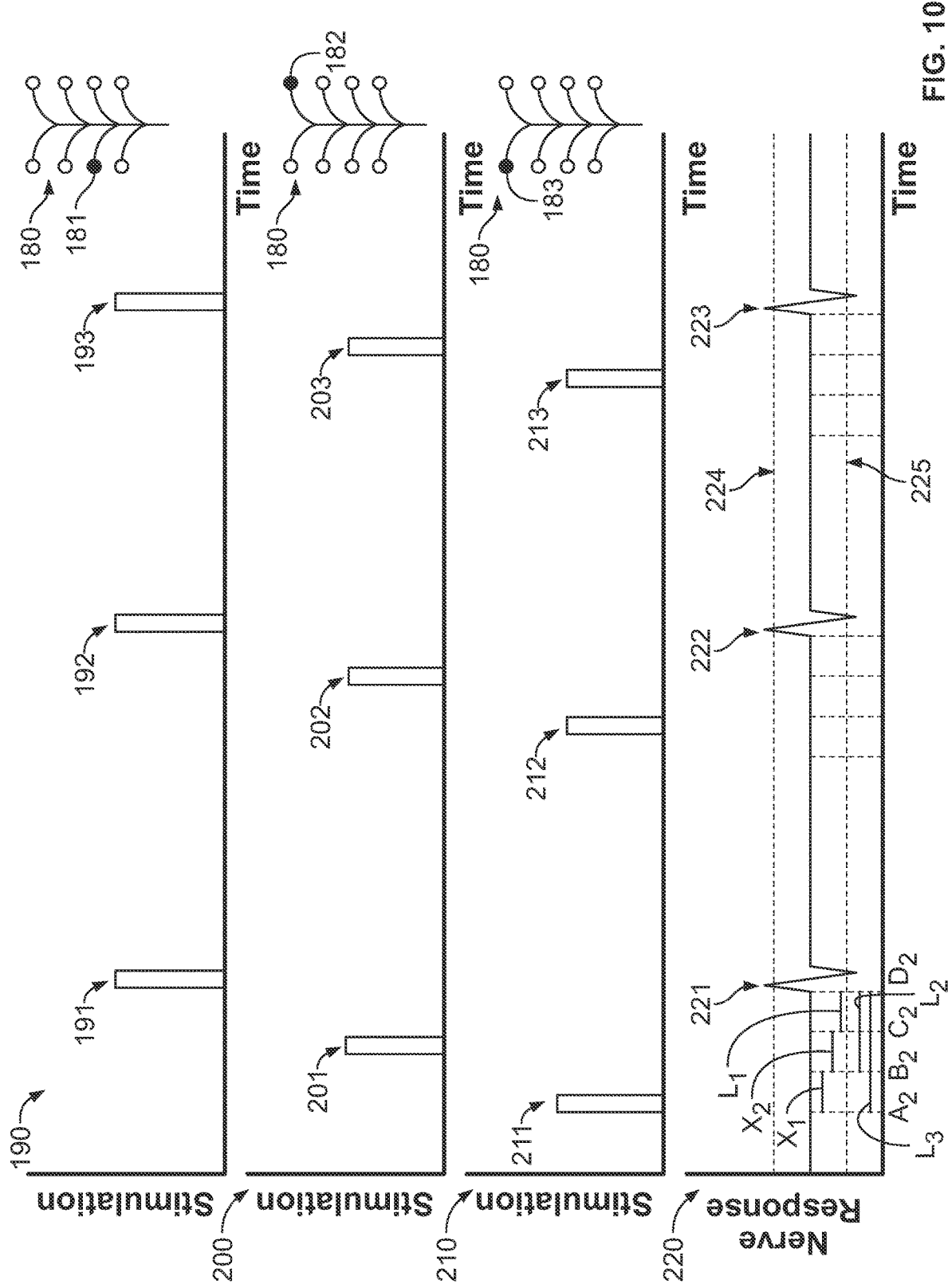
FIG. 10 shows stimulus profiles and a response signal of synchronized stimulation pulses creating a compound action potential.

FIGS. 9 and 10 depict a process for syncing stimulation signals delivered from three different electrodes, for example during calibration and configuration of a sensor array, to elicit a detectable compound action potential from a sensory nerve. The data from this process can also be used to triangulate and detect locations of nerves near these different electrodes. The position of three electrodes 181, 182, and 183 in a stimulation array 180 is shown on the right, and stimulus profiles 140, 150, and 160 corresponding to electrodes 181, 182, and 183, respectively, are shown on the left. Nerve response signal 170 depicts the electrical nerve activity detected by a sensor probe near the sensory nerve during delivery of the stimulations. Each of the stimulus profiles 140, 150, and 160 includes three stimulation pulses delivered from the electrodes 181, 182, and 183 simultaneously. In particular, three stimulation pulses 141, 151, and 161 are delivered from electrodes 181, 182, and 183, respectively, at time point $A_1$. The nerve response signal 170 shows three individual detected nerve responses 171a, 171b, and 171c corresponding to each of the stimulation pulses 141, 151, and 161, respectively. No one nerve response exceeds one of the thresholds 174 and 175, and thus simultaneous stimulation from electrodes 181, 182, and 183 does not produce a reliably detectable response from the monitored nerve.

The spreading of the nerve responses 171a, 171b, and 171c results from differences in latencies, or the time it takes a triggered nerve signal to travel from the stimulated dermatome to the area of the nerve monitored by the sensing probe for each electrode stimulation. The first nerve response 171a, corresponding to the stimulation pulse 141 from electrode 181, is received at time $B_1$, and the latency for this response is $L_1$, which is the lag from the stimulation time $A_1$ to the sensed response time $B_1$. The second nerve response 171b, corresponding to the stimulation pulse 151 from electrode 182, is received at time $C_1$, which is later than $B_1$ and lags the stimulation time $A_1$ by a longer latency $L_2$. Finally, the third nerve response 171c, corresponding to the stimulation pulse 161 from electrode 183, is received at time $D_1$, later than both $B_1$ and $C_1$, and lags behind the stimulation time $A_1$ by a longer latency $L_3$. For subsequent stimulations from the electrodes 181, 182, and 183 in array 180, both the latencies and amplitudes of the three detected nerve responses remain generally constant, as the sensing probe is not moved nearer to or farther from the monitored nerve. Thus, the nerve responses 172a, 172b, and 172c, corresponding to stimulation pulses 142, 152, and 162, and the nerve responses 173a, 173b, and 173c, corresponding to stimulation pulses 143, 153, and 163, exhibit latencies similar to nerve responses 171a, 171b, and 171c.

The nerve responses elicited by each individual electrode are processed by a neuromonitor to determine the amplitudes and latencies of the responses. The neuromonitor uses the determined amplitudes and latencies to time stimulation signals to elicit a larger compound action potential from a nerve and create a more easily detected signal having a greater signal-to-noise ratio. For example, in a calibration phase, each electrode in array 180 delivers sequential stimulation pulses one at a time, and the nerve responses detected for each electrode are analyzed to determine an optimal combination of electrodes exhibiting desired response amplitudes and latencies. A stimulus profile is then generated by a neuromonitor processor or other circuitry and is used to control the selected electrodes to deliver stimulations at different times, as shown in FIG. 10.

The timing of the generated stimulus profile can be programmed so as to elicit a compound action potential from the sensory nerve. Using test stimulations and responses, the program accounts for differing amplitudes and latencies of the signals obtained from the electrodes shown in FIG. 9, which may be placed at different distances from the nerve, near different nerve branches, or on different dermatomes. The stimulation controlled by the neuromonitor and the generated program it executes is applied to those locations in a synchronized fashion, so that the responses elicited from those different stimulations are also synchronized, thereby creating a large aggregate signal propagating through the sensory nerve. For example, the neuromonitor (e.g., neuromonitor 2 in FIG. 1) is programmed to process the test stimulation and test response data and select the electrodes that elicit larger responses, as those responses also produce a larger signal-to-noise ratio. The neuromonitor then uses the latencies for each of the selected electrodes to program a delay in stimulation at electrodes that elicit faster responses, so that the aggregate responses arrive at or near the same time in the area of the nerve monitored by the response sensor.

FIG. 10 depicts three stimulus profiles 190, 200, and 210 for the electrodes 181, 182, and 183, respectively, which are not delivered simultaneously but rather are offset and synchronized based on the three latencies $L_1$, $L_2$, and $L_3$ determined from the stimulations and responses shown in FIG. 9. The timing of stimulus profiles 190, 200, and 210 is calculated by the neuromonitor in order to elicit individual responses that reach the sensor probe at substantially the same time, creating the compound action potential that creates a single detectable response each time the three electrodes deliver stimulation. The resulting nerve responses 221, 222, and 223 in the nerve response signal 220 do not exhibit the spread of three distinguishable responses shown in FIG. 9, but rather each one is a single peak that exceeds the thresholds 224 and 225. The thresholds 224 and 225 are applied to the response signal 220 to differentiate small deviations from noise or interference from true nerve response signals. The large peaks in responses 221, 222, and 223 provide easily detectable signals that allow these thresholds to be applied to cut out noise while reducing the risk of missing actual nerve response signals.

The stimulation pulses 191, 201, and 211 delivered by the electrodes 181, 182, and 183, respectively, are timed by the neuromonitor such that their latencies are accounted for, and each pulse elicits a nerve response that reaches the probe at response time $D_2$, as shown for the nerve response 221. To elicit this response, the electrode having the longest latency in FIG. 9—latency $L_3$ for electrode 183—is pre-programmed to deliver a stimulation pulse 211 first, at time $A_2$. The electrode with the second-longest latency in FIG. 9—latency $L_2$ for electrode 182—is pre-programmed to delay stimulation for the difference $X_1$ of latencies $L_3$ and $L_2$ and then deliver a stimulation pulse 201 at time $B_2$. Finally, the electrode with the shortest of the three latencies in FIG. 9—latency $L_1$ for electrode 181—is pre-programmed to delay stimulation for the additional difference $X_2$ of latencies $L_2$ and $L_1$ and deliver a stimulation pulse 191 at time $C_2$. After each of the pulses are delivered, the nerve signals aggregate, and the compound action potential creates response 221 at time $D_2$, at the synchronized end of each of the three latencies. Because the three latencies are generally constant as long as the nerve is not damaged or compressed, further stimulation with the same timing produces repeatable responses. The subsequent pulses 192, 202, and 212 produce another compound action potential measured by the probe at response 222, similar to response 221. Finally, a third timed sequence of stimulation pulses 193, 203, and 213 elicits a third compound action potential and detected response 223.

Synchronizing stimulation pulses delivered to a dermatome and sensory nerve can elicit a more distinguishable response signal from the nerve and thereby facilitate detection of nerve action potentials in the signal. In systems where both motor and sensory nerves are monitored simultaneously, and particularly when a surgical instrument incorporates both a sensory nerve response sensor and a motor nerve stimulating electrode, further synchronization between the motor and sensory monitoring components can also improve the clarity of response signals. In particular, synchronization among the components can be used to reduce cross talk in the system and reduce the risk of contaminating received response signals for one component with delivered stimulus signals from the other component.

Figure 11:
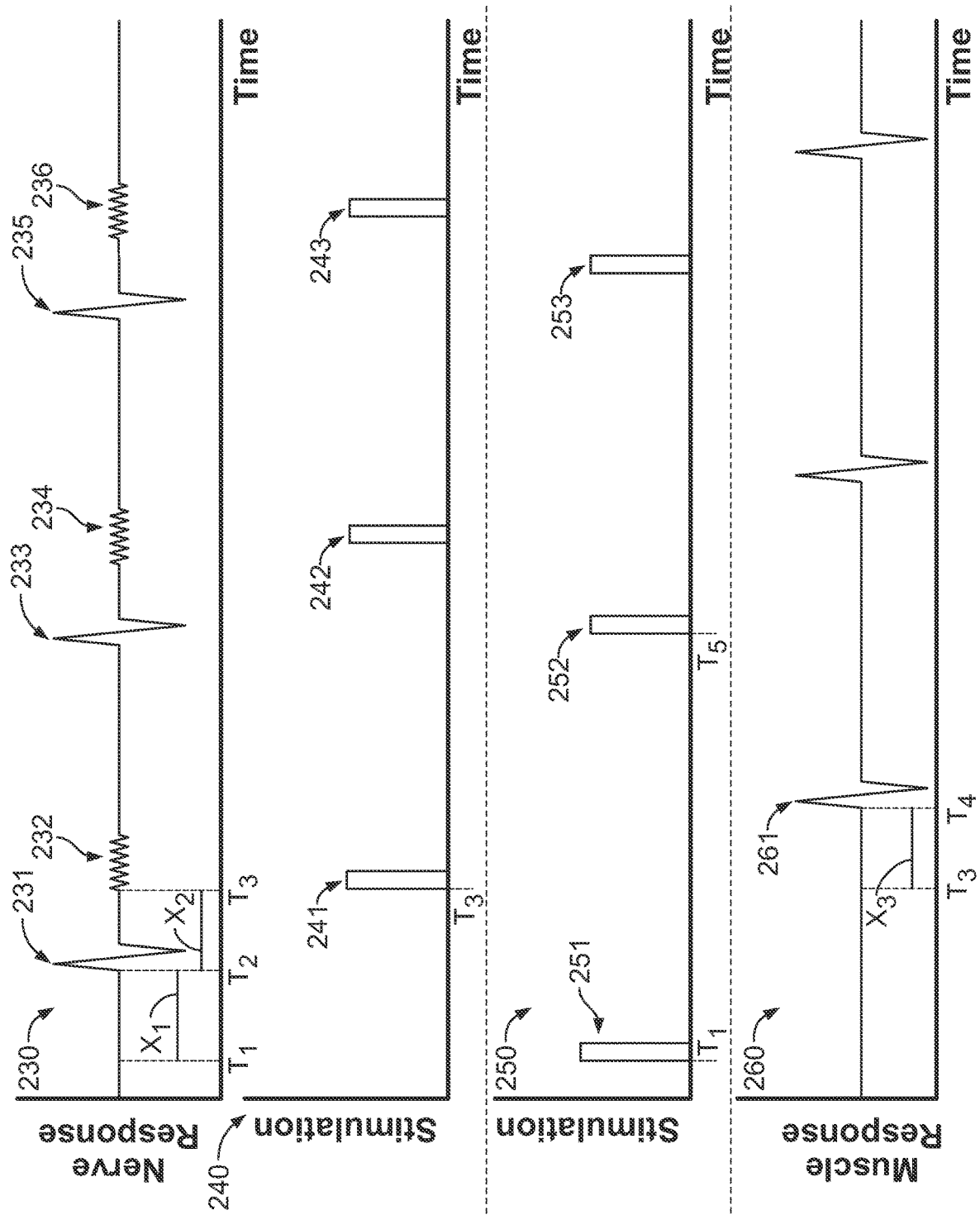
FIG. 11 shows stimulus profiles and a response signal for synchronized motor and sensory nerve monitoring.

FIG. 11 shows a synchronized stimulating and sensing sequence for a neuromonitoring system that includes both sensory and motor nerve monitoring components on a single instrument, for example instrument 4 shown in FIG. 1. In the sequence shown, the instrument is placed near both a sensory nerve and a motor nerve, and both nerves are monitored by the system. The sequence includes a sensory nerve response signal 230 detected by a response sensor on the instrument, as well as a motor nerve stimulus profile 240 delivered by a stimulating electrode on the probe. The sensory response signal 230 detected at the instrument is elicited by sensory stimulus profile 250, which is delivered by surface electrodes to a dermatome innervated by the monitored sensory nerve. The motor stimulus profile 240 emitted by the instrument elicits a motor nerve response signal 260, detected by EMG electrodes at muscles innervated by the monitored motor nerve.

A neuromonitor, such as the neuromonitor 2 in FIG. 1, executes an algorithm that causes the stimulations in stimulus profile 240 to be delivered to the surgical instrument and the stimulations in stimulus profile 250 to be delivered to the dermatome surface electrodes at set times. In response to each of the stimulations in the profiles 240 and 250, the neuromonitor receives nerve response signals 230 and 260 elicited by profiles 240 and 250, respectively. The neuromonitor does not control the delay between a stimulation and a detected response for a given sensory or motor nerve, as that delay is the result of response latency of the nerve itself, but is pre-configured to time the stimulations that are delivered such that the stimulations and the delayed elicited responses do not mix. It is preferable to properly time the stimulations delivered to both the sensory and motor nerves such that the nerve response signal 230 and stimulus profile 240, which are received and delivered from sensors and electrodes near each other on the surgical instrument do not interfere with each other. Using pre-defined values for latencies between stimulation and response detection for both the sensory and motor nerves, the neuromonitor creates stimulus profiles that reduces overlap between the electrical signals, as shown in the stimulations and responses in FIG. 11.

The monitoring process in FIG. 11 begins with delivery of a first stimulation pulse 251 at time $T_1$ to a peripheral sensory tissue innervated by the monitored sensory nerve. The pulse 251 elicits a response from the sensory nerve that is detected at the instrument as response 231. Due to latency in the signal propagation, the response 231 is detected at a time $T_2$ that lags the stimulation time $T_1$ by the duration of the latency $X_1$. If the latency is $X_1$ for the monitored sensory nerve, the neuromonitor that synchronizes the stimulations can wait for a pre-defined period that corresponds to that latency to allow time for the nerve response to be received by the response sensor on the surgical instrument before triggering the motor nerve stimulation pulse 241 at time $T_3$. This delay reduces the risk of producing a false negative detection in the response signal 230 caused by the response sensor disposed on the instrument near the stimulating electrode detecting the stimulation pulse 241. As shown in the response signal 230, interference 232 is detected at the response sensor when the stimulation pulse 241 is delivered. The interference 232 is picked up by the sensor because both the sensor and the stimulating electrode are on the distal end of the surgical instrument, and thus any stimulation delivered by the instrument is also detected by the instrument.

Using the latency $X_1$ and the known or estimated time during which nerve response 231 is detected, the neuromonitor delays the stimulation pulse 241 an additional lag time $X_2$ beyond the latency $X_1$ after delivery of stimulation pulse 251. The time $X_2$ preferably includes a buffer beyond the response detection time in case detected nerve responses, such as response 231, are longer than expected. Once the stimulation pulse 241 is delivered at time $T_3$, the neuromonitor then ignores any response seen in the response signal 230 for a short time period in order to filter out noise from detecting the stimulation, for example at interference 232.

From the stimulation pulse 241, a motor nerve is stimulated, and a subsequent muscle response 261 is detected in the muscle innervated by the nerve at time $T_4$. As with the nerve response 231, the muscle response exhibits a latency $X_3$ as the stimulated signal propagates from the nerve root to the muscle. Following the detected muscle response 261, the neuromonitor begins the timed monitoring protocol again, with a stimulation pulse 252 delivered to the sensory tissue at time $T_5$. As the process repeats, the timing of the stimulations delivered by the neuromonitor in subsequent sequences produces detectable nerve and muscle responses and reduces cross talk between the sensory and motor nerve monitoring components. The subsequent stimulation pulses 242 and 243 delivered from the surgical instrument are timed with a long enough delay from respective stimulation pulses 252 and 253 delivered to the sensory tissue that the elicited nerve responses 233 and 235 are detectable and not affected by interferences 234 and 236 corresponding to the pulses 242 and 243.

The combination of sensory and motor nerve monitoring, and the synchronized timing between stimulations and response detections for the two types of nerves, can be used pre-operatively, intraoperatively, and post-operatively to assess nerve anatomy, location, and health. Changes in the nerve responses, such as changes in response amplitude or response latency, are discussed above as indicators of intra-operative or post-operative deviations from normal nerve functioning that signal danger or injury to the nerve. For pre-operative assessment, a sensory nerve monitoring system, or a combined sensory and motor nerve neuromonitoring system, is used to explore the nerve anatomy and create a map of the anatomy that is used to plan surgery or to guide the surgeon during a procedure.

Figure 12:
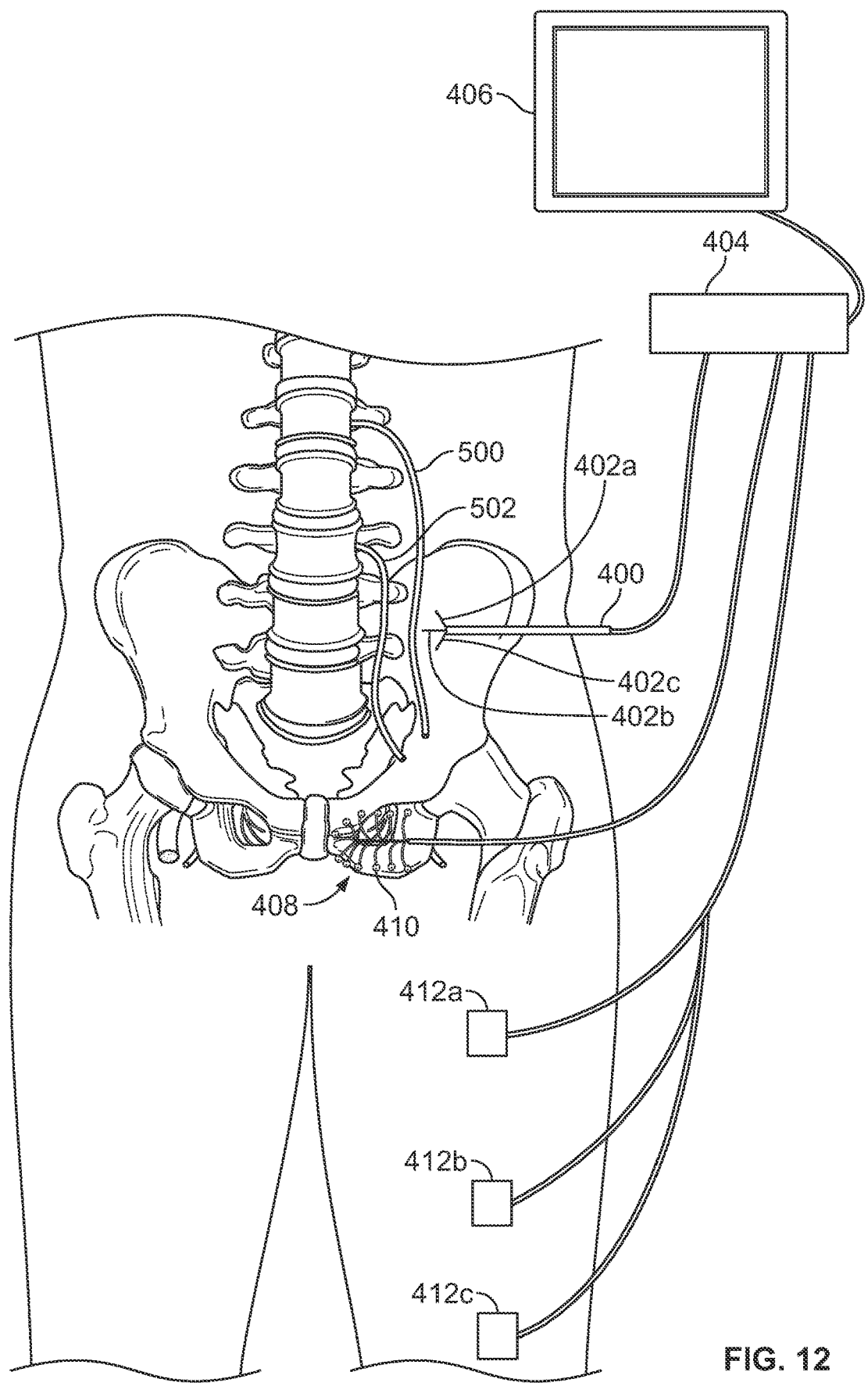
FIGS. 12-14 show a system for mapping nerve anatomy.
Figure 13:
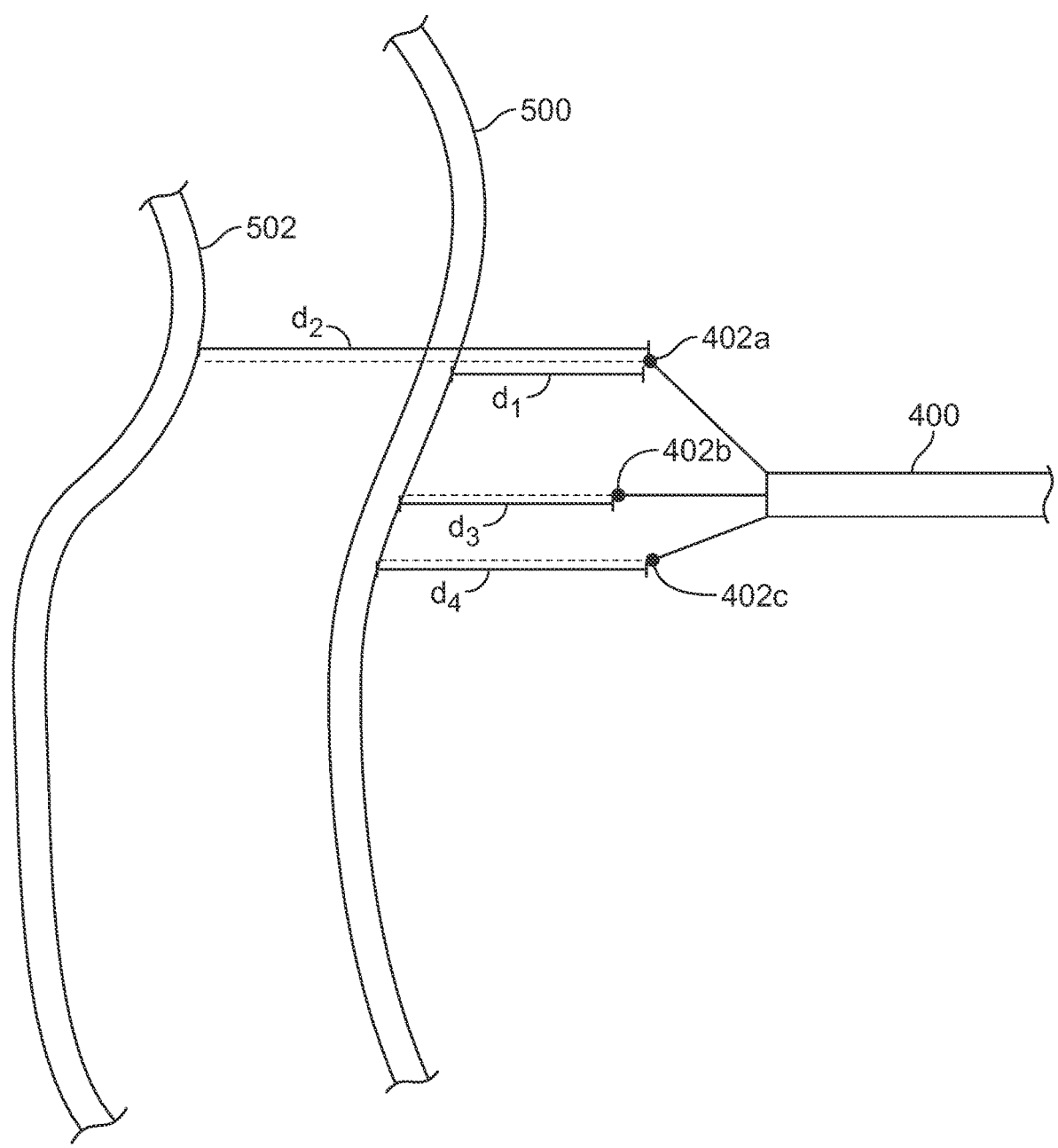
Figure 14:
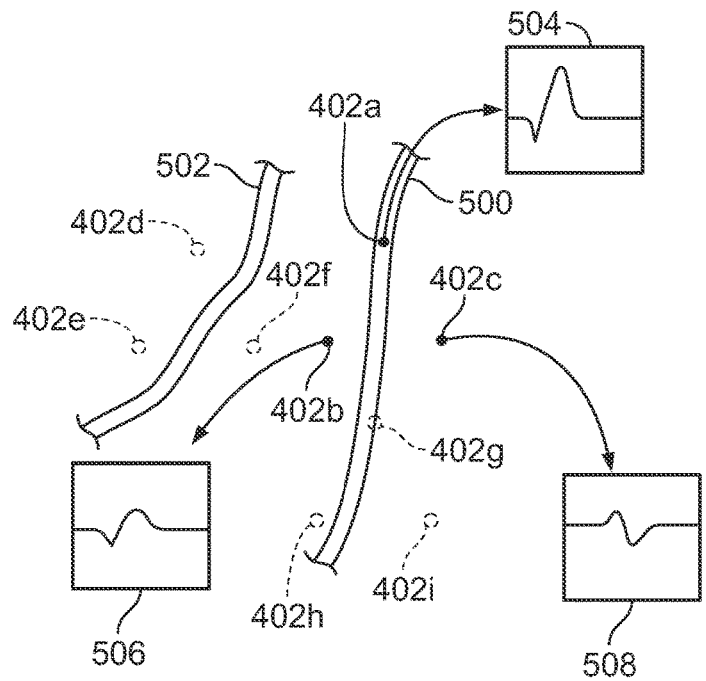

FIGS. 12-14 illustrate a neuromonitoring system used for a pre-operative assessment to locate and map sensory and motor nerve anatomy. The neuromonitoring system includes a probe 400 for assessing and mapping nerve anatomy, neuromonitor 404 coupled to the probe 400, a stimulating sensor array 408, and muscle response sensors 412a-c, similar to the systems described above. In contrast to a surgical tool or probe that has one distal point for detecting nerves, the probe 400 has three different probe ends 402a, 402b, and 402c. Each of the probe ends 402a, 402b, and 402c includes one or more stimulating electrodes and one or more nerve response sensors, which allows the probe 400 to detect electrical signals from both sensory and motor nerves, for example sensory nerve 500 and motor nerve 502 shown in FIG. 12. Those signals are sent to the neuromonitor, and a processor calculates nerve distances and locations with respect to the stimulation electrodes. When multiple distances and locations are determined by the processor in neuromonitor 404, the locations are graphed in a three-dimensional space to create a "map" of the nerve, which my be provided to a surgeon on display 406.

During pre-surgical assessment and mapping implementations, the probe 400 is advanced towards the spine until nerves are detected. As explained further below, the neuromonitor 404, determines distance between the probe and the nerves by processing stimulations delivered and responses detected from each end of the probe ends 402a, 402b, and 402c, and maps the nerve. To obtain the data used by neuromonitor 404 to map the anatomy, the probe 400 is moved to multiple positions within the tissue, and multiple triangulations are performed to determine multiple locations of the nerve and create a representative map of the nerve anatomy.

To locate a motor nerve, the neuromonitor 404 controls delivery of stimulation pulses from the probe ends 402a-c to stimulate motor nerves in the vicinity of probe 400. The stimulations cause muscle responses, and the neuromonitor 404 receives muscle response data after each stimulation from muscle response sensors 412a-c. The sensors 412a-c are positioned on muscles that are innervated by different motor nerves, and the processing circuitry of neuromonitor 404 correlates the sensor at which a response is detected to a particular motor nerve known to innervate the muscle monitored by that sensor. For example, the neuromonitor 404 may retrieve stored data in memory or may receive input from a surgeon identifying the muscle each sensor is monitoring. The processing circuitry associates each sensor with a given spinal nerve based on the identified muscle. When a nerve is detected and a location on the nerve is determined by the processor of neuromonitor 404, the neuromonitor stores the determined location with others previously determined for the same nerve. After multiple locations on a particular nerve are found, the processor creates a map by drawing connections between the determined locations for that nerve.

The neuromonitor 404 processes the characteristics—i.e., the current, frequency, or voltage—of the delivered stimulations and the characteristics of the detected muscle responses to determine the proximity of each probe end 402a-c to the motor nerve, for example nerve 502 in FIG. 12. The neuromonitor 404 may process the stimulations and responses to calculate a distance and/or a direction from each probe end 402a-c to the nerve. In some implementations, a processor in neuromonitor 404 is programmed with an algorithm that uses the stimulating charge and applies Coulomb's law to determine the distance between one of the probe ends 402a-c and the nerve. Coulomb's law can be expressed as $Q=k(Q_0/r^2)$, where Q is the stimulating charge, k is a function of the nerve, $Q_0$ is the minimum charge needed to stimulate the nerve, and r is the distance between the probe end and the nerve. The programmed processor retrieves known values for k and $Q_0$ for the particular nerve being mapped, processes the stimulating charge that stimulated the nerve, and calculates r from this equation. In other implementations, other algorithms or equations are applied by the processing circuitry of the neuromonitor 404 to determine the distances from probe ends to the nerve, and such equations may use the stimulating current, as well as one or more other characteristics of the stimulation or the nerve response, to find the distances.

At each position of the probe 400, three distances and directions to the nerve, corresponding to each of the probe ends 402a-c, are processed to triangulate the location of the nerve relative to the probe 400. The determined location of the nerve relative to the probe 400 is stored in memory in the neuromonitor 404, along with any other previously-determined locations on the same monitored nerve. The surgeon repositions the probe 400 and retests a different area of the nerve to find other locations on the nerve. At each probe position, the nerve location is determined and stored as another point on the map of the nerve. When a sufficient number of locations have been determined to create a map having an adequate resolution, the processor plots the locations stored in memory in a three-dimensional space and creates map of the nerve's path through the monitored anatomy by connecting the plotted locations.

The sensory nerves are also mapped by the neuromonitor 404 and probe 400. To locate a sensory nerve, the electrodes 410 in electrode array 408 are placed on the patient near or on a dermatome that is innervated by the nerve to be mapped. The neuromonitor 404 executes a timed protocol for delivering stimulation and controls the electrodes 410 to deliver the stimulation to the dermatome. The delivered stimulation elicits a propagating action potential response from the nerve, for example from sensor nerve 500 in FIG. 12. This response is detected by response sensors on each of the probe ends 402a-c on the probe 400 near the nerve 500, and the responses are communicated to the neuromonitor 404. Because the probe ends 402a-c are in slightly different positions, they do not detect exactly the same nerve response. The responses detected by each probe end are processed by the neuromonitor to determine the distances from each probe end to the nerve. Similar to the motor nerve triangulation, the probe 400 is moved to different positions in the tissue, and the responses detected at each of the multiple locations are used to locate points along the nerve. The located points are then stored at the neuromonitor 404 and identified with respective locations of the nerve, and the subsequent assessments in different positions are used to create a map of the sensory nerve anatomy.

The responses from sensory nerve 500 obtained at each of probe ends 402a-c indicate the distance and direction from each probe end to the nerve. The responses 504, 506, and 508 shown in FIG. 14 are three representative responses detected by each of probe ends 402a, 402b, and 402c, respectively, in the positions of the probe ends shown in FIGS. 12-14. Each of the responses 504, 506, and 508 are elicited by stimulation applied by electrode array 408 at or near the peripheral sensory tissue innervated by sensor nerve 500. Because probe end 402a is located nearest the sensory nerve 500, the propagating action potential shown in response signal 504 detected at probe end 402a is the largest of the three responses. The responses 506 and 508 depict slightly smaller action potentials, and are nearly equal as a result of the positioning of the probe ends 402b and 402c roughly equidistant from the sensory nerve 500. The orientation of the responses 506 and 508, however, are opposite, as the response 506 begins with a downward deviation while the response 508 begins with an upward deviation. This difference in orientation indicates a different direction from the probe ends 402b and 402c to the nerve 500, as shown in FIG. 14 with the probe ends located both anterior (402b) and posterior (402c) to the nerve 500 when viewed in this lateral direction.

The distances and responses detected in an example sensory nerve mapping process are depicted in the anterior view of the nerves and probe shown in FIG. 13 and the lateral view of the nerves and probe shown in FIG. 14. The probe 400 is positioned nearer to the sensory nerve 500 than to the motor nerve 502, which runs anteriorly and medially from the sensory nerve 500. The probe end 402a is positioned nearest the sensory nerve 500, at a distance $d_1$, while the probe ends 402b and 402c are positioned slightly farther from the sensory nerve 500, at distances $d_3$ and $d_4$, respectively. Because they are approaching from the lateral side, all three probe ends are positioned nearer the lateral sensory nerve 500 than the medial motor nerve 502, as shown with distance $d_2$ from motor nerve 502 to probe end 402a. In this orientation, it may be preferable to map the sensory nerve 500, then use the map of the sensory nerve 500 to guide positioning the probe 400 around the nerve and closer to motor nerve 502 to obtain a map of that nerve.

From the positioning of the probe in FIGS. 12-14, the neuromonitor 404 delivers stimulation and processes responses to determine a location on each of the nerves 500 and 502. The locations may be provided to a surgeon in real time, for example by updating a developing map on the display 406 with the nerve locations as they are determined. The surgeon then moves the probe 404 to obtain more data points and fill out the map of the nerve anatomy. For example, as shown in FIG. 14, the probe ends 402a-c may be moved anteriorly to the positions 402d-f and advanced medially to move closer to motor nerve 502 while maneuvering around sensory nerve 500. This repositioning may be preferable if sensory nerve 500 has already been adequately mapped and the surgeon wishes to obtain more data for motor nerve 502. Alternatively, the probe ends 402a-c can be moved to positions 402g-i to obtain more data for sensory nerve 500 and continue mapping the path of that nerve.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in spinal surgical procedures, may be applied to systems, devices, and methods to be used in other surgical procedures performed in the proximity of neural structures where nerve avoidance, detection, or mapping is desired, including, but not limited to selected brain surgeries, carotid endarterectomy, otolaryngology procedures such as acoustic neuroma resection, parotidectomy, nerve surgery, or any other surgical procedures.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A neuromonitoring system configured to determine a location of a nerve, comprising:
   a nerve stimulator configured to generate and deliver test stimulus signals to a plurality of stimulating electrodes;
   a muscle response detector configured to detect nerve response signals, wherein each of the nerve response signals corresponds to one of the test stimulus signals delivered to one of the plurality of stimulating electrodes and wherein at least one of the plurality of stimulating electrodes is positioned on a surgical instrument adapted to be inserted into a human body;
   at least one processor in data communication with the nerve stimulator and the muscle response detector, wherein the at least one processor is configured to process the test stimulus signals and nerve response signals to determine at least one of a direction from the surgical instrument to the nerve or a distance from the surgical instrument to the nerve and wherein the at least one processor is configured to process the test stimulus signals and nerve response signals to determine a current for a nerve in a vicinity of the surgical instrument; and
   a display in data communication with the at least one processor, wherein the display is configured to receive and display data indicative of the direction from the surgical instrument to the nerve or data indicative of the distance from the surgical instrument to the nerve.

2. The neuromonitoring system of claim 1, wherein at least one of the plurality of stimulating electrodes is positioned on atho distal end of the surgical instrument.

3. The neuromonitoring system of claim 1, wherein the surgical instrument is at least one of a monopolar probe, a bipolar probe, a tissue dilator, a tissue retractor, a working cannula, a scalpel, a needle, an implant placement tool, a pedicle screw, a guidewire, or a sequential access surgical system.

4. The neuromonitoring system of claim 1, wherein the at least one processor is further configured to process the test stimulus signals and nerve response signals to determine at least one of an amplitude of a nerve response, a latency of a nerve response, a nerve integrity, or a nerve location.

5. The neuromonitoring system of claim 4, wherein the display is further configured to receive and display data indicative of the amplitude of the nerve response, the latency of the nerve response, the nerve integrity, or the nerve location.

6. The neuromonitoring system of claim 1, wherein the at least one processor is configured to generate data indicative of a warning if a threshold current is above a predefined threshold value.

7. The neuromonitoring system of claim 6, wherein the display is further configured to receive data indicative of the warning from the at least one processor and to issue a visual or auditory warning of potential injury based on the data indicative of the warning.

8. The neuromonitoring system of claim 1, wherein the at least one processor is configured to determine a response amplitude associated with each of the plurality of stimulating electrodes.

9. The neuromonitoring system of claim 8, wherein the at least one processor is configured to select one of the plurality of stimulating electrodes having a response amplitude that is largest relative to other response amplitudes.

10. The neuromonitoring system of claim 9, wherein the test stimulus signals have a current amplitude in a range of 1 mA to 100 mA, voltages in a range of 1V to 100V, and a frequency in a range of 1 msec to 1 sec.

11. The neuromonitoring system of claim 1, wherein the at least one processor is configured to generate data indicative of a map of nerves near an anatomical region.

12. The neuromonitoring system of claim 11, wherein the display is configured to receive and display the data indicative of the map of nerves near the anatomical region.

13. A neuromonitoring system configured to determine a location of a nerve, comprising:
a nerve stimulator configured to generate and deliver test stimulus signals to a plurality of stimulating electrodes;
a muscle response detector configured to detect nerve response signals, wherein each of the nerve response signals corresponds to one of the test stimulus signals delivered to one of the plurality of stimulating electrodes and wherein at least one of the plurality of stimulating electrodes is positioned on a surgical instrument adapted to be inserted into a human body;
at least one processor in data communication with the nerve stimulator and the muscle response detector, wherein the at least one processor is configured to process the test stimulus signals and nerve response signals to determine at least one of a direction from the surgical instrument to the nerve or a distance from the surgical instrument to the nerve and wherein the at least one processor is configured to determine a response latency associated with each of the plurality of stimulating electrodes; and
a display in data communication with the at least one processor, wherein the display is configured to receive and display data indicative of the direction from the surgical instrument to the nerve or data indicative of the distance from the surgical instrument to the nerve.

14. The neuromonitoring system of claim 13, wherein, for a combination of the plurality of stimulating electrodes, the at least one processor is configured to synchronize the test stimulus signals based on the response latency associated with each electrode in the combination of the plurality of stimulating electrodes.

15. The neuromonitoring system of claim 14, wherein the at least one processor synchronizes the test stimulus signals by causing the nerve stimulator to delay an initiation of each of the test stimulus signals to each electrode in the combination of the plurality of stimulating electrodes by an amount of time based on the response latency associated with each electrode in the combination of the plurality of stimulating electrodes.

16. A neuromonitoring system configured to determine a location of a nerve, comprising:
a nerve stimulator configured to generate and deliver test stimulus signals to a plurality of stimulating electrodes;
a muscle response detector configured to detect nerve response signals, wherein each of the nerve response signals corresponds to one of the test stimulus signals delivered to one of the plurality of stimulating electrodes and wherein at least one of the plurality of stimulating electrodes is positioned on a surgical instrument adapted to be inserted into a human body;
at least one processor in data communication with the nerve stimulator and the muscle response detector, wherein the at least one processor is configured to process the test stimulus signals and nerve response signals to determine at least one of a direction from the surgical instrument to the nerve or a distance from the surgical instrument to the nerve and wherein the at least one processor is configured to increase a signal to noise ratio of the nerve response signals by synchronizing test stimulus signals to two or more of the plurality of stimulating electrodes; and
a display in data communication with the at least one processor, wherein the display is configured to receive and display data indicative of the direction from the surgical instrument to the nerve or data indicative of the distance from the surgical instrument to the nerve.

17. A neuromonitoring system configured to generate a warning indicative of a possible injury to a nerve, comprising:
a nerve stimulator configured to generate and deliver test stimulus signals to a plurality of stimulating electrodes;
a muscle response detector configured to detect nerve response signals, wherein each of the nerve response signals corresponds to one of the test stimulus signals delivered to one of the plurality of stimulating electrodes and wherein at least one of the plurality of stimulating electrodes is positioned on a distal end of a surgical instrument adapted to be inserted into a human body;
at least one processor in data communication with the nerve stimulator and the muscle response detector, wherein the at least one processor is configured to process the test stimulus signals and nerve response signals to determine at least one of a direction from the surgical instrument to the nerve or a distance from the surgical instrument to the nerve, configured to process the test stimulus signals and nerve response signals to determine a current for a nerve in a vicinity of the surgical instrument, and configured to generate data indicative of a warning if a threshold current is above a predefined threshold value; and
a display in data communication with the at least one processor, wherein the display is configured to receive and display data indicative of the direction from the surgical instrument to the nerve or data indicative of the distance from the surgical instrument to the nerve and configured to receive data indicative of the warning from the at least one processor and to issue a visual or auditory warning of potential injury based on the data indicative of the warning.

18. The neuromonitoring system of claim 17, wherein the surgical instrument is at least one of a monopolar probe, a bipolar probe, a tissue dilator, a tissue retractor, a working cannula, a scalpel, a needle, an implant placement tool, a pedicle screw, a guidewire, or a sequential access surgical system.

19. The neuromonitoring system of claim 17, wherein the at least one processor is further configured to process the test stimulus signals and nerve response signals to determine at least one of an amplitude of a nerve response, a latency of a nerve response, a nerve integrity, or a nerve location and wherein the display is further configured to receive and display data indicative of the amplitude of the nerve response, the latency of the nerve response, the nerve integrity, or the nerve location.

20. The neuromonitoring system of claim 17, wherein the at least one processor is configured to increase a signal to noise ratio of the nerve response signals by synchronizing test stimulus signals to two or more of the plurality of stimulating electrodes.

* * * * *